US011013795B2

(12) United States Patent
Settembre et al.

(10) Patent No.: US 11,013,795 B2
(45) Date of Patent: May 25, 2021

(54) ANTIGENICALLY MATCHED INFLUENZA VACCINES

(71) Applicant: Seqirus UK Limited, Berkshire (GB)

(72) Inventors: Ethan Settembre, Cambridge, MA (US); Philip Dormitzer, Armonk, NY (US)

(73) Assignee: Seqirus UK Limited, Berkshire (GB)

(*) Notice: Subject to any disclaimer, the term of this patent is extended or adjusted under 35 U.S.C. 154(b) by 29 days.

(21) Appl. No.: 15/739,222

(22) PCT Filed: Jun. 24, 2016

(86) PCT No.: PCT/IB2016/053782
§ 371 (c)(1),
(2) Date: Dec. 22, 2017

(87) PCT Pub. No.: WO2016/207853
PCT Pub. Date: Dec. 29, 2016

(65) Prior Publication Data
US 2018/0177862 A1 Jun. 28, 2018

Related U.S. Application Data

(60) Provisional application No. 62/313,184, filed on Mar. 25, 2016, provisional application No. 62/185,532, filed on Jun. 26, 2015.

(51) Int. Cl.
| | | |
|---|---|---|
| *A61K 39/145* | (2006.01) | |
| *A61K 39/12* | (2006.01) | |
| *A61K 39/39* | (2006.01) | |
| *C12N 7/00* | (2006.01) | |
| *A61K 39/00* | (2006.01) | |

(52) U.S. Cl.
CPC ............ *A61K 39/145* (2013.01); *A61K 39/12* (2013.01); *A61K 39/39* (2013.01); *C12N 7/00* (2013.01); *A61K 2039/525* (2013.01); *A61K 2039/5252* (2013.01); *A61K 2039/53* (2013.01); *A61K 2039/545* (2013.01); *A61K 2039/55566* (2013.01); *A61K 2039/70* (2013.01); *C12N 2760/16121* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS 5,948,410 A 9/1999 Van Scharrenburg et al.

FOREIGN PATENT DOCUMENTS

| WO | WO 2007/052057 A2 | 5/2007 |
| WO | WO 2007/144772 A2 | 12/2007 |
| WO | WO 2009/150532 A1 | 12/2009 |
| WO | WO 2010/092476 A1 | 8/2010 |
| WO | WO 2013/131898 A1 | 9/2013 |

OTHER PUBLICATIONS

Shin et al., Comparison of immunogenicity of cell-and egg-passaged viruses formanufacturing MDCK cell culture-based influenza vaccines, 2015, Virus Research, vol. 204, pp. 40-46.*
Gu et al., Do People Taking Flu Vaccines Need Them the Most?, 2011, Plos One, vol. 6, No. 12.*
Manini et al., Flucelvax (Optaflu) for seasonal influenza, 2015, Expert Review of Vaccines, vol. 14, No. 6, pp. 789-804.*
Dormitzer et al., Synthetic Generation of Influenza Vaccine Viruses for Rapid Response to Pandemics, 2013, Science Translational Medicine, vol. 5, No. 185.*
Tricco et al., "Comparing influenza vaccine efficacy against mismatched and matched strains: a systematic review and meta-analysis," BMC Med, 11:153, (2013).
Barr et al., "Epidemiological, antigenic and genetic characteristics of seasonal influenza A(H1N1), A(H3N2) and B influenza viruses: basis for the WHO recommendation on the composition of influenza vaccines for use in the 2009-2010 northern hemisphere season," Vaccine, 28(5):1156-1167, (2010).
Dormitzer et al., "Synthetic generation of influenza vaccine viruses for rapid response to pandemics," Sci Transl Med, 5(185):185ra68, (2013).
Genzel et al., "Continuous cell lines as a production system for influenza vaccines," Expert Rev Vaccines, 8(12):1681-1692, (2009).
Hardelid et al., "Effectiveness of pandemic and seasonal influenza vaccine in preventing pandemic influenza A(H1N1)2009 infection in England and Scotland 2009-2010," Euro Surveill, 16(2), (2011).
Koopman et al., "Immune-response profiles induced by human immunodeficiency virus type 1 vaccine DNA, protein or mixed-modality immunization: increased protection from pathogenic simian-human immunodeficiency virus viraemia with protein/DNA combination," J Gen Virol, 89(Pt 2):540-543, (2008).
Suphaphiphat et al., "Antigenic characterization of influenza viruses produced using synthetic DNA and novel backbones," Vaccine, 34(32):3641-3648, (2016).
International Search Report of International Application No. PCT/IB2016/053782, dated Jan. 17, 2017.
Written Opinion of the International Searching Authority for International Application No. PCT/IB2016/053782.
Nolan et al., "Heterologous Prime-Boost Vaccination Using an AS03$_B$-Adjuvanted Influenza A(H5N1) Vaccine in Infants and Children <3 Years of Age," J Infect Dis, 210(11): 1800-1810 (2014).

* cited by examiner

*Primary Examiner* — Benjamin P Blumel
(74) *Attorney, Agent, or Firm* — Finnegan, Henderson, Farabow, Garrett & Dunner, LLP

(57) ABSTRACT

Disclosed herein are influenza vaccine compositions, related preparations and intermediates, formulations, production methods, immunization methods, and use thereof, for achieving improved immune-protection in human subjects. More specifically, non-egg-based influenza vaccines are described, which provide improved antigenic match.

23 Claims, 12 Drawing Sheets

Specification includes a Sequence Listing.

A/Hong Kong/5738/2014 (3C.2A)

FIG. 5

Panel of synthetic viruses generated for antigenic characterization.

| Virus strain | Antigen source[1] | PR8x | Flu A Backbones #19 | #21 |
|---|---|---|---|---|
| A/H1N1/Christchurch/16/2010 (NIB74) | egg | RG-PS-1259 | RG-PS-1260 | RG-PS-1261 |
| A/H3N2/Brisbane/299/2011 (IVR164) | egg | RG-PS-1472 | RG-PS-1468 | RG-PS-1469 |
| A/H3N2/Uruguay/716/2007 (X175C) | egg | RG-PS-2385 | RG-ID-733 | RG-PS-2358 |
| A/H3N2/Texas/50/2012 | egg | RG-ID-1958 | RG-ID-1959 | RG-PS-2334 |
| A/H3N2/Berlin/93/2011 | egg | RG-PS-1425 | RG-PS-1286 | RG-PS-1287 |
| A/H3N2/SouthAustralia/3/2011 | cell | RG-PS-1322 | RG-PS-1323 | RG-PS-1327 |
| A/H3N2/Victoria/210/2009 (X187) | egg | RG-PS-1274 | RG-PS-1266 | RG-PS-1267 |
| A/H3N2/Victoria/210/2009 | cell | RG-PS-2378 | RG-KD-038 | RG-PS-2381 |
| A/H3N2/Victoria/361/2011 (IVR165) | egg | RG-PS-1291 | RG-PS-1242 | RG-PS-1252 |
| A/H3N2/Victoria/361/2011 | cell | RG-PS-1247 | n/a | n/a |
| A/H3N2/Switzerland/9715293/2013 | egg | RG-PS-2404 | n/a | RG-PS-2411 |
| A/H3N2/Switzerland/9715293/2013 | cell | RG-PS-2407 | RG-PS-2400 | RG-ID-1985 |

| | | Flu B Backbone |
|---|---|---|
| B/Brisbane/60/2008 | egg | RG-ID-1279 |
| B/Brisbane/60/2008 | cell | RG-PS-1376 |

[1] "egg" or "cell" under antigen source refers to the passage history of the viruses that provided the HA and NA sequences for synthesis. In cases of mixed passage history, any passage in eggs is sufficient to trigger an "egg" designation. All synthetic test viruses were passaged exclusively in mammalian cells for these studies, regardless of the HA and NA sequences used.

FIG. 6 HI comparison of egg-propagated non

FIG. 7

HI characterization of synthetic viruses with HA and NA sequences derived from egg- or mammalian-propagated wild-type viruses

| | | | | Hemagglutination inhibition titer | | | |
|---|---|---|---|---|---|---|---|
| | | | | Ferret antisera raised to wild-type isolates[3] | | | |
| | | | | A/Texas/50/12 egg | A/Berlin/93/11 egg | A/South Australia/3/11 cell | A/Victoria/210/09 cell |
| Origin[1] | Viruses[2] | genetic group | passage history | F42/13 | F10/12 | AUG F20/08 | T/C St Judes F712/14 |
| WT | A/Texas/50/2012 – egg | A(H3N2) | egg (E5/E2) | 2560 | | | |
| S | RG-PS-1958 (A/Texas/50/2012-egg) PR8x | clade 3C.1 | cell (MDCK1) | 2560 | | | |
| S | RG-PS-1959 (A/Texas/50/2012-egg) #19 | | cell (MDCK1) | 2560 | | | |
| S | RG-PS-2334 (A/Texas/50/2012-egg) #21 | | cell (MDCK1) | 1280 | | | |
| WT | A/Berlin/93/2011 – egg | A(H3N2) | egg (NVD3/E3) | | 2560 | | |
| S | RG-PS-1425 (A/Berlin/93/2011-egg) PR8x | clade 3C | cell (MDCK1) | | 10240 | | |
| S | RG-PS-1286 (A/Berlin/93/2011-egg) #19 | | cell (MDCK1) | | 5120 | | |
| S | RG-PS-1287 (A/Berlin/93/2011-egg) #21 | | cell (MDCK1) | | 10240 | | |
| WT | A/South Australia/3/2011 - cell | A(H3N2) | cell MDCK2/SIAT2 | | | 2560 | |
| S | RG-PS-1322 (A/South Australia/3/2011-cell) PR8x | clade 3C | cell (MDCK1) | | | 5120 | |
| S | RG-PS-1323 (A/South Australia/3/2011-cell) #19 | | cell (MDCK1) | | | 2560 | |
| S | RG-PS-1327 (A/South Australia/3/2011-cell) #21 | | cell (MDCK1) | | | 5120 | |
| WT | A/Victoria/210/2009 - cell | A(H3N2) | cell (MDCK2/SIAT5) | | | | 2560 |
| S | RG-PS-2378 (A/Victoria/210/2009-cell) PR8x | | cell (MDCK1) | | | | 2560 |
| S | RG-KD-038 (A/Victoria/210/2009-cell) #19 | | cell (MDCK1) | | | | 5120 |
| S | RG-PS-2381 (A/Victoria/210/2009-cell) #21 | | cell (MDCK1) | | | | 5120 |

[1]S= synthetic virus, WT = wild-type isolate

[2,3] "egg" or "cell" refers to the passage history of the wild-type viruses or the passage history of the reference viruses that provided the HA and NA sequences to make the synthetic viruses. In cases of mixed passage history, any passage in eggs is sufficient to trigger an "egg" designation.

Homologous titers are indicated in bold and underlined.

FIG. 8

HI titers showing antigenic mismatch between viruses with egg- and mammalian cell-derived H3N2 antigens

A. A/Victoria/210/2009 (H3N2)

| | | | Post-infection

FIG. 9

HI titers showing antigenic mismatch between viruses with egg- and mammalian cell-derived B antigens

| | antigen source[1] | passage history | Post-infection ferret antisera | |
|---|---|---|---|---|
| | | | B/Brisbane/60/08 - egg F30/10 | B/Brisbane/60/08 - cell NIBSC66/10 |
| REFERENCE VIRUSES | | | | |
| B/Brisbane/60/2008 – egg | Egg | Egg (E4/E3) | <u>640</u> | 160 |
| B/Brisbane/60/2008 – cell | Cell | Cell (MDCKx/MDCK4) | 20 | <u>160</u> |
| SYNTHETIC TEST VIRUSES | | | | |
| RG-ID-1279 (B/Brisbane/60/2008-egg) | Egg | Cell (MDCK1) | 640 | 160 |
| RG-PS-1376 (B/Brisbane/60/2008-cell) | Cell | Cell (MDCK3) | 40 | 160 |

[1] "egg" or "cell" refers to the passage history of the reference viruses or the passage history of the viruses that provided the HA and NA sequences to make the synthetic viruses.

Homologous titers are indicated in bold and underlined.

FIG. 10

Two-way HI test for the H3N2 strain A/Switzerland/9715293/2013

| | antigen source[1] | passage history | Post-infection ferret antisera[2] | | | |
|---|---|---|---|---|---|---|
| | | | A/Switz/9715293 (WT) egg | A/Switz/9715293 (WT) cell | A/Switz/9715293 (S) egg RG-PS-2404 | A/Switz/9715293 (S) cell RG-ID-1985 |
| | | | NIBSC F29/15 | NIBSC F13/14 | F40/14 | F439/14 |
| REFERENCE VIRUSES | | | | | | |
| A/Switzerland/9715293/2013 – egg | Egg | E4/E1 clone 123 | 640 | 160 | 1280 | 160 |
| A/Switzerland/9715293/20132 – cell | Cell | SIAT1/SIAT3 | 80 | 320 | 320 | 320 |
| TEST VIRUSES | | | | | | |
| RG-PS-2404 (A/Switzerland/9715293/2013–egg) PR8x | Egg | MDCK1 | 320 | 160 | 640 | 160 |
| RG-PS-2411 (A/Switzerland/9715293/2013–egg) #21 | Egg | MDCK1 | 320 | 160 | 640 | 160 |
| RG-PS-2407 (A/Switzerland/9715293/2013–cell) PR8x | Cell | MDCK1 | 160 | 320 | 320 | 320 |
| RG-ID-1985 (A/Switzerland/9715293/2013–cell) #21 | Cell | MDCK1 | 160 | 640 | 640 | 640 |
| RG-PS-2400 (A/Switzerland/9715293/2013–cell) #19 | Cell | MDCK1 | 160 | 320 | 320 | 320 |

[1] "egg" or "cell" refers to the passage history of the reference viruses or the passage history of the viruses that provided the HA and NA sequences to make the synthetic viruses.

[2] Post-infection ferret antisera was raised to either wild-type isolates (WT) or synthetic viruses (S)

Homologous titers are indicated in bold and underl

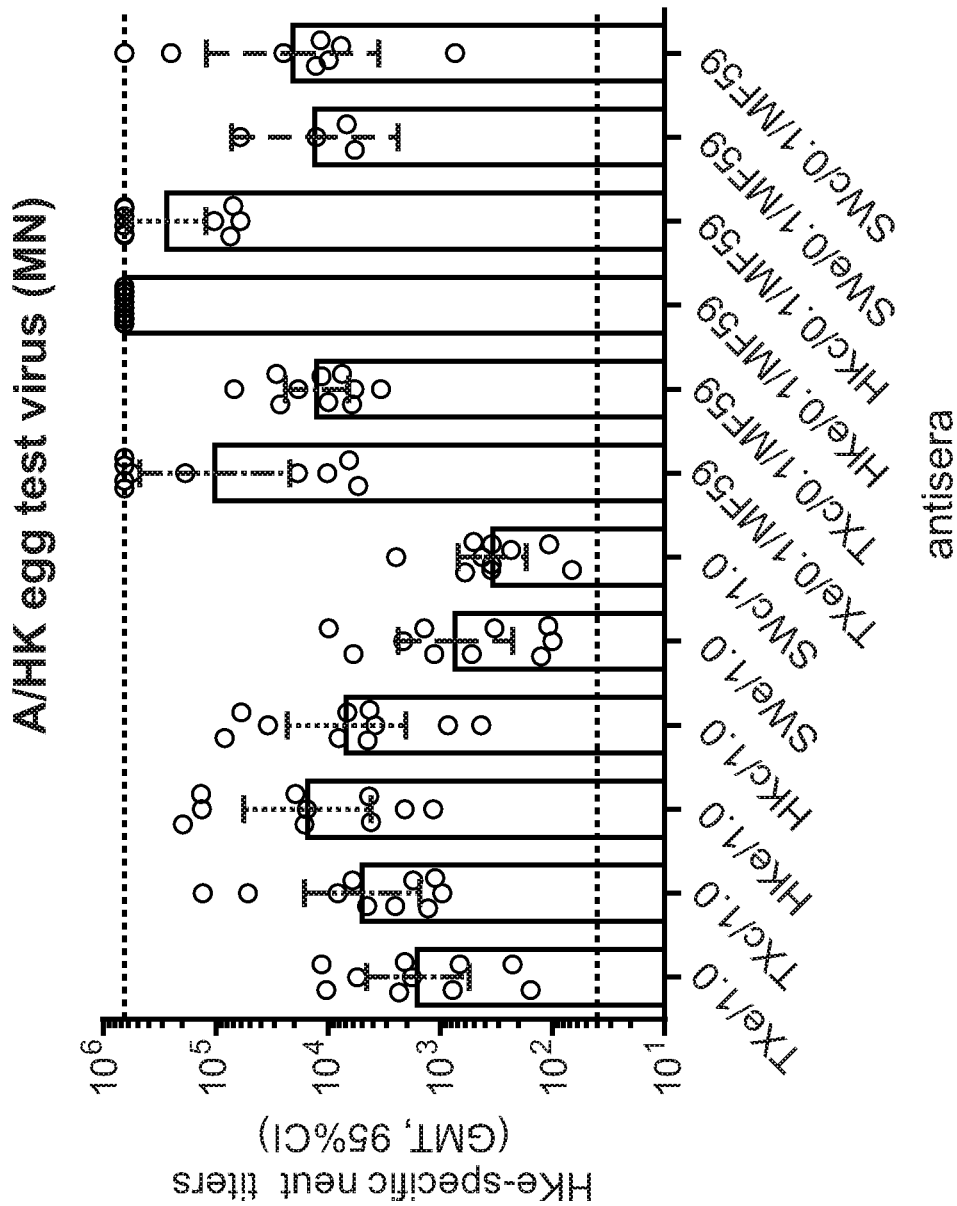

FIG. 11B

A/HK cell test virus (MN)

SEQUENCE LISTING

<160> NUMBER OF SEQ ID NOS: 17

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ttgggtaacg ccagggtttt cc                                        22

<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
ttcacacagg aaacagctat gaccatgatt a                              31

<210> SEQ ID NO 3
<211> LENGTH: 566
<212> TYPE: PRT
<213> ORGANISM: Influenza A virus

<400> SEQUENCE: 3

Met Lys Ala Ile Leu Val Val Leu Leu His Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asn Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asp His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro

```
                165                 170                 175
Thr Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asn Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Ala Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 4
```

```
<211> LENGTH: 566
<212> TYPE: PRT
<213> ORGANISM: Influenza A virus

<400> SEQUENCE: 4

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

G

```
                385                 390                 395                 400
        Ile Gly Lys Thr Asn Glu Lys Phe His Gln Ile Glu Lys Glu Phe Ser
                        405                 410                 415
        Glu Val Glu Gly Arg Ile Gln Asp Leu Glu Lys Tyr Val Glu Asp Thr
                        420                 425                 430
        Lys Ile Asp Leu Trp Ser Tyr Asn Ala Glu Leu Leu Val Ala Leu Glu
                        435                 440                 445
        Asn Gln His Thr Ile Asp Leu Thr Asp Ser Glu Met Asn Lys Leu Phe
                        450                 455                 460
        Glu Lys Thr Lys Lys Gln Leu Arg Glu Asn Ala Glu Asp Met Gly Asn
        465                 470                 475                 480
        Gly Cys Phe Lys Ile Tyr His Lys Cys Asp Asn Ala Cys Ile Gly Ser
                        485                 490                 495
        Ile Arg Asn Gly Thr Tyr Asp His Asn Val Tyr Arg Asp Glu Ala Leu
                        500                 505                 510
        Asn Asn Arg Phe Gln Ile Lys Gly Val Glu Leu Lys Ser Gly Tyr Lys
                        515                 520                 525
        Asp Trp Ile Leu Trp Ile Ser Phe Ala Ile Ser Cys Phe Leu Leu Cys
                        530                 535                 540
        Val Ala Leu Leu Gly Phe Ile Met Trp Ala Cys Gln Lys Gly Asn Ile
        545                 550                 555                 560
        Arg Cys Asn Ile Cys Ile
                        565

<210> SEQ ID NO 5
<211> LENGTH: 566
<212> TYPE: PRT
<213> ORGANISM: Influenza A virus

<400> SEQUENCE: 5

Met Lys Thr Ile Ile Ala Leu Ser Tyr Ile Leu Cys Leu Val Phe Ala
        1               5                   10                  15
        Gln Lys Leu Pro Gly Asn Asp Asn Ser Thr Ala Thr Leu Cys Leu Gly
                        20                  25                  30
        His His Ala Val Pro Asn Gly Thr Ile Val Lys Thr Ile Thr Asn Asp
                        35                  40                  45
        Gln Ile Glu Val Thr Asn Ala Thr Glu Leu Val Gln Asn Ser Ser Thr
                        50                  55                  60
        Gly Glu Ile Cys Asp Ser Pro His Gln Ile Leu Asp Gly Lys Asn Cys
        65                  70                  75                  80
        Thr Leu Ile Asp Ala Leu Leu Gly Asp Pro Gln Cys Asp Gly Phe Gln
                        85                  90                  95
        Asn Lys Lys Trp Asp Leu Phe Val Glu Arg Ser Lys Ala Tyr Ser Asn
                        100                 105                 110
        Cys Tyr Pro Tyr Asp Val Pro Asp Tyr Ala Ser Leu Arg Ser Leu Val
                        115                 120                 125
        Ala Ser Ser Gly Thr Leu Glu Phe Asn Asn Glu Ser Phe Asn Trp Thr
                        130                 135                 140
        Gly Val Thr Gln Asn Gly Thr Ser Ser Ala Cys Ile Arg Arg Ser Lys
        145                 150                 155                 160
        Asn Ser Phe Phe Ser Arg Leu Asn Trp Leu Thr His Leu Asn Phe Lys
                        165                 170                 175
        Tyr Pro Ala Leu Asn Val Thr Met Pro Asn Asn Glu Gln Phe Asp Lys
                        180                 185                 190
```

```
Leu Tyr Ile Trp Gly Val His His Pro Gly Thr Asp Lys Asp Gln Ile
            195                 200                 205

Phe Leu Tyr Ala Gln Ala Ser Gly Arg Ile Thr Val Ser Thr Lys Arg
        210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Met Gln Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 6
<211> LENGTH: 566
<212> TYPE: PRT
<213> ORGANISM: Influenza A virus

<400> SEQUENCE: 6
```

```
Met Lys Thr Ile Ile Ala Leu Ser His Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Asn Ser Ser Ile
50                  55                  60

Gly Glu Ile Cys Asp Ser Pro His Gln Ile Leu Asp Gly Glu Asn Cys
65                      70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr Gln Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Val Thr Asp Lys Asp Gln Ile
            195                 200                 205

Phe Leu Tyr Ala Gln Ser Ser Gly Arg Ile Thr Val Ser Thr Lys Arg
210                 215                 220

Ser Gln Gln Ala Val Ile Pro Asn Ile Gly Tyr Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Arg Gly Gln Ala Ala Asp Leu Lys
            370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415
```

```
Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 7
<211> LENGTH: 566
<212> TYPE: PRT
<213> ORGANISM: Influenza A virus

<400> SEQUENCE: 7

Met Lys Thr Ile Ile Ala Leu Ser His Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Asn Ser Ser Ile
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220
```

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
            245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 8
<211> LENGTH: 566
<212> TYPE: PRT
<213> ORGANISM: Influenza A virus

<400> SEQUENCE: 8

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly

```
                20                  25                  30
His His Ala Val Pro Asn Gly Thr Ile Val Lys Thr Ile Thr Asn Asp
            35                  40                  45
Arg Ile Glu Val Thr Asn Ala Thr Glu Leu Val Gln Asn Ser Ser Ile
        50                  55                  60
Gly Glu Ile Cys Asp Ser Pro His Gln Ile Leu Asp Gly Glu Asn Cys
65                  70                  75                  80
Thr Leu Ile Asp Ala Leu Leu Gly Asp Pro Gln Cys Asp Gly Phe Gln
                85                  90                  95
Asn Lys Lys Trp Asp Leu Phe Val Glu Arg Ser Lys Ala Tyr Ser Asn
            100                 105                 110
Cys Tyr Pro Tyr Asp Val Pro Asp Tyr Ala Ser Leu Arg Ser Leu Val
        115                 120                 125
Ala Ser Ser Gly Thr Leu Glu Phe Asn Asn Glu Ser Phe Asn Trp Asn
    130                 135                 140
Gly Val Thr Gln Asn Gly Thr Ser Ser Ala Cys Ile Arg Arg Ser Asn
145                 150                 155                 160
Asn Ser Phe Phe Ser Arg Leu Asn Trp Leu Thr His Leu Asn Phe Lys
                165                 170                 175
Tyr Pro Ala Leu Asn Val Thr Met Pro Asn Asn Glu Gln Phe Asp Lys
            180                 185                 190
Leu Tyr Ile Trp Gly Val His His Pro Val Thr Asp Lys Asp Gln Ile
        195                 200                 205
Phe Leu Tyr Ala Gln Pro Ser Gly Arg Ile Thr Val Ser Thr Lys Arg
    210                 215                 220
Ser Gln Gln Ala Val Ile Pro Asn Ile Gly Phe Arg Pro Arg Ile Arg
225                 230                 235                 240
Asn Ile Pro Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Ser Gly Lys Ser Ser Ile Met Arg Ser Asp Ala
        275                 280                 285
Pro Ile Gly Lys Cys Lys Ser Glu Cys Ile Thr Pro Asn Gly Ser Ile
    290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Ser Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Arg Gly Gln Ala Ala Asp Leu Lys
    370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
```

```
Asn Gln His Thr Ile Asp Leu Thr Asp Ser Glu Met Asn Lys Leu Phe
        450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 9
<211> LENGTH: 566
<212> TYPE: PRT
<213> ORGANISM: Influenza A virus

<400> SEQUENCE: 9

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Asn
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Pro Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
```

```
            245                 250                 255
Asp Ile Leu Leu Ile Asn Ser Thr Gly Asn Leu Ile Ala Pro Arg Gly
        260                 265                 270

Tyr Phe Lys Ile Arg Ser Gly Lys Ser Ser Ile Met Arg Ser Asp Ala
    275                 280                 285

Pro Ile Gly Lys Cys Lys Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Arg Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 10
<211> LENGTH: 566
<212> TYPE: PRT
<213> ORGANISM: Influenza A virus

<400> SEQUENCE: 10

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45
```

```
Gln Ile Glu Val Thr Asn Ala Thr Glu Leu Val Gln Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Glu Ser Phe Asn Trp Thr
130                 135                 140

Gly Val Thr Gln Asn Gly Thr Ser Ser Cys Ile Arg Gly Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
                180                 185                 190

Leu Tyr Ile Trp Gly Val His His Pro Gly Thr Asp Asn Asp Gln Ile
    195                 200                 205

Phe Pro Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
```

```
                465              470               475              480
        Gly Cys Phe Lys Ile Tyr His Lys Cys Asp Asn Ala Cys Ile Gly Ser
                        485              490              495

Ile Arg Asn Gly Thr Tyr Asp His Asp Val Tyr Arg Asp Glu Ala Leu
                        500              505              510

Asn Asn Arg Phe Gln Ile Lys Gly Val Glu Leu Lys Ser Gly Tyr Lys
                        515              520              525

Asp Trp Ile Leu Trp Ile Ser Phe Ala Ile Ser Cys Phe Leu Leu Cys
                        530              535              540

Val Ala Leu Leu Gly Phe Ile Met Trp Ala Cys Gln Lys Gly Asn Ile
        545              550              555              560

Arg Cys Asn Ile Cys Ile
                        565

<210> SEQ ID NO 11
<211> LENGTH: 566
<212> TYPE: PRT
<213> ORGANISM: Influenza A virus

<400> SEQUENCE: 11

Met Lys Thr Ile Ile Ala Leu Ser Tyr Ile Leu Cys Leu Val Phe Ala
        1               5                   10                  15

Gln Lys Leu Pro Gly Asn Asp Asn Ser Thr Ala Thr Leu Cys Leu Gly
                        20                  25                  30

His His Ala Val Pro Asn Gly Thr Ile Val Lys Thr Ile Thr Asn Asp
                        35                  40                  45

Gln Ile Glu Val Thr Asn Ala Thr Glu Leu Val Gln Ser Ser Ser Thr
                50                  55                  60

Gly Glu Ile Cys Asn Ser Pro His Gln Ile Leu Asp Gly Glu Asn Cys
        65                  70                  75                  80

Thr Leu Ile Asp Ala Leu Leu Gly Asp Pro Gln Cys Asp Gly Phe Gln
                        85                  90                  95

Asn Lys Lys Trp Asp Leu Phe Val Glu Arg Ser Lys Ala His Ser Asn
                        100                 105                 110

Cys Tyr Pro Tyr Asp Val Pro Asp Tyr Ala Ser Leu Arg Ser Leu Val
                        115                 120                 125

Ala Ser Ser Gly Thr Leu Glu Phe Asn Asn Glu Ser Phe Asn Trp Thr
                        130                 135                 140

Gly Val Thr Gln Asn Gly Thr Ser Ser Ser Cys Ile Arg Arg Ser Asn
        145                 150                 155                 160

Asn Ser Phe Phe Ser Arg Leu Asn Trp Leu Thr His Leu Asn Phe Lys
                        165                 170                 175

Tyr Pro Ala Leu Asn Val Thr Met Pro Asn Asn Glu Gln Phe Asp Lys
                        180                 185                 190

Leu Tyr Ile Trp Gly Val His His Pro Asp Thr Asp Lys Gly Gln Ile
                        195                 200                 205

Phe Leu Tyr Ala Gln Ala Ala Gly Arg Ile Thr Val Ser Thr Lys Arg
                        210                 215                 220

Ser Gln Gln Ala Val Ile Pro Asn Val Gly Phe Arg Pro Arg Val Arg
        225                 230                 235                 240

Asn Ile Pro Ser Arg Val Ser Ile Tyr Trp Thr Ile Val Lys Pro Gly
                        245                 250                 255

Asp Ile Leu Leu Ile Asn Ser Thr Gly Asn Leu Ile Ala Pro Arg Gly
                        260                 265                 270
```

```
Tyr Phe Lys Ile Arg Ser Gly Lys Ser Ser Ile Met Arg Ser Asp Ala
                275                 280                 285

Pro Ile Gly Lys Cys Asn Ser Ala Cys Ile Thr Pro Asn Gly Ser Ile
    290                 295                 300

Pro Thr Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Lys Thr Arg Gly Ile Phe Gly Ala Ile Ala
                340                 345                 350

Gly Phe Ile Glu Asn Gly Trp Glu Gly Met Val Asp Gly Trp Tyr Gly
            355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
            530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 12
<211> LENGTH: 566
<212> TYPE: PRT
<213> ORGANISM: Influenza A virus

<400> SEQUENCE: 12

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80
```

-continued

```
Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr Arg Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495
```

-continued

```
Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Thr Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 13
<211> LENGTH: 566
<212> TYPE: PRT
<213> ORGANISM: Influenza A virus

<400> SEQUENCE: 13

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300
```

```
Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 14
<211> LENGTH: 566
<212> TYPE: PRT
<213> ORGANISM: Influenza A virus

<400> SEQUENCE: 14

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Arg Ile Glu Val Thr Asn Ala Thr Glu Leu Val Gln Asn Ser Ser Ile
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
```

```
              100                 105                 110
    Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Ala
            130                 135                 140

Gly Val Thr Gln Asn Gly Thr Ser Ser Cys Ile Arg Gly Ser Asn
    145                 150                 155                 160

Ser Ser Phe Phe Ser Arg Leu Asn Trp Leu Thr His Leu Asn Ser Lys
                    165                 170                 175

Tyr Pro Ala Leu Asn Val Thr Met Pro Asn Asn Glu Gln Phe Asp Lys
                180                 185                 190

Leu Tyr Ile Trp Gly Val His His Pro Gly Thr Asp Lys Asp Gln Ile
            195                 200                 205

Phe Leu Tyr Ala Gln Ser Ser Gly Arg Ile Thr Val Ser Thr Lys Arg
            210                 215                 220

Ser Gln Gln Ala Val Ile Pro Asn Ile Gly Ser Arg Pro Arg Ile Arg
    225                 230                 235                 240

Asp Ile Pro Ser Arg Ile Ser Ile Tyr Trp Thr Ile Val Lys Pro Gly
                    245                 250                 255

Asp Ile Leu Leu Ile Asn Ser Thr Gly Asn Leu Ile Ala Pro Arg Gly
                    260                 265                 270

Tyr Phe Lys Ile Arg Ser Gly Lys Ser Ser Ile Met Arg Ser Asp Ala
                275                 280                 285

Pro Ile Gly Lys Cys Lys Ser Glu Cys Ile Thr Pro Asn Gly Ser Ile
            290                 295                 300

Pro Asn Asp Lys Pro Phe Gln Asn Val Asn Arg Ile Thr Tyr Gly Ala
    305                 310                 315                 320

Cys Pro Arg Tyr Val Lys Gln Ser Thr Leu Lys Leu Ala Thr Gly Met
                    325                 330                 335

Arg Asn Val Pro Glu Arg Gln Thr Arg Gly Ile Phe Gly Ala Ile Ala
                    340                 345                 350

Gly Phe Ile Glu Asn Gly Trp Glu Gly Met Val Asp Gly Trp Tyr Gly
                355                 360                 365

Phe Arg His Gln Asn Ser Glu Gly Arg Gly Gln Ala Ala Asp Leu Lys
            370                 375                 380

Ser Thr Gln Ala Ala Ile Asp Gln Ile Asn Gly Lys Leu Asn Arg Leu
    385                 390                 395                 400

Ile Gly Lys Thr Asn Glu Lys Phe His Gln Ile Glu Lys Glu Phe Ser
                    405                 410                 415

Glu Val Glu Gly Arg Ile Gln Asp Leu Glu Lys Tyr Val Glu Asp Thr
                    420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
            450                 455                 460

Glu Lys Thr Lys Lys Gln Leu Arg Glu Asn Ala Glu Asp Met Gly Asn
    465                 470                 475                 480

Gly Cys Phe Lys Ile Tyr His Lys Cys Asp Asn Ala Cys Ile Gly Ser
                    485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525
```

```
Asp Trp Ile Leu Trp Ile Ser Phe Ala Ile Ser Cys Phe Leu Leu Cys
            530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 15
<211> LENGTH: 566
<212> TYPE: PRT
<213> ORGANISM: Influenza A virus

<400> SEQUENCE: 15

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Arg Ile Glu Val Thr Asn Ala Thr Glu Leu Val Gln Asn Ser Ser Ile
50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ala
130                 135                 140

Gly Val Thr Gln Asn Gly Thr Ser Ser Ser Cys Arg Arg Gly Ser Asn
145                 150                 155                 160

Ser Ser Phe Phe Ser Arg Leu Asn Trp Leu Thr His Leu Asn Ser Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Val Thr Asp Lys Asp Gln Ile
        195                 200                 205

Phe Leu Tyr Ala Gln Ser Ser Gly Arg Ile Thr Val Ser Thr Lys Arg
210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
```

```
              325                 330                 335
Arg Asn Val Pro Glu Arg Gln Thr Arg Gly Ile Phe Gly Ala Ile Ala
            340                 345                 350
Gly Phe Ile Glu Asn Gly Trp Glu Gly Met Val Asp Gly Trp Tyr Gly
            355                 360                 365
Phe Arg His Gln Asn Ser Glu Gly Arg Gly Gln Ala Ala Asp Leu Lys
            370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
            450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
                500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
            530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 16
<211> LENGTH: 585
<212> TYPE: PRT
<213> ORGANISM: Influenza B virus

<400> SEQUENCE: 16

Met Lys Ala Ile Ile Val Leu Leu Met Val Val Thr Ser Asn Ala Asp
1               5                   10                  15
Arg Ile Cys Thr Gly Ile Thr Ser Ser Asn Ser Pro His Val Val Lys
            20                  25                  30
Thr Ala Thr Gln Gly Glu Val Asn Val Thr Gly Val Ile Pro Leu Thr
        35                  40                  45
Thr Thr Pro Thr Lys Ser His Phe Ala Asn Leu Lys Gly Thr Glu Thr
    50                  55                  60
Arg Gly Lys Leu Cys Pro Lys Cys Leu Asn Cys Thr Asp Leu Asp Val
65                  70                  75                  80
Ala Leu Gly Arg Pro Lys Cys Thr Gly Lys Ile Pro Ser Ala Arg Val
                85                  90                  95
Ser Ile Leu His Glu Val Arg Pro Val Thr Ser Gly Cys Phe Pro Ile
            100                 105                 110
Met His Asp Arg Thr Lys Ile Arg Gln Leu Pro Asn Leu Leu Arg Gly
            115                 120                 125
```

```
Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Glu Ala Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
    435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
```

```
                545                 550                 555                 560
Ala Val Thr Leu Met Ile Ala Ile Phe Val Val Tyr Met Val Ser Arg
                        565                 570                 575

Asp Asn Val Ser Cys Ser Ile Cys Leu
            580                 585

<210> SEQ ID NO 17
<211> LENGTH: 585
<212> TYPE: PRT
<213> ORGANISM: Influenza B virus

<400> SEQUENCE: 17

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335
```

-continued

```
Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                     390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
        450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
            530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585
```

ANTIGENICALLY MATCHED INFLUENZA VACCINES

This application is a national stage filing under 35 U.S.C. § 371 of International Application No. PCT/IB2016/053782, filed on Jun. 24, 2016, which claims the benefit of the filing dates of U.S. Provisional Application No. 62/313,184, filed on Mar. 25, 2016, and U.S. Pat. No. 62,185,532, filed on Jun. 26, 2015, all of which are incorporated herein by reference.

This application claims the benefit of U.S. Provisional Application No. 62/185,532 (filed 26 Jun. 2015) and U.S. Provisional Application No. 62/313,184 (filed 25 Mar. 2016), the complete contents of which are hereby incorporated herein by reference for all purposes.

FIELD OF THE INVENTION

This invention relates generally to vaccines, more specifically to improved influenza vaccines.

BACKGROUND OF THE INVENTION

Influenza can lead to severe illness and even death. The best way to protect against the disease is to get vaccinated as a preventive measure. However, a major challenge for influenza vaccine manufacturers is that influenza viruses are constantly changing, thus requiring influenza vaccines to be adapted to the circulating strains each year. To this end, the World Health Organization (WHO) monitors influenza globally and proposes influenza strains each year that should be included in influenza vaccines in the forthcoming influenza season.

Whilst the influenza strains chosen by the WHO have generally proven to be a good match for the circulating influenza strains, there have been occasions where the circulating strains no longer matched the influenza strain found in the vaccine well and where the influenza vaccine therefore had a lower efficacy. For example, in the 2014/2015 season there was a mismatch between the H3N2 strain selected for the vaccine and the circulating H3N2 strain, resulting in the vaccine providing poor protection against this strain.

Antigenic mismatch observed in vaccine preparations has been attributed to so-called adaptation, e.g., egg adaptation. This is illustrated in studies that showed egg passage resulted in egg-adaptive loss of glycosylation that affects antigenicity. Kishida et al. (Ref. 119), for example, reported egg-adaptive loss of glycosylation in a B-Victoria virus which resulted in changes in antigenicity.

In the 1986/87 season, two influenza vaccines were manufactured as a result of the emergence of a new H1N1 influenza strain later in the season. Regulators in that case recommended for a monovalent influenza vaccine prepared from an influenza virus grown in eggs against the new H1N1 strain to be manufactured and administered to high-risk persons in addition to the trivalent seasonal influenza vaccine which had been made available earlier in the season.

Limited efficacy/effectiveness in immuno-protection caused by antigenic mismatch in influenza vaccines remains a challenge.

SUMMARY OF THE INVENTION

The present invention is based at least in part on the recognition that seasonal influenza vaccines in certain influenza seasons lack desirable vaccine efficacy (in clinical context) or vaccine effectiveness (in epidemiological context) due to antigenic mismatch between vaccine strains and circulating viruses. In recent years, ineffective flu vaccines have been observed in an alarming number of flu seasons. The present invention provides solutions to the existing unmet needs for improved influenza vaccines with better antigenic match, for example, in the form of rescue vaccines and hybrid vaccines, which are described in more detail herein.

The rescue vaccine and the hybrid vaccine have in common that both are contemplated to include an antigen that has been produced in an egg-free process, and both include an antigen that provides antigenic match to circulating viruses in the way conventional egg-based vaccines cannot achieve.

Note that recommended strains are currently limited to strains that grow in eggs (egg-adapted versions) and that can be readily detected and measured by standard assays, in order to accommodate for traditional egg-based vaccine manufacture. In some situations, however, influenza viruses of certain clades fail to grow well in eggs, in which case, a different but related clade with better ability to grow in eggs may be selected as a default. The use of a strain from an unmatched clade can lead to antigenic mismatch in the resulting vaccines, and this remains a problem today.

Rescue vaccines are typically produced off-cycle, following a regular seasonal flu vaccine that has been found to be ineffective in providing sufficient immuno-protection due to antigenic mismatch. Thus, a rescue vaccine may be used as a "follow-up" vaccine to supplement regular seasonal vaccines that are already commercially available, or already being manufactured, earlier in the same flu season. Typically, a rescue vaccine may be a monovalent, cell culture-based vaccine. Such vaccines may be made available weeks after regular seasonal vaccines are made available, e.g., 4 weeks, or, e.g. 8 weeks, 10 weeks, 12 weeks, 16 weeks, 20 weeks, 24 weeks. Thus, rescue vaccines may provide a solution to antigenic mismatch stemming from egg adaptation. Rescue vaccines described herein may also, or alternatively, provide a solution to antigenic mismatch stemming from antigenic drift or shift of circulating viruses (e.g. between selection of strains for vaccine production and the actual peak of disease).

A first influenza vaccine as described herein may be a vaccine comprising an antigen from a first influenza virus which has been passaged in eggs. A first influenza vaccine may be made available prior to a second influenza vaccine. A rescue vaccine as described herein may be a second influenza vaccine rescue vaccine as described herein. The second (rescue) vaccine may comprise an antigen from a second influenza virus which has not been passaged in eggs, wherein the antigen in the second influenza vaccine is more closely antigenically matched to a circulating strain than the antigen in the first influenza vaccine. The second influenza vaccine may be administered within 1 month, 2 months, 3 months, 4 months or 5 months after the first influenza vaccine. Preferably, the second influenza vaccine is administered within 3 months after the first influenza vaccine.

In some embodiments, a rescue influenza vaccine comprises an antigen prepared in host cells, wherein the antigen has greater (i.e. closer) antigenic match to antigens of circulating influenza viruses (e.g. an antigen of a circulating strain) than a seasonal influenza vaccine (e.g. a first influenza vaccine) available earlier in the same influenza season, wherein the seasonal influenza vaccine has ≤50% vaccine effectiveness against the circulating influenza virus. As will be evident to the person skilled in the art, 'host cells', as referred to herein, are not eggs. The term 'host cells' as used herein may be substituted with 'cell culture'. Preferably, the antigen prepared in host cells (cell culture) is an antigen which has not been passaged in eggs.

Accordingly, a first influenza vaccine as defined herein may have ≤50% vaccine effectiveness against the circulating influenza virus.

The invention further provides hybrid vaccines and its intermediate compositions (for example, intermediate compositions prepared during manufacture of the hybrid vaccine, prior to the final vaccine product). In essence, a hybrid vaccine can comprise at least one antigen that is produced in a non-egg-based preparation and at least one antigen that is produced in an egg-based preparation. Conventional egg-based production may be employed to manufacture antigens of strains that are not susceptible to egg adaptation or clade mismatch. In parallel but separately, one or more antigens of strains that are susceptible to egg-specific challenges are produced in egg-free system(s). A hybrid vaccine may combine such components into preferably a single formulation so as to circumvent egg-dependent antigenic mismatch.

In some embodiments, a hybrid vaccine comprises two or more components selected from the group consisting of: (i) a viral antigen from an egg-based preparation; (ii) a viral antigen from a cell culture-based preparation; (iii) a viral antigen from a recombinant protein preparation; and (iv) an RNA replicon encoding a viral antigen.

In a further aspect, the invention provides improved seed virus and related methods, for producing antigenically matched vaccines. This is based at least in part on the recognition that the presence of mixed species (e.g., quasi-species) in original isolates is likely a contributing factor to subsequent antigenic drifting. This is contrary to what has been widely considered a consequence of so-called "cell adaptation." Accordingly, the invention provides solutions to counter the source of the problem by using synthetic viruses made with defined genetic sequences. Thus, the invention provides improved seed virus, candidate vaccine virus (CVV) or reference strains, which are less susceptible to antigenic drifting than wild-type isolates.

According to the invention, a seed virus preparation described herein comprises a genetically homogeneous population of viruses, wherein an antigen of the population of viruses is synthetically derived from a genetically defined sequence. The invention also encompasses use of the seed virus preparation described herein in the manufacture of a composition. The seed virus preparation may be used to prepare or manufacture a composition, an influenza vaccine, a rescue vaccine or a hybrid vaccine, as defined herein. In related embodiments, the invention provides a vaccine made by a process comprising a step of making a seed virus preparation comprising a genetically homogeneous population of viruses, characterized in that an antigen of the population of viruses is synthetically derived from a genetically defined sequence.

It is an object of the invention to provide further and improved administration regimes which further improve protection against circulating influenza strains.

The invention also provides improved influenza vaccines and related uses and manufacturing processes for the same.

BRIEF DESCRIPTION OF THE DRAWING

FIG. 5 provides a panel of synthetic viruses generated for antigenic characterization. "Egg" or "cell" under antigen source refers to the passage history of the viruses that provided the HA and NA sequences for synthesis. In cases of mixed passage history, any passage in eggs is sufficient to trigger an "egg" designation. All synthetic test viruses were passaged exclusively in mammalian cells for these studies, regardless of the HA and NA sequences used.

FIG. 6 provides HI comparison of egg-propagated non-synthetic viruses and MDCK cell-propagated synthetic viruses with HA and NA sequences derived from egg-adapted candidate vaccine viruses.

FIG. 7 provides HI characterization of synthetic viruses with HA and NA sequences derived from egg- or mammalian-propagated wild-type viruses.

FIG. 8 provides HI titers showing antigenic mismatch between viruses with egg- and mammalian cell-derived H3N2 antigens: (A) A/Victoria/210/2009 (H3N2); and, (B) A/Victoria/361/2011 (H3N2).

FIG. 9 provides HI titers showing antigenic mismatch between viruses with egg- and mammalian cell-derived B antigens.

FIG. 10 provides Two-way HI test for the H3N2 strain A/Switzerland/9715293/2013.

FIG. 11 provides micro-neutralization assay results for mouse antisera raised against egg- and cell-derived H3N2 monobulks derived from three major clades (3C.1, 3C.2a, 3C.3a), with or without adjuvant, and tested against: (A) egg-derived A/Hong Kong/5738/2014 test virus; and (B) cell-derived A/Hong Kong/5738/2014 test virus.

DETAILED DESCRIPTION OF CERTAIN EMBODIMENTS

Figure 1:
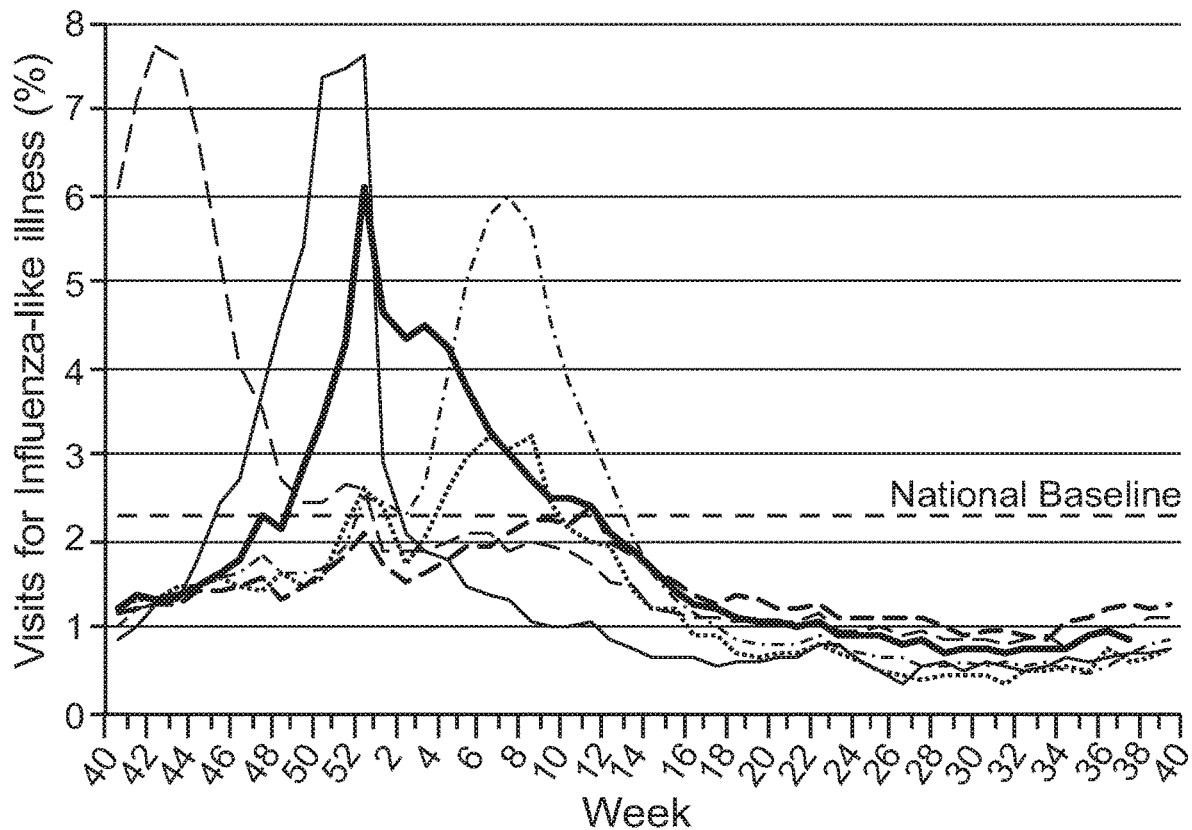
FIG. 1 provides a line graph illustrating that worst flu seasons in recent years are those where virus has evolved (i.e. those in which the virus has undergone the greatest change). Time course of hospital visits associated with flu-like illness for each of the six flu seasons is plotted over time.

The present invention is based at least in part on the recognition that seasonal influenza vaccines in certain influenza seasons lack desirable efficacy due to antigenic mismatch between a vaccine antigen and circulating strains.

Antigenic Relatedness

As used herein, the terms "match" and "mismatch," unless otherwise specified, refer to antigenic match and mismatch, respectively, between corresponding antigens of the vaccine strain (e.g., "candidate vaccine virus" or "CVV") and the circulating strain. Antigenic mismatch can result in low effectiveness of the vaccine in providing protection for vaccinated individuals. In certain seasons, for example, the efficacy may be 50% or less, e.g., between 0-50% due to antigenic mismatch (see more in Examples below). Low effectiveness may be defined as ≤50% vaccine effectiveness (or even ≤30% vaccine effectiveness) against the circulating influenza virus.

The present disclosure also refers "antigenic relatedness" or "antigenic similarity", which are used interchangeably to refer to degree of "antigenic match".

There are multiple potential sources of antigenic mismatch. First, based on timing for production of vaccines, selection needs to be made months before actual peak of disease, during which there may be antigenic drifting or shifting of circulating viruses. Second, surveillance may be incomplete, such that recommendation for vaccine strains may not reflect accurate information for circulating viruses. Third, global influenza system is very large with many agencies and processes involved, which can cause a delay in information processing. And fourth, adaptation to eggs can result in antigenic mismatch through mutations in HA, which in fact has been observed in the last several years.

Hemagglutinin (HA) is a primary antigen of influenza virus. In particular, the head region of the HA protein is the dominant antigenic region and contains key epitopes, as well as receptor binding site required for host cell entry.

Determination of antigenic match/mismatch is well established in the art. The industry standard is the hemagglutination inhibition (HI) assay, which is used as the selection basis for determining HA antigenicity and is the WHO standard assay. Standard protocol involves: antisera generation by naïve ferrets infected with virus. In essence, HI measures the ability of an immune serum to block the clumping of red blood cells caused by cross-linking of the cells by multivalent viruses with receptors for red blood cell surface antigens. Higher HI-blocking antibody titers correlate with greater neutralizing responses. In "one way" HI, sera from virus A infections are used in HI vs. virus A and virus B, while in "two way" HI, sera from virus A infection are used in HI vs. virus A and virus B, and sera from virus B infection are used in HI vs. virus A and virus B.

To further illustrate the concept of antigenic relatedness, Table 1 below provides a complete "Two way" table showing the relatedness of the following viruses: WI/05 (A/Wisconsin/67/2005); NY/04 (A/New York/55/2004); WY/03 (A/Wyoming/3/2003); and, PM/99 (A/Panama/2007/1999).

TABLE 1

Exemplary two-way HI test.

| virus | Ferret Antisera Raised Against: WI/05 | PM/99 | WY/03 | NY/04 |
|---|---|---|---|---|
| WI/05 | 2,560 | <20 | 160 | 1,280 |
| PM/99 | 1,280 | 5,120 | 1,280 | 320 |
| WY/03 | 1,280 | 1,280 | 2,560 | 1,280 |
| NY/04 | 2,560 | 20 | 640 | 2,560 |

By industry standard, viruses with fold differences in HI are considered "similar" (i.e. antigenically similar) (e.g., WY/03 and PM/99). The HI assay essentially measures (i) existence, (ii) accessibility, and (iii) immunodominance of epitopes that HA contribute to antigenicity. Thus, HI is a functional assay to determine if an antigen is likely raise an immune response and provides information on antigenic relatedness (e.g., match or mismatch). To illustrate further using Table 1 above, WI/05 can raise a response to immunodominant epitope(s) that are shared with and accessible in PM/99 (HI=1,280), while PM/99 does not raise a response to immunodominant epitopes that are shared with and accessible in WI/05 (HI≤20).

More recently, it has become evident that the HA of certain strains or clades of influenza viruses does not bind well to red blood cells. Because reliable HI assays require the ability of the HA of a virus to bind red blood cells (hemagglutination), such viruses cannot be tested by the standard HI assays.

Micro-neutralization ("MN") assay is an alternative means for characterizing the antigenicity of viruses. The MN assays may be used in place of HI assays, particularly for certain viruses that do not have HA with the ability to sufficiently bind to red blood cells, since HI assays are useful only if the HA of the virus is capable of agglutinating red blood cells. For example, certain H3N2 viruses such as 3C.2A viruses do not bind red blood cells with their HA. Thus, in some preferred embodiments, antigenic match of antigen from such viruses is determined by MN assay.

The MN assay is a highly sensitive and specific assay for detecting virus-specific neutralizing antibodies to influenza viruses in human or animal sera. (ref: WHO Global Influenza Surveillance Network: Manual for the laboratory diagnosis and virological surveillance of influenza; 2011; ISBN 978 92 4 154809 0; available at http://apps.whoint/iris/bitstream/10665/44518/1/9789241548090_eng.pdf). The MN assay is based on the assumption that serum-neutralizing antibodies to influenza viral HA will inhibit the infection of MDCK cells with virus. Serially diluted sera are pre-incubated with a standardized amount of virus before the addition of MDCK cells. After overnight incubation, the cells are fixed, and the presence of virus-infected cells is detected by an anti-influenza nucleoprotein ELISA or by plaque reduction. The absence of infectivity constitutes a positive neutralization reaction and indicates the presence of specific antibodies in the serum sample that can bind to the virus. The neutralization titer is expressed as the reciprocal of the highest dilution of sera at which virus infection is blocked. If a test serum produces a neutralization titer that is similar for two viruses, it means that the antibodies in the test sera can effectively cross-react with both viruses, suggesting that the two viruses are antigenically-related.

Thus, as explained below, a person skilled in the art may use standard assays to assess whether one influenza antigen or vaccine is more closely antigenically matched to a reference strain (e.g. a circulating strain) than another antigen or vaccine. Antigenic match may be determined using a HI assay. Alternatively, or in addition, antigenic match may be determined using a MN assay. The antigen in the second influenza vaccine is more closely antigenically matched to the circulating strain than the antigen in the first influenza vaccine if antibodies raised against the antigen in the second influenza vaccine show a higher degree of cross-reaction in the assay compared to antibodies raised against the antigen in the first influenza vaccine under identical conditions.

In some instances, antigenic mismatch may result from incorrect prediction as to what viruses are most likely to cause illness in the coming season. Viruses in the seasonal flu vaccine are selected each year based on surveillance-based forecasts about viruses, and WHO recommends specific vaccine viruses for inclusion in influenza vaccines, but then each individual country makes their own decision for which strains should be included in influenza vaccines licensed in their country. A "recommended" strain (or a "reference" strain) based on which regular seasonal influenza vaccines are produced by vaccine manufacturers, may differ from predominant strains in circulation in the flu season. In some cases, however, influenza vaccines that are manufactured in accordance with correct recommendations from WHO may still result in vaccines with low efficacy. This is in part due to a phenomenon referred to as egg adaptation. Egg adaptation may occur due to egg-specific genetic selection when a virus is propagated or grown in eggs. The virus must then adapt to the host cellular environment and genetic background, resulting in antigenic mismatch between the viral antigen prepared in the egg-based system and the corresponding antigen of circulating or recommended viruses.

Additionally or alternatively, in some circumstances, a recommended strain may not grow well in an egg-based system. Indeed, certain clades of influenza viruses are known to grow poorly in eggs. In these situations, a different but related virus, for example a virus from a different but related clade, may be selected and recommended for the manufacture of flu vaccines in order to accommodate the egg-based production of vaccines. This results in clade mismatch, which may cause antigenic mismatch.

To counter these problems, the present disclosure provides non-egg-based vaccines that enable improved antigenic match to achieve immunoprotection that egg-based vaccines may fail to provide.

Egg-Free Seed Virus

As already mentioned above, the influenza vaccine system has been developed to respond to the natural evolution of influenza viruses, but the problem of antigenic mismatch continues to be a challenge in certain years. In some years, mismatches arise naturally due to the antigenic drift of circulating viruses after vaccine strain selection has already been made. In other years, mismatches are introduced as part of the current system, which relies on the use of egg-adapted isolates as a starting material for candidate vaccine viruses. Recognition of the source of the existing problems and transforming the current process for making vaccine viruses may be of great value towards improving public health.

The use of so-called synthetic seed virus technology in vaccine manufacture has been previously described (see, for example, WO 2014/115104; WO 2013/087945; WO 2014/086732; WO 2014/141125; and WO 2014/195920). A synthetic approach can be employed for rapidly generating influenza viruses, for example, in a vaccine-approved Madin-Darby canine kidney (MDCK) cell line using novel, high-growth backbones that increase virus rescue efficiency and antigen yield (ref. 124).

The inventors of the present invention have tested the idea that this technology may also be used to produce viruses that maintain antigenic match to the intended reference viruses (e.g., matching to a circulating strain), depending on the hemagglutinin (HA) and neuraminidase (NA) sequences used for gene synthesis.

Work disclosed herein (see Examples) demonstrates general utility of this approach. Briefly, a panel of synthetic viruses was generated, using HA and NA sequences from recent isolates. As evaluated by hemagglutination inhibition tests, synthetic viruses are shown to be antigenically similar to the conventional egg- or cell-propagated reference strains. Importantly, there is no impact of the novel backbones on antigenicity, suggesting that this synthetic approach is generally suitable for producing better-matched virus candidates efficiently for both egg- and cell-based vaccine manufacturing platforms. When combined with cell culture technology for antigen production, synthetic viruses generated using HA and NA sequences from a non-egg-adapted prototype can help to reduce the antigenic mismatch issues that plague current seasonal influenza vaccines. The synthetic seed virus approach described herein is particularly suitable for certain clades/strains that are susceptible for adaptation and hence antigenic drifting.

As further detailed herein, for example, wild-type 3C.2A viruses maintained in cell culture show HA and/or NA mutations, which can change receptor binding properties on host cells or red blood cells (RBCs). Such mutations have been to date considered as cell adaptation (see for example, Chambers et al. (2014) J Virol. 88(18): 10986-9; Lee et al. (2013) PLoS One 8(11): e79252; and Mohr et al. (2015) Virol J. 12:67).

Unexpectedly, however, data presented herein point to a distinct source of the problem and indicate instead that the presence of mixed species in the original isolates is likely an important contributor to subsequent antigenic drifting. The inventors have found that the use of synthetic viruses made with a defined sequence can circumvent similar changes previously considered as adaptation to host cell environment (e.g., cell adaptation). Furthermore, data presented herein support that certain synthetic backbones can be reliably employed to achieve high HA titers. Thus, the invention provides improved seed virus, candidate vaccine virus (CVV) or reference strains, which are less susceptible to antigenic drifting than wild-type isolates.

Accordingly, in one aspect, the invention encompasses improved candidate vaccine viruses and related methods of producing candidate vaccine viruses using synthetic seed virus.

Synthetic seed virus technology may be used to obtain a genetically homogenous preparation of seed virus, which can be used to produce a vaccine (e.g. a vaccine as defined herein). Thus, the invention also includes improved seed viruses passaged in non-egg-based host system(s), such as a cell culture. Suitable cell cultures include eukaryotic cells, such as mammalian cells, insect cells, avian cells, etc. (as discussed further herein). Such synthetic seed viruses are characterized in that they are genetically stable and typically grow to higher titers than viruses passaged in eggs. Genetic stability as used herein refers to resistance to mutations/adaptation after several rounds of passaging in cell culture, e.g., 2, 3, 4, 5, or 6 passages. Such seed viruses are further characterized in that each preparation consists of a genetically homogeneous population of viruses (as opposed to mixed (i.e., heterogeneous) sub-populations, which may be the case in conventional seed virus preparations). As used herein, synthetic seed virus preparations may be determined to be genetically homogeneous based on DNA Sanger Sequencing (but not necessarily Next Generation Deep Sequencing). A genetically homogeneous synthetic seed virus preparation may not be 100% genetically 'pure'. Indeed, a single round of passaging in cells may lead to a small amount of sequence diversification. Thus, a genetically homogeneous synthetic seed virus preparation may contain a small proportion (e.g. less than 10%, more preferably less than 5%, 3% or 1%) of synthetic virus that is not genetically identical to the predominant synthetic virus in the population.

Accordingly, the invention includes a method for manufacturing a vaccine (which may be an influenza vaccine for use according to the present invention), comprising a step of preparing a synthetic seed virus in an egg-free process, wherein the synthetic seed virus is not passaged in eggs. In preferred embodiments, an antigen prepared from the synthetic seed virus (which may be an antigen of a second influenza vaccine, as defined herein) is more closely antigenically matched to a reference strain (e.g. a circulating strain), as compared to an antigen from an egg-based counterpart (e.g. a first influenza vaccine, as defined herein). In particularly useful embodiments, the synthetic seed virus is isolated from a strain that (i) is susceptible to egg-adaptation; and/or (ii) has an HA that does not bind well to red blood cells. The expression "does not bind well to red blood cells" means that the HA of that particular viral strain/clade has poor affinity for red blood cells such that it renders the standard HI assay unreliable.

In some embodiments, the vaccine comprises an antigen from H3N2 and/or B strain(s). In some embodiments, the antigen is HA, NA, or combination thereof.

The invention thus provides a seed virus preparation comprising a genetically homogenous population of viruses, characterized in that HA of the genetically homogeneous population of viruses is synthetically prepared from a genetically defined sequence. The invention also encompasses use of the seed virus preparation in the manufacture of a composition. In related embodiments, the invention provides a vaccine made by a process comprising a step of making a seed virus preparation comprising a genetically homogenous population of viruses, characterized in that an antigen of the genetically homogenous population of viruses is synthetically prepared from a genetically defined sequence. In preferred embodiments, the antigen is HA, NA, or combination thereof. In some embodiments, the vaccine is manufactured in an egg-free process, such that the virus is never passaged in eggs through the entire vaccine manufacture process. The genetically defined sequence may, for example, be a HA sequence of a cell-based isolate, which may be an isolate as described herein.

Accordingly, synthetic seed virus, as described above, may be used for the manufacture of a composition, a second influenza virus vaccine, a rescue vaccine or a hybrid vaccine, as defined herein. The synthetic seed virus for use in the invention may be manufactured in an egg-free process, and may not have been passaged in eggs. Preferably, the synthetic seed virus is grown in cell culture.

The synthetic seed virus may be generated using HA and NA sequences from an isolate of a reference influenza virus strain (e.g. a circulating virus strain). In preferred embodiments, the isolate is not egg-adapted. Further, the isolate is preferably isolated in cell culture (e.g. in mammalian cell lines qualified for vaccine production). The isolate may not be a high-growth egg-based reassortant.

The isolate is preferably an isolate of a circulating strain. For example, the isolate may be included in a list of the predominant circulating influenza strains for a given influenza season (e.g. a list published by the WHO and/or the FDA). The isolate may be isolated from clinical samples by one or more World Health Organization (WHO) National Influenza Centers.

The isolate may be an isolate of a clade or strain that is susceptible to egg adaptation and/or to clade mismatch.

A synthetic seed virus is typically prepared using reverse genetics techniques as described herein. For example, the virus may be prepared using a viral backbone comprising a set of viral genome segments encoding influenza virus proteins (other than HA and NA). Where a synthetic seed virus is an A strain virus (e.g. H3N2 virus), the synthetic seed virus may be prepared using a backbone selected from PR8, PR8x, #19, and #21. In some preferred embodiments, the strain is an H3N2 strain and the backbone is PR8x. Where the synthetic seed virus is a B strain virus (e.g. a strain from the B/Victoria lineage), the synthetic seed virus may be prepared using a backbone including all six backbone segments from B/Brisbane/60/2008.

Rescue Vaccines

In another aspect, the present invention provides such vaccines referred to herein as the rescue vaccine. A rescue vaccine may be manufactured as a corrective measure to supplement a regular seasonal vaccine that has been shown to lack desired effectiveness, e.g., within the same flu season. Thus, regular seasonal vaccines may be produced conventionally in accordance with WHO recommendation and are commercially made available for vaccination. Subsequently, if such regular vaccines are observed or determined to be poorly effective, e.g., 50% VE (vaccine effectiveness) or less, due to antigenic mismatch, a rescue vaccine may be produced as a follow-up measure within the same flu season in non-egg-based preparation, which would provide better antigenic match to circulating viruses. Therefore, it is envisaged that rescue vaccines are prepared or propagated without eggs.

In some embodiments, a rescue vaccine comprises (a) an antigen produced in a cell culture-based preparation, such as avian cell cultures and mammalian cell cultures; (b) a recombinant protein-based antigen; (c) an RNA replicon (e.g., self-amplifying RNA) encoding an antigen. In some embodiments, a rescue vaccine comprises any combinations thereof. The rescue vaccine may comprise one, more than one, or all of (a), (b) and (c). The recombinant protein-based antigen may be a recombinantly expressed antigen. According to the present invention, the antigen is an influenza antigen.

As indicated above, the invention provides a rescue influenza vaccine comprising an antigen prepared in host cells, wherein the antigen has greater (i.e. closer) antigenic match to antigens of circulating influenza viruses (e.g. an antigen of a circulating strain) than a seasonal influenza vaccine available earlier in the same influenza season, wherein the seasonal influenza vaccine has ≤50% vaccine effectiveness against the circulating influenza viruses. The antigen may be an antigen, as described herein, which has not been passaged in eggs. The seasonal influenza vaccine may be a first influenza vaccine as described herein.

As discussed above, synthetic seed virus may be used to produce a rescue vaccine of the present invention. The synthetic seed virus may be a synthetic seed virus provided herein. The preparation of synthetic seeds can be faster, allowing temporal adjustments. Furthermore, the use of the synthetic seed virus technology enables a genetically homogenous preparation of seed virus, which may contribute to genetic stability. By contrast, conventional seed virus preparations may contain genetically heterogeneous (e.g., mixed) populations of viral sequences, which may over time (e.g., through passage) shift towards certain subpopulation (s) being more dominant. In such an event, the resulting subpopulation that is predominant in the seed virus preparation may differ from the original subpopulation that is predominant in the reference strain.

A rescue vaccine of the present invention may be a monovalent influenza vaccine. In some embodiments, a regular seasonal vaccine (typically trivalent or quadrivalent) may show that the antigen of one of the strains included in such product is antigenically mismatched. Subsequently, a monovalent rescue vaccine can be produced, which provides a matched antigen, and made available to provide immuno-protection within the same flu season. In the event that a regular seasonal vaccine (typically trivalent or quadrivalent) shows that the antigens of more than one strains included in such product are antigenically mismatched relative to circulating viruses, then, a rescue vaccine may be produced to include more than one matched antigens accordingly. Thus, the rescue vaccine may, for example, be a bivalent rescue vaccine. Similarly, in the event that a regular seasonal vaccine (typically trivalent or quadrivalent) shows that the antigens of one (or more) strain(s) included in such product is/are antigenically mismatched relative to a circulating virus, then, a rescue vaccine may be produced to include one (or more) matched antigen(s) accordingly. Thus, the rescue vaccine may be a monovalent rescue vaccine.

A rescue vaccine of the present invention may be un-adjuvanted or adjuvanted. For an adjuvanted rescue vaccine, in some embodiments, the rescue vaccine may require low dose antigen. "Low dose" in this context means that the amount of antigen per dose that is required to elicit a statistically acceptable immune response in subjects is less than standard amounts. Typically, standard seasonal influenza vaccines contain about 15 μg of HA per strain in each dosage form. Thus, "low dose" vaccines may contain less than about 15 μg of HA per strain, e.g., about 12 μg, about 9 μg, about 7.5 μg, about 5 μg, about 3.75 μg. In some embodiments, an adjuvanted rescue vaccine may provide a faster immune response in subjects, as compared to an un-adjuvanted rescue vaccine containing otherwise the same components. In situations where a rescue vaccine may still contain a degree of antigenic mismatch (albeit lesser degree than an egg-based vaccines), such rescue vaccine may be adjuvanted, so as to allow broader immune protection in patients despite less-than-perfect antigenic match (e.g., cross protection). Overall, an adjuvant may generate a more robust response and increase overall titers to dominant and sub-dominant epitopes.

Adjuvanted rescue vaccine may thus provide a faster immune response in subjects, as compared to an un-adjuvanted rescue vaccine containing otherwise the same components, and may in addition provide antigen sparing effects. In some preferred embodiments, the rescue vaccine (or the second influenza vaccine, as defined herein) is adjuvanted, particularly where it contains an antigen with a degree of antigenic mismatch compared to the circulating strain. A degree of mismatch may, for example, be indicated by a 4-fold, 3-fold, 2-fold or 1-fold difference in HI or a 2-fold or 1-fold difference in MN titer against the circulating strain compared to the homologous virus titer.

A rescue vaccine of the present invention is suitable for immunizing a human subject who has been previously administered a regular seasonal flu vaccine earlier in the flu season. A rescue vaccine of the present invention is suitable for immunizing a human subject who has not been administered with a regular seasonal flu vaccine earlier in the flu season. A rescue vaccine may be used to immunize healthy subjects, subjects at risk, and/or immunocompromised subjects. A rescue vaccine may be used to immunize subjects of various age groups, including the elderly and pediatric populations. Suitable age groups are described further herein.

Hybrid Vaccines

In another aspect, the present invention provides hybrid vaccines, and any intermediate compositions that may be utilized to produce the same. As used herein, a "hybrid vaccine" refers to a vaccine composition that contains two or more antigens of different production means (e.g., sources or systems). For example, a "hybrid vaccine" may contain two or more antigens produced from different production platforms. Thus, a hybrid vaccine may contain any combinations of: one or more egg-based antigen(s), one or more cell culture-based antigen(s), one or more recombinant protein antigen(s), one or more RNA replicon(s), etc. Preferably, such antigens are provided as a single formulation suitable for administration in human subjects. In certain embodiments, however, a full panel of desired antigens may be administered as multiple formulations. For example, at least one of the multiple formulations may be a rescue vaccine (see above). According to the present invention, the antigen is an influenza antigen.

According to the present invention, a hybrid vaccine may be produced to include an antigen prepared in an egg-free process. The egg-free process may be a cell culture, recombinant expression system, an in vitro transcription of RNA replicon, etc. This may be particularly suitable when one or more of the virus strains predicted to be illness-causing viruses in circulation are those known to be susceptible to egg adaptation and/or when a certain clade is known to grow poorly in eggs. This may also be particularly suitable when HA from a certain clade or strain does not bind to red blood cells and/or is not capable of agglutinating red blood cells (e.g. in an HI assay). In some embodiments, such virus strain is or comprises H3N2. Alternatively or additionally, such virus clade is or comprises Clade 3C.3A or Clade 3C.2A. Further examples of such strains or clades are described herein.

In some embodiments, an egg-adapted version of a clade results in antigenic mismatch, while a cell version results in greater antigenic match. In some embodiments, egg adaptation results in antigenic mismatch through a change in glycosylation pattern on the head region of HA, such as a glycosylation loss, while the glycosylation pattern relevant to antigenicity in cell version is preserved, thus maintaining antigenic match. Relevant glycosylation sites are those contributing to the antigenicity of the antigen, e.g., affecting the presence, accessibility and/or immunodominance of an epitope. For example, Clade 3C.2A may lose key HA sugars upon egg adaptation, which may accompany antigenic mismatch. Certain B strains have been reported to lose key HA sugars upon egg adaptation, leading to possible antigenic mismatch (see, for example, ref. 119). Antigenic mismatch and greater antigenic match may be determined by HI or MN, as described herein (for example, by >4-fold difference in HI titer against the circulating strain and ≤4-fold difference in HI titer against the circulating strain, respectively, compared to the homologous virus titer).

The present invention contemplates that when one or more strains predicted to be disease-causing in an upcoming season are considered to be poor candidates for egg-based production to achieve antigenic match, such strain(s) be produced in egg-free system, such that antigenic match can be achieved in resulting vaccines. In some embodiments, therefore, one or more antigens produced by egg-free process(es) may be optionally combined with one or more antigens produced in eggs. Accordingly, the invention provides a composition comprising an antigen produced without eggs, which may be an intermediate component to be combined with additional antigen(s) to produce a formulation (e.g., hybrid vaccine) comprising two or more antigens from two or more sources of production methods (e.g., egg-based; cell culture-based, recombinant, RNA replicon, etc.).

Accordingly, a hybrid vaccine of the invention may comprise two or more components selected from the group consisting of: (i) a viral antigen from an egg-based preparation; (ii) a viral antigen from a cell culture-based preparation; (iii) a viral antigen from a recombinant protein preparation; and (iv) an RNA replicon encoding a viral antigen. The viral antigen may be an influenza antigen. The hybrid vaccine may be trivalent or quadrivalent. The hybrid vaccine may further comprise an adjuvant. The cell culture-based preparation may be a mammalian or avian cell-based preparation. 'Cell culture-based preparation' refers to antigen grown in cell culture.

The viral antigen (i) from an egg-based preparation may be a viral antigen which has been passaged in eggs. The viral antigen prepared in an egg-free process may be antigen from a cell culture-based preparation, viral antigen from a recombinant protein preparation and/or viral antigen encoded (in vitro) by a RNA replicon. Typically, viral antigen (i) from an egg-based preparation will be from a strain or clade which is not, as described herein, susceptible to egg adaptation and/or to clade mismatch. In preferred embodiments, the viral antigen prepared in an egg-free process ((ii), (iii) and/or (iv)) is antigen from a strain or clade, as described herein, which is susceptible to egg adaptation and/or to clade mismatch. Alternatively or additionally, the viral antigen prepared in an egg-free process is antigen from a strain or clade which does not bind to red blood cells and/or is not capable of agglutinating red blood cells (e.g. in an HI assay), as described herein. In hybrid vaccines described herein, the viral antigen prepared in an egg-free process may be an influenza antigen (e.g. in a second influenza vaccine or a rescue vaccine) and is preferably more closely antigenically matched to a circulating influenza strain than the corresponding antigen in a reference vaccine. The reference vaccine may be a first influenza vaccine as defined herein, and/or may have been passaged in eggs. The reference vaccine may, for example, be a vaccine made available earlier in a given influenza season. Relative degree of antigenic match may be determined as described herein (e.g. by HI and/or MN assay). Alternatively, or in addition, an antigen from an egg-based preparation (e.g. an egg-adapted clade or strain), as used in a vaccine described herein, may exhibit ≤50% vaccine effectiveness against the circulating strain and an antigen grown in cell culture (which, optionally, has not been passaged in eggs) may exhibit >50% vaccine effectiveness.

Immunization Methods

The invention aims to overcome existing antigenic mismatch problems by providing vaccination regimes, in which vaccination with a first influenza vaccine comprising an antigen from a first influenza virus, which has been passaged in eggs, is followed by vaccination with a second influenza vaccine comprising antigens from an influenza virus, which has been grown in cell culture. By using a second vaccine that is more closely antigenically matched to a human circulating influenza strain, the methods of the invention provide better protection against influenza, especially in situations where the efficacy of the regular seasonal vaccine is sub-optimal due to the inclusion of a mismatched influenza strain.

The invention thus provides a method for immunizing a human, comprising steps of (a) administering to the human a first influenza vaccine comprising an antigen from a first influenza virus which has been passaged in eggs; and subsequently (b) administering to the same human a second influenza vaccine comprising an antigen from a second influenza virus which has been grown in cell culture, wherein the antigen in the second influenza vaccine is more closely antigenically matched to a circulating influenza strain than the antigen in the first influenza vaccine.

Also provided is a method for immunizing a human who has previously been administered a first influenza vaccine comprising an antigen from a first influenza virus which has been passaged in eggs, comprising administering to the same human a second influenza vaccine comprising an antigen from a second influenza virus which has been grown in cell culture, wherein the antigen in the second influenza vaccine is more closely antigenically matched to a circulating strain than the antigen in the first influenza vaccine. Alternatively, or in addition, the antigen from the second influenza virus may not have been passaged in eggs.

The invention also provides a first influenza vaccine comprising an antigen from a first influenza virus which has been passaged in eggs and a second influenza vaccine comprising an antigen from a second influenza virus which has been grown in cell culture, for use in immunizing a human by the method of any preceding claim.

Further provided is a first influenza vaccine comprising an antigen from a first influenza virus which has been passaged in eggs for pre-immunizing a human who will receive a second influenza vaccine comprising an antigen from a second influenza virus which has been grown in cell culture, wherein the antigen in the second influenza vaccine is more closely antigenically matched to a circulating strain than the antigen in the first influenza vaccine.

Also provided is a second influenza vaccine comprising an antigen from a second influenza virus which has not been passaged in eggs (e.g. which has been grown in cell culture) for use in immunizing a human who has previously received a first influenza vaccine which has been passaged in eggs, wherein the antigen in the second influenza vaccine is more closely antigenically matched to a circulating strain than the antigen in the first influenza vaccine.

The two influenza vaccines are administered within the same influenza season. The second influenza vaccine may be administered 1 month, 2 months, 3 months, 4 months or 5 months after the first influenza vaccine. Preferably, the second influenza vaccine is administered within 3 months after the first influenza vaccine.

The invention also provides a kit comprising: (i) a first influenza vaccine comprising an antigen from a first influenza virus which has been passaged in eggs; and (ii) a second influenza vaccine comprising an antigen from a second influenza virus which was grown in cell culture, wherein the antigen in the second influenza vaccine is more closely antigenically matched to a circulating strain than the antigen in the first influenza vaccine. The kit may comprise instructions for the use of the kit in the methods of the invention.

The Influenza Strain

The current process for preparing seasonal vaccines against human influenza virus infection involves the following steps (refs. 1 & 2): (a) isolation of circulating virus strains; (b) antigenic and genetic analysis of isolated viruses; (c) selection of viral strains for use during the coming season; (d) preparation of high-growth seed strains (i.e. CVVs) by reassortment or the use of reverse genetics (or by passage in eggs or cell culture, e.g. for B virus prototype strains that do not require reassortment, as referred to below); (e) release of seed strains (CVVs) to vaccine manufacturers; (f) evaluation by the manufacturers of the strains' suitability for industrial production; and (g) growth of the seed strains (i.e. passage and expansion of the CVVs) to produce virus (i.e. seed virus stocks) from which vaccines are then manufactured.

Steps (a) to (e) of this process are performed by the FDA and government-approved international influenza centres, typically under the auspices of the World Health Organization (WHO); steps (f) and (g) are performed by the manufacturers themselves.

Steps (d) and (g) transition a virus from one that is naturally adapted for infecting humans into one that will grow to high titers under industrial growth conditions. For influenza A virus, step (d) typically involves creating a 6:2 reassortant strain that includes the HA and NA encoding genome segments from the strains selected in (c) and the remaining six genome segments from a strain that grows efficiently in chicken eggs, and this strain is usually A/PR/

8/34. The reassortment procedure is then followed by repeated passaging of the strain in embryonated eggs to allow for egg adaptation and growth enhancement. For influenza B virus, prototype strains with good growth characteristics are usually obtained by direct and repeated passaging in embryonated eggs without attempting to generate reassortants. In some cases, step (d) may instead involve creating a non-6:2 reassortant, for example a 5:3 or a 4:4 reassortant.

Thus the steps performed prior to release to vaccine manufacturers involve passaging influenza virus through eggs. Even if the viruses are grown by a manufacturer in step (g) on a cell substrate, rather than on eggs, the virus will still have been passaged through eggs at some stage between isolation in step (a) and receipt by a manufacturer in step (e).

Where an antigen is from an influenza virus which has been grown in cell culture or eggs, this generally refers to the growth in step (g). Thus, an antigen from an influenza virus which has been grown in eggs or cell culture refers to an antigen that was prepared from an influenza virus that was harvested from eggs or cell culture, respectively. For example, where the antigen is from an influenza virus grown in eggs, the influenza virus will have been grown in eggs, the influenza virus will have been harvested from the eggs and the antigen would have been prepared from the harvested influenza virus. In contrast, where a virus has been passaged in eggs, the influenza virus can have been grown in eggs at any stage during the production process, i.e. at any stage during the production process. Typically, there would be additional culture steps though after the egg passaging and these additional culture steps can be carried out in eggs or cell culture.

The step of passaging in eggs is deemed of particular importance by the authorities. For example, the 2003/04 influenza season in the northern hemisphere was dominated by the A/Fujian/411/2002-like variant, but the vaccine strain being used contained the H3N2 from the previous year (A/Panama/2007/1999). This strain was a poor antigenic match to the Fujian strain, which led to reduced vaccine effectiveness. The Fujian strain had been rejected by the U.S. Food and Drug Administration (FDA) because it had not been passaged in eggs (refs. 2 & 3), and no antigenically-similar egg-isolated strains were available.

In order to provide an efficacious influenza vaccine, the influenza strains found in vaccines need to be matched as closely as possible to the circulating influenza strain. Authorities like the WHO and the FDA publish a list of the predominant circulating influenza strains each year and further publish recommended influenza strains for inclusion in influenza vaccines, or reference strains to guide selection of the strains for inclusion in influenza vaccines.

The influenza antigens used in the first and second influenza vaccines of the invention are matched to a circulating strain. This is necessary in order to allow them to elicit an immune response against said influenza strain. The influenza antigen in the second influenza vaccine will generally provide a closer antigenic match to a circulating influenza strain than the influenza antigen in the first influenza vaccine.

Influenza antigens which are antigenically matched generally come from influenza strains which belong to the same influenza subtype (for example H1N1, H3N2 or H5N1) and are antigenically similar. Whether two influenza antigens are antigenically matched can be easily determined, for example using a hemagglutinin inhibition (HI) assay. In particular, two influenza antigens will be considered antigenically matched if they show a high degree of cross-reaction in a HI assay (e.g., less than fourfold titer).

The influenza antigen in the second influenza vaccine is matched more closely to a circulating strain than the influenza antigen in the first influenza vaccine. Again, this can easily be determined by a person skilled in the art through standard assays, like the HI assay. Alternatively, or in addition, the MN assay may be used.

For example, in order to assess whether the second influenza antigen is more closely antigenically matched to a circulating strain, non-human animals (such as ferrets or mice) are either infected with a live virus or injected with either the first or the second influenza antigen. After a time sufficient to develop antibodies against the influenza antigen, blood is extracted from the non-human animals, serum is prepared and subjected to serial dilution (for example a series of 1:10, 1:20, 1:40, 1:80, 1:160, 1:320, 1:640, 1:1280, 1:2560, 1:5120, 1:10240 and 1:20480). Equal volumes of each dilution point are then combined with red blood cells and a circulating influenza strain, wherein the final concentration of red blood cells and the circulating influenza strain is the same for each dilution. The reactions are then carefully monitored for hemagglutination. The higher the dilution at which the antibody can still inhibit hemagglutination the better the antigen can be considered matched to the circulating strain. Thus, by comparing the highest dilution at which antibodies to the first and the second influenza antigen can still inhibit hemagglutination one can determine which antigen is matched more closely to a circulating strain.

Antigenic match may be assessed by infecting the non-human animal with live virus (the first or second virus) which contains the antigen of interest (e.g. the first or second influenza antigen). For example, the live virus may be the seed virus strain from which the first or second influenza vaccine may be manufactured.

The antigen in the second influenza vaccine is more closely antigenically matched to a circulating strain than the antigen in the first influenza vaccine if antibodies raised against the antigen in the second influenza vaccine show a higher degree of cross-reaction in an HI assay compared to antibodies raised against the antigen in the first influenza vaccine under identical conditions. In particular, the antigen in the second influenza vaccine is more closely antigenically matched to a circulating strain than the antigen in the first influenza vaccine if the highest dilution at which antibodies raised against the antigen in the second influenza vaccine can inhibit hemagglutination is higher compared to the highest dilution at which antibodies raised against the first antigen can inhibit hemagglutination, using an HI assay under identical conditions. For example, if an antibody raised against the second influenza antigen can inhibit hemagglutination up to a dilution of 1:2560 whilst the antibody against the first influenza antigen can inhibit hemagglutination only up to a dilution of 1:1280, the second influenza antigen will be considered to be matched more closely antigenically. It is understood that "identical" in this context means that all conditions are identical except the antibody which is used in the assay as this antibody will have been raised against the individual antigens.

In a preferred, example, the antigen in the second influenza vaccine is more closely antigenically matched to a circulating strain than the antigen in the first influenza vaccine if the highest dilution at which antibodies raised against the antigen in the second influenza vaccine can inhibit hemagglutination by the circulating strain is closer to the highest dilution at which antibodies raised against the circulating strain can inhibit hemagglutination by the circulating strain (i.e. closer to the homologous virus titer), than the highest dilution at which antibodies raised against the antigen in the first influenza vaccine can inhibit hemagglutination by the circulating strain, under identical conditions.

The antigen in the second influenza vaccine may, for example, show ≤4-fold difference in HI titer against the circulating strain compared to the homologous virus titer. In some preferred embodiments, the antigen in the second influenza vaccine will show less than 4-fold difference (e.g. ≤3-fold, ≤2-fold, ≤1-fold difference) in HI titer against the circulating strain compared to the homologous virus titer. In further preferred embodiments, the antigen in the second influenza vaccine will show ≤2-fold difference in HI titer against the circulating strain compared to the homologous virus titer.

The antigen in the first influenza vaccine may, for example, show >4-fold difference in HI titer against the circulating strain compared to the homologous virus titer.

Alternatively, or in addition, the antigen in the second influenza vaccine is more closely antigenically matched to a circulating strain than the antigen in the first influenza vaccine if the MN neutralization titer against the circulating strain for antibodies raised against the antigen in the second influenza vaccine is closer to the homologous MN titer than the MN neutralization titer against the circulating strain for antibodies raised against the antigen in the first influenza vaccine, under identical conditions.

The antigen in the second influenza vaccine may, for example, show ≤2-fold difference in MN titer against the circulating strain compared to the homologous MN titer.

The antigen in the first influenza vaccine may show >2-fold difference in MN titer against the circulating strain compared to the homologous MN titer.

Thus, an antigen in a second influenza vaccine may show a higher degree of cross-reaction in an HI assay (e.g. a two-way HI test) and/or an MN assay, when compared to a circulating strain, than an antigen in a first influenza vaccine when compared to the circulating strain in said assay(s).

The second influenza vaccine may be a rescue vaccine, hybrid vaccine or composition as described herein. The first influenza vaccine may be a seasonal influenza vaccine.

The first and second influenza vaccines may comprise antigen from a strain which is susceptible to egg adaptation and/or to clade mismatch.

A virus strain or clade that is susceptible to egg adaptation and/or to clade mismatch, as referred to herein, may be a H3N2 strain. The clade may be Clade 3C.2A (A/Hong Kong/5738/2014-like or A/Hong Kong/4801/2014-like), Clade 3C.3A (e.g. A/Switzerland/9715293/2013-like), or 3C.1 (e.g. A/Texas/50/2012-like virus isolate). Alternatively, or in addition, the virus strain or clade that is susceptible to egg adaptation and/or to clade mismatch may be a B strain, for example a strain from the B-Victoria lineage (e.g. B/Brisbane/60/2008-like). One of ordinary skill in the art can readily identify a strain or clade that is susceptible to egg adaptation and/or to clade mismatch. For example, passaging an isolate of such a strain in eggs may result in virus which is less closely antigenically matched compared to the original isolate and/or circulating strain. In contrast, when the isolate is passaged in mammalian cells, such mismatch in the resulting virus is not observed (or is not observed to the same degree).

The circulating strain can be a seasonal circulating strain. Influenza virus strains for use in seasonal vaccines change from season to season. As discussed above, the authorities publish lists of the circulating influenza strains each year and so a skilled person is aware of these.

The circulating strain may also be a pandemic influenza strain (i.e. a strain to which the vaccine recipient and the general human population are immunologically naïve), such as H2, H5, H7 or H9 subtype strains (in particular of influenza A virus).

The antigen in the second influenza vaccine is from the same influenza subtype as an antigen in the first influenza vaccine which has been passaged in eggs. For example, where the first influenza vaccine comprises antigens from a H1 strain, a H3 strain and an influenza B strain and all three have been passaged in eggs, the influenza antigen in the second influenza vaccine may be from a H1 strain, a H3 strain or an influenza B strain. Likewise, where the first influenza vaccine is a monovalent H1 influenza vaccine, the antigen in the second influenza vaccine will also be of the H1 subtype.

Where only some of the influenza antigens in the first influenza vaccine have been prepared from an influenza virus which has been passaged in eggs, then the antigen in the second influenza vaccine will be of the same subtype as those strains. For example, where only the H1 and H3 strains in a trivalent influenza vaccine were passaged in eggs, the antigen in the second influenza vaccine may contain one or both of an influenza antigen from a H1 strain and/or a H3 strain.

It will be understood that the antigen in the first influenza vaccine and the antigen in the second influenza vaccine which are assessed for their antigenic match to a circulating strain will be of the same influenza subtype.

Vaccines

Various forms of influenza virus vaccine are currently available, and vaccines are generally based either on live virus or on inactivated virus. Inactivated vaccines may be based on whole virions, split virions, or on purified subunit (e.g., purified surface) antigens. Influenza antigens can also be presented in the form of virosomes. The invention can be used with any of these types of vaccine, but will typically be used with inactivated vaccines.

The antigen may take the form of a live virus or an inactivated virus. Chemical means for inactivating a virus include treatment with an effective amount of one or more of the following agents: detergents, formaldehyde, formalin, β propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. The INFLEXAL™ product is a whole virion inactivated vaccine.

Where an inactivated virus is used, the vaccine may comprise whole virion, split virion, or purified surface antigens (including hemagglutinin and, usually, also including neuraminidase).

Virions can be harvested from virus containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating virions with detergents or solvents (e.g. ethyl ether, polysorbate 80, deoxycholate, tri-N-butyl phosphate, Triton-X-100, Triton N101, cetyltrimethylammonium bromide, etc.) to produce subvirion preparations, including the Tween-ether splitting process. Methods of splitting influenza viruses are well known in the art (e.g., see refs. 4-9, etc.). Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g., cationic) surfactants, e.g., alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g., the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g., in a sucrose density gradient solution). Split virions can usefully be resuspended in sodium phosphate-buffered isotonic sodium chloride solution. The AFLURIA™, BEGRIVAC™, FLUARIX™, FLUZONE™ and FLUSHIELD™ products are split vaccines.

Purified surface antigen (or purified subunit) vaccines comprise the influenza surface antigens hemagglutinin and may also include neuraminidase. Processes for preparing these proteins in purified form are well known in the art. The FLUVIRIN™, AGRIPPAL™, FLUCELVAX™, FLUAD™ and INFLUVAC™ products are subunit vaccines.

Other strains that can usefully be included in the compositions are strains which are resistant to antiviral therapy (e.g., resistant to oseltamivir (ref. 10) and/or zanamivir), including resistant pandemic strains (ref. 11).

The influenza virus may be attenuated. The influenza virus may be temperature-sensitive. The influenza virus may be cold adapted. These three possibilities apply in particular for live viruses.

The first influenza vaccine can be a trivalent influenza vaccine. The first influenza vaccine can also be a tetravalent influenza vaccine. Such tetravalent influenza vaccines frequently contain two influenza A and two influenza B strains and have the advantage that they can include two different lineages of influenza B viruses. Such vaccines can therefore offer broader protection against circulating influenza viruses. The first influenza vaccine may also include antigen (s) from one, two, five, six or more influenza strains, including influenza A virus and/or influenza B virus. Where a vaccine includes more than one strain of influenza, the different strains are typically grown separately and are mixed after the viruses have been harvested and antigens have been prepared.

At least one of the influenza antigens in the first vaccine will have been prepared from an influenza virus that has been passaged in eggs. Human influenza viruses bind to receptor oligosaccharides having a Sia(α2,6)Gal terminal disaccharide (sialic acid linked α 2,6 to galactose), but eggs instead have receptor oligosaccharides with a Sia(α2,3)Gal terminal disaccharide. Growth of human influenza viruses in eggs thus provides selection pressure on hemagglutinin away from Sia(α2,6)Gal binding towards Sia(α2,3)Gal binding. Influenza viruses which have been passaged in eggs can therefore be identified in that they have a binding preference for oligosaccharides with a Sia(α2,3)Gal terminal disaccharide compared to oligosaccharides with a Sia (α2,6)Gal terminal disaccharide.

To determine if a virus has a binding preference for oligosaccharides with a Sia(α2,3)Gal terminal disaccharide compared to oligosaccharides with a Sia(α2,6)Gal terminal disaccharide, various assays can be used. For instance, reference 12 describes a solid-phase enzyme-linked assay for influenza virus receptor-binding activity which gives sensitive and quantitative measurements of affinity constants. Reference 13 used a solid phase assay in which binding of viruses to two different sialylglycoproteins was assessed (ovomucoid, with Sia(α2,3)Gal determinants; and pig α2 macroglobulin, which Sia(α2,6)Gal determinants), and also describes an assay in which the binding of virus was assessed against two receptor analogs: free sialic acid (Neu5Ac) and 3' sialyllactose (Neu5Acα2-3Galβ1-4Glc). Reference 14 reports an assay using a glycan array which was able to clearly differentiate receptor preferences for α2,3 or α2,6 linkages. Reference 15 reports an assay based on agglutination of human erythrocytes enzymatically modified to contain either Sia(α2,6)Gal or Sia(α2,3)Gal. Depending on the type of assay, it may be performed directly with the virus itself, or can be performed indirectly with hemagglutinin purified from the virus.

Where the first influenza vaccine is a multivalent influenza vaccine, all of the influenza antigens in the vaccine will usually have been prepared from influenza viruses that have been passaged in eggs. However, the invention can also be practiced with a first influenza vaccine in which one, two, three, four, five, six or more influenza antigens are prepared from influenza viruses that were passaged in eggs.

The first influenza vaccine may also comprise antigens from an influenza virus which has been prepared from influenza viruses grown in eggs. This means that the influenza virus from which the antigen in the vaccine is prepared was grown in eggs.

In contrast, where a virus was merely passaged in eggs, it may have been grown in eggs originally and then transferred to cell culture so that the influenza virus from which the influenza antigen is finally prepared was grown in cell culture. Such viruses will retain their binding preference for oligosaccharides with a Sia(α2,3)Gal terminal disaccharide compared to oligosaccharides with a Sia(α2,6)Gal terminal disaccharide and so the methods of the invention will still be beneficial for the efficacy of such vaccines.

In some preferred embodiments, the antigens in the second influenza vaccine are prepared from an influenza virus grown in cell culture. Growing influenza viruses in cell culture can avoid the selection pressure on hemagglutinin away from Sia(α2,6)Gal binding towards Sia(α2,3)Gal binding which is found when influenza viruses are grown in eggs. Furthermore, it allows for the use of influenza viruses which have not been adapted to high growth in eggs which, again, favors the production of influenza viruses which resemble the circulating strains more closely. Accordingly, these influenza viruses will be a much better match for the circulating human influenza viruses and can thus be expected to provide better protection.

Alternatively, the antigen(s) from the second influenza vaccine may be recombinant protein antigen(s).

Preferably, the antigen(s) in the second influenza vaccine has not been passaged in eggs.

The second influenza vaccine may be a monovalent influenza vaccine. It may also contain more than one influenza antigen, for example two, three, four, five, six or more influenza antigens provided that at least one influenza antigen was prepared from an influenza virus which has been grown in cell culture. As discussed above, it is understood that the at least one influenza antigen which has been grown in cell culture will be of the same subtype as an influenza antigen in the first influenza vaccine which has been passaged in eggs.

Preferably, the antigen in the second influenza vaccine which has been prepared from an influenza virus grown in cell culture has never been passaged in eggs. As discussed above, such antigens can be distinguished from influenza antigens prepared from influenza viruses that have been passaged in eggs by virtue of their preferential binding preference for a Sia(α2,3)Gal terminal disaccharide compared to oligosaccharides with a Sia(α2,6)Gal terminal disaccharide.

When cell culture is used, the viral growth substrate will typically be a cell line of mammalian origin. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC 5; PER.C6; WI-38; etc. Preferred mammalian cell lines for growing influenza viruses include: MDCK cells (refs. 16-19), derived from Madin Darby canine kidney; Vero cells (refs. 20-22), derived from African green monkey (*Cercopithecus aethiops*) kidney; or PER.C6 cells (ref. 23), derived from human embryonic retinoblasts. These cell lines are widely available e.g. from the American Type Cell Culture (ATCC) collection (ref. 24), from the Coriell Cell Repositories (ref. 25), or from the European Collection of Cell Cultures (ECACC). For example, the ATCC supplies various different Vero cells under catalog numbers CCL 81, CCL 81.2, CRL 1586 and CRL-1587, and it supplies MDCK cells under catalog number CCL 34. PER.C6 is available from the ECACC under deposit number 96022940.

Influenza viruses can also be grown on avian cells lines (e.g., refs. 26-28), including avian embryonic stem cells (refs. 26 & 29) and cell lines derived from ducks (e.g., duck retina), or from hens. Suitable avian embryonic stem cells, include the EBx cell line derived from chicken embryonic stem cells, EB45, EB14, and EB14-074 (ref. 30). Chicken embryo fibroblasts (CEF) can also be used. The most preferred avian cell line is the EB66 cell line, which is derived from duck embryonic stem cells. This cell line has been reported to work well for producing influenza antigens (ref. 31).

Preferably, the cell culture of the present invention is mammalian. Use of mammalian cells is particularly preferable where a strain in the vaccine as described herein is a strain that is susceptible to egg adaptation. For example, if antigenic mismatch of a first influenza vaccine is associated with egg-adaptive mutation, a second influenza vaccine (e.g., rescue vaccine) should be manufactured in an egg-free process, such as a mammalian cell-based platform.

When cell culture is used, the cells may avoid the selection pressure on hemagglutinin away from Sia(α2,6)Gal binding. Indeed, certain non-mammalian cells (e.g. avian cells) may be adapted to have receptor oligosaccharides with a Sia(α2,6)Gal terminal disaccharide. For example, non-mammalian cells may be genetically engineered to express a mammalian enzyme or enzymes. Antigen from virus grown in such cells may therefore have a binding preference for oligosaccharides with a Sia(α2,6)Gal terminal disaccharide compared to oligosaccharides with a Sia(α2,3)Gal terminal disaccharide.

The most preferred cell lines for growing influenza viruses are MDCK cells. The original MDCK cell line is available from the ATCC as CCL 34, but derivatives of this cell line may also be used. For instance, reference 16 discloses a MDCK cell line that was adapted for growth in suspension culture ('MDCK 33016', deposited as DSM ACC 2219). Similarly, reference 32 discloses a MDCK-derived cell line that grows in suspension in serum free culture ('B-702', deposited as FERM BP-7449). Reference 33 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 34 discloses MDCK cell lines with high susceptibility to infection, including 'MDCK.5F1' cells (ATCC CRL 12042). Any of these MDCK cell lines can be used.

Where virus has been grown on a cell line then the composition will advantageously be free from egg proteins (e.g., ovalbumin and ovomucoid) and from chicken DNA, thereby reducing allergenicity.

Where virus has been grown on a cell line then the culture for growth, and also the viral inoculum used to start the culture, will preferably be free from (i.e., will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses (in particular porcine circoviruses), and/or parvoviruses (ref. 35). Absence of herpes simplex viruses is particularly preferred.

Where virus has been grown on a cell line then the composition preferably contains less than 10 ng (preferably less than 1 ng, and more preferably less than 100 pg) of residual host cell DNA per dose (typically 0.25 mL for children or 0.5 mL for adults), although trace amounts of host cell DNA may be present. In general, the host cell DNA that it is desirable to exclude from compositions of the invention is DNA that is longer than 100 bp, e.g., DNA fragments longer than 150 bp, longer than 200 bp, etc.

Measurement of residual host cell DNA is now a routine regulatory requirement for biologicals and is within the normal capabilities of the skilled person. The assay used to measure DNA will typically be a validated assay (refs. 36 & 37). The performance characteristics of a validated assay can be described in mathematical and quantifiable terms, and its possible sources of error will have been identified. The assay will generally have been tested for characteristics such as accuracy, precision, specificity. Once an assay has been calibrated (e.g., against known standard quantities of host cell DNA) and tested then quantitative DNA measurements can be routinely performed. Three principle techniques for DNA quantification can be used: hybridization methods, such as Southern blots or slot blots (ref. 38); immunoassay methods, such as the Threshold™ System (ref. 39); and quantitative PCR (ref. 40). These methods are all familiar to the skilled person, although the precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals (ref. 38). A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA, e.g., AppTec™ Laboratory Services, BioReliance™, Althea Technologies, etc. A comparison of a chemiluminescent hybridization assay and the total DNA Threshold™ system for measuring host cell DNA contamination of a human viral vaccine can be found in reference 41.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 42 and 43, involving a two-step treatment, first using a DNase (e.g. Benzonase), which may be used during viral growth, and then a cationic detergent (e.g. CTAB), which may be used during virion disruption. Treatment with an alkylating agent, such as 3-propiolactone, can also be used to remove host cell DNA, and advantageously may also be used to inactivate virions (ref. 44). Methods using two steps of treatment with an alkylating agent or a combination of a DNase and an alkylating agent have also been described (ref. 45).

Vaccines containing <10 ng (e.g., <1 ng, <100 pg) host cell DNA per 15 µg of hemagglutinin are preferred, as are vaccines containing <10 ng (e.g., <1 ng, <100 pg) host cell DNA per 0.25 ml volume. Vaccines containing <10 ng (e.g., <1 ng, <100 pg) host cell DNA per 50 µg of hemagglutinin are more preferred, as are vaccines containing <10 ng (e.g., <1 ng, <100 pg) host cell DNA per 0.5 ml volume.

It is preferred that the average length of any residual host cell DNA is less than 500 bp, e.g., less than 400 bp, less than 300 bp, less than 200 bp, less than 100 bp, etc.

For growth on a cell line, such as on MDCK cells, virus may be grown on cells in suspension (refs. 16, 46 & 47) or in adherent culture. One suitable MDCK cell line for suspension culture is MDCK 33016 (deposited as DSM ACC 2219). As an alternative, microcarrier culture can be used.

According to the present disclosure, cell culture may be used to isolate and grow virus, from a wild-type sample (e.g. a clinical sample), which virus may be used to produce a vaccine or a composition for use according to the invention. The isolate is preferably an isolate of a circulating strain (obtained from the sample). The isolate may be an isolate of a clade or strain that is susceptible to egg adaptation and/or to clade mismatch. Isolation and growth in cell culture may provide further advantages to the composition and the production process when compared to virus isolated and grown in eggs. Isolation in cell culture may significantly improve isolation rates from clinical samples compared to virus isolated using eggs. Isolation and growth in cell culture may elicit higher growth rates and/or increased virus yield compared to virus isolated and grown in an egg-based process. Furthermore, isolation and growth in cell culture may provide improved genetic stability (as described above), i.e., the ability to retain the genetic sequence of the original clinical samples, without introducing host adaptive mutations that cause antigenic mismatch. These effects may be particularly advantageous where the clade or strain is susceptible to egg adaptation and/or to clade mismatch (e.g. a strain from the B/Victoria lineage), and/or where a rescue vaccine (e.g. a second influenza vaccine) having a closer antigenic match to a particular circulating strain than a first influenza vaccine is to be provided (particularly when it is to be provided for administration within the same season as the first influenza vaccine). These effects may also be particularly advantageous in embodiments where the vaccine contains one or two B strains. The B strain(s) may be from the B/Victoria lineage and/or the B/Yamagata lineage. In some preferred embodiments, the B/Victoria strain is present and is a strain or clade that is susceptible to egg adaptation and/or to clade mismatch. The vaccine may, for example, be a tetravalent vaccine comprising two A strains and two B strains (AABB) or a trivalent vaccine comprising two A strains and one B strain (AAB). Preferably, the vaccine comprises at least two B strains, e.g. a tetravalent AABB vaccine. Cell culture-based isolation and growth may be particularly advantageous for producing, from clinical samples, multiple B strains for use in producing rescue vaccines and compositions described herein. The B strains produced in cell culture may exhibit isolation rates, growth rates, yield and/or genetic stability that is superior to B strains produced in eggs. The cell culture is preferably MDCK cell culture as described herein (which may be MDCK 33016PF cell culture).

Cell lines supporting influenza virus replication are preferably grown in serum free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. (ref. 48) (e.g., 30-36° C., or at about 30° C., 31° C., 32° C., 33° C., 34° C., 35° C., 36° C.), for example during viral replication.

The method for propagating virus in cultured cells generally includes the steps of inoculating the cultured cells with the strain to be cultured, cultivating the infected cells for a desired time period for virus propagation, such as for example as determined by virus titer or antigen expression (e.g., between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g., monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at an m.o.i of about 0.01. Infected cells may be harvested 30 to 60 hours post infection. Preferably, the cells are harvested 34 to 48 hours post infection. Still more preferably, the cells are harvested 38 to 40 hours post infection. Nevertheless, determining the optimal harvest time is within the normal capabilities of a person skilled in the art. Proteases (typically trypsin) are generally added during cell culture to allow viral release, and the proteases can be added at any suitable stage during the culture.

The influenza virus may be a reassortant strain, and may have been obtained by reverse genetics techniques. Reverse genetics techniques (e.g., refs. 49-53) allow influenza viruses with desired genome segments to be prepared in vitro using plasmids. Typically, it involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred (refs. 54-56), and these methods will also involve the use of plasmids to express all or some (e.g., just the PB1, PB2, PA and NP proteins) of the viral proteins, with 12 plasmids being used in some methods. The use of linear expression constructs is also possible (ref. 57).

To reduce the number of plasmids needed, a recent approach (ref. 58) combines a plurality of RNA polymerase I transcription cassettes (for viral RNA synthesis) on the same plasmid (e.g., sequences encoding 1, 2, 3, 4, 5, 6, 7 or all 8 influenza A vRNA segments), and a plurality of protein coding regions with RNA polymerase II promoters on another plasmid (e.g., sequences encoding 1, 2, 3, 4, 5, 6, 7 or all 8 influenza A mRNA transcripts). Preferred aspects of the reference 55 method involve: (a) PB1, PB2 and PA mRNA encoding regions on a single plasmid; and (b) all 8 vRNA encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters (ref. 59). For instance, promoters for the SP6, T3 or T7 polymerases can conveniently be used. Because of the species specificity of polI promoters, bacteriophage polymerase promoters can be more convenient for many cell types (e.g., MDCK), although a cell must also be transfected with a plasmid encoding the exogenous polymerase enzyme.

In other techniques it is possible to use dual polI and polII promoters to simultaneously code for the viral RNAs and for expressible mRNAs from a single template (refs. 60 & 61).

Thus an influenza A virus may include one or more RNA segments from a A/PR/8/34 virus (typically 6 segments from A/PR/8/34, with the HA and NA segments being from a vaccine strain, i.e., a 6:2 reassortant), particularly when viruses are grown in eggs. It may also include one or more RNA segments from a A/WSN/33 virus, or from any other virus strain useful for generating reassortant viruses for vaccine preparation. References 62 and 63 also discuss suitable backbones for reassorting influenza A and B strains.

Typically, the invention protects against a strain that is capable of human-to-human transmission, and so the strain's genome will usually include at least one RNA segment that originated in a mammalian (e.g., in a human) influenza virus. It may include an NS segment that originated in an avian influenza virus.

Hemagglutinin (HA) is the main immunogen in inactivated influenza vaccines, and vaccine doses are standardised by reference to HA levels, typically as measured by a single radial immunodiffusion (SRID) assay. Vaccines typically contain about 15 µg of HA per strain, although lower doses are also used, e.g., for children, or in pandemic situations. Fractional doses such as ½ (i.e., 7.5 µg HA per strain), ¼ and ⅛ have been used (refs. 64 & 65), as have higher doses (e.g., 3× or 9× doses (refs. 66 & 67)). Thus vaccines may include between 0.1 and 150 µg of HA per influenza strain, preferably between 0.1 and 50 µg, e.g., 0.1-20 µg, 0.1-15 µg, 0.1-10 µg, 0.1-7.5 µg, 0.5-5 µg, etc. Particular doses include, e.g., about 45, about 30, about 15, about 10, about 7.5, about 5, about 3.8, about 1.9, about 1.5 µg, etc. per strain. These lower doses are most useful when an adjuvant is present in the vaccine. The components of the vaccines, kits and processes of the invention (e.g., their volumes and concentrations) may be selected to provide these antigen doses in final products.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

HA used with the invention may be a natural HA as found in a virus, or may have been modified. For instance, it is known to modify HA to remove determinants (e.g., hyperbasic regions around the cleavage site between HA1 and HA2) that cause a virus to be highly pathogenic in avian species, as these determinants can otherwise prevent a virus from being grown in eggs.

Compositions may include detergent, e.g., a polyoxyethylene sorbitan ester surfactant (known as 'Tweens'), an octoxynol (such as octoxynol-9 (Triton X-100) or t octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol 10, α-tocopheryl hydrogen succinate and polysorbate 80. Other residual components in trace amounts could be antibiotics (e.g., neomycin, kanamycin, polymyxin B).

An inactivated but non whole cell vaccine (e.g., a split virus vaccine or a purified surface antigen vaccine) may include matrix protein, in order to benefit from the additional T cell epitopes that are located within this antigen. Thus a non-whole cell vaccine (particularly a split vaccine) that includes hemagglutinin and neuraminidase may additionally include M1 and/or M2 matrix protein. Where a matrix protein is present, inclusion of detectable levels of M1 matrix protein is preferred. Nucleoprotein may also be present.

The antigen in the first influenza vaccine will typically be prepared from influenza virions but, as an alternative, antigens such as hemagglutinin can be expressed in a recombinant host (e.g., in yeast using a plasmid expression system, or in an insect cell line using a baculovirus vector) and used in purified form (refs. 68 & 69). In general, however, antigens will be from virions.

Pharmaceutical Compositions

Vaccines used with the invention are pharmaceutically acceptable. They may include components in addition to the antigen and adjuvant, e.g., they will typically include one or more pharmaceutical carrier(s) and/or excipient(s). A thorough discussion of such components is available in reference 70. The carrier(s)/excipient(s) used in mucosal vaccines may be the same as or different from those used in parenteral vaccines.

Compositions may include preservatives such as thiomersal or 2-phenoxyethanol. It is preferred, however, that the vaccines should be substantially free from (i.e., less than 5 µg/ml) mercurial material, e.g., thiomersal-free (refs. 8 & 71). Vaccines containing no mercury are more preferred.

To control tonicity, particularly in injectable vaccines, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions for injection will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination (ref. 72), but keeping osmolality in this range is nevertheless preferred.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition will generally be between 5.0 and 8.1, and more typically between 6.0 and 8.0, e.g., between 6.5 and 7.5, or between 7.0 and 7.8. A process of the invention may therefore include a step of adjusting the pH of the bulk vaccine prior to packaging.

The composition is preferably sterile. The composition is preferably non pyrogenic e.g. containing <1 EU (endotoxin unit, a standard measure) per dose, and preferably <0.1 EU per dose. The composition is preferably gluten free.

The composition may include material for a single immunization, or may include material for multiple immunizations (i.e., a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half volume (i.e., about 0.25 ml) may be administered to children. For intranasal administration, this total dosage volume can be split between nostrils e.g. ½ in each nostril.

Compositions and kits are preferably stored at between 2° C. and 8° C. Typically, they should not be frozen. They should ideally be kept out of direct light.

Packaging of Compositions or Kit Components

Suitable containers for compositions of the invention (or kit components) include vials, syringes (e.g., disposable syringes), nasal sprays, etc. These containers should be sterile.

Where a composition/component is located in a vial, the vial is preferably made of a glass or plastic material. The vial is preferably sterilized before the composition is added to it. To avoid problems with latex sensitive patients, vials are preferably sealed with a latex-free stopper, and the absence of latex in all packaging material is preferred. The vial may include a single dose of vaccine, or it may include more than one dose (a 'multidose' vial), e.g., 10 doses. Preferred vials are made of colorless glass.

A vial can have a cap (e.g., a Luer lock) adapted such that a pre filled syringe can be inserted into the cap, the contents of the syringe can be expelled into the vial (e.g., to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a composition/component is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half dose volume, e.g., to facilitate delivery to children. For instance, a syringe containing a 0.5 ml dose may have a mark showing a 0.25 ml volume.

Where a glass container (e.g., a syringe or a vial) is used, then it is preferred to use a container made from a borosilicate glass rather than from a soda lime glass.

A kit or composition may be packaged (e.g., in the same box) with a leaflet including details of the vaccine e.g. instructions for administration, details of the antigens within the vaccine, etc. The instructions may also contain warnings, e.g., to keep a solution of adrenaline readily available in case of anaphylactic reaction following vaccination, etc.

Methods of Treatment, and Administration of the Vaccine

The immune response raised by the methods and uses of the invention will generally include an antibody response, preferably a protective antibody response. Methods for assessing antibody responses, neutralizing capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) (ref. 73). Antibody responses are typically measured by hemagglutination inhibition, by microneutralization, by single radial immunodiffusion (SRID), and/or by single radial hemolysis (SRH). These assay techniques are well known in the art.

For mucosal administration of vaccines, routes that may be used include, but are not limited to, rectal, oral (e.g., tablet, spray), pharyngeal, buccal, vaginal, topical, transdermal or transcutaneous, intranasal, ocular, pulmonary, etc. As mentioned above, the preferred mucosal administration route is by intranasal injection. Nasal administration can be, e.g., by spray, drops, aerosol, etc.

For parenteral administration of vaccines, routes that may be used include, but are not limited to, intramuscular injection, subcutaneous injection, intravenous injection, intraperitoneal injection (where available), intradermal injection, etc., and other systemic routes. As mentioned above, the preferred parenteral administration route is by intramuscular injection (e.g., into the arm or leg).

The administration regimes according to the invention may be used to treat both children and adults. Influenza vaccines are currently recommended for use in pediatric and adult immunization, from the age of 6 months. Thus the patient may be less than 1 year old, 1-5 years old, 5-15 years old, 15-55 years old, or at least 55 years old. Preferred patients for receiving the vaccines are the elderly (e.g., ≥50 years old, ≥60 years old, preferably ≥65 years), the young (e.g., ≤5 years old), hospitalized patients, healthcare workers, armed service and military personnel, pregnant women, the chronically ill, immunodeficient patients, patients who have taken an antiviral compound (e.g., an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Conventional vaccines containing mismatched antigen may provide only limited protection particularly for individuals considered to be "at high-risk" (see, for example, http://www.cdc.gov/flu/about/disease/high_risk.htm). High-risk individuals are typically more susceptible to greater severity of an infection, secondary infections, both greater occurrences and longer durations of hospitalization, and/or death. High-risk individuals also include those who are more readily exposed to viruses. For example, high-risk patients may be selected from patients≥65 years of age, ≤5 years old (more preferably ≤2 years old), hospitalized patients, healthcare workers, armed service and military personnel, pregnant women, the chronically ill, immunodeficient patients, and patients who have taken an antiviral compound in the 7 days prior to receiving the vaccine. Vaccines and methods provided herein are useful for providing immune-protection in such high-risk patients. Accordingly, the invention includes methods for immunizing a patient, comprising a step of administering to the patient the composition of any one of the embodiments described herein, wherein the patient is a high-risk patient.

Preferred compositions of the invention satisfy 1, 2 or 3 of the European Committee for Medicinal Products for Human Use (CHMP, formerly known as CPMP) criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients. According to CHMP criteria, seroconversion rate for anti-HA antibody response is defined as the proportion of subjects in each group having a protective post-vaccination titre≥40. The seroconversion rate is the % of subjects who have an HI titre before vaccination of <1:10 and ≥1:40 after vaccination. However, if the initial titre is ≥1:10 then there needs to be at least a fourfold increase in the amount of antibody after vaccination.

Alternatively, or in addition, preferred compositions of the invention satisfy 1 or 2 of the immunological criteria established for influenza vaccines by the Center for Biologics Evaluation and Research (CBER). In adults (18-64 years), these criteria are: (1) the % of subjects achieving an HI antibody titer≥40 should be ≥70%; (2) ≥40% seroconversion. In elderly (>64 years), these criteria are: (1) the % of subjects achieving an HI antibody titer≥1:40 should be ≥60%; (2) ≥30% seroconversion. According to CBER criteria, the seroconversion rate is defined as: a) for subjects with a baseline titer≥40% seroconversion 1:10, a 4-fold or greater rise; or b) for subjects with a baseline titer<1:10, a rise to ≥40. These criteria must be met at the lower bound of the 95% CI for the true value.

Endpoints may be measured at three weeks (e.g. at day 22) after vaccination (in a two-dose administration schedule, this is typically calculated from after the second dose).

The same (e.g. adult) criteria may be relied on for pediatric patient groups (e.g. <18 years of age).

It is within the normal capabilities of the skilled person to assess whether a "statistically acceptable" immune response, as referred to above, is provided by a given composition. A statistically acceptable response may be demonstrated immunogenicity according to CHMP or CBER criteria, for example, such that at least one of the above criteria is met at the lower bound of the 95% CI for the true value.

The vaccines administered according to the invention are administered during the same influenza season. In the northern hemisphere the influenza season typically lasts from October to May with influenza activity peaks being between December and February. In the southern hemisphere, the influenza seasons starts in May, peaks in July and ends in October. The second influenza vaccine may be administered within 1 month, 2 months, 3 months, 4 months or 5 months after the first influenza vaccine. Preferably, the second influenza vaccine is administered within 3 months after the first influenza vaccine.

The vaccines may be administered to patients at substantially the same time as (e.g., during the same medical consultation or visit to a healthcare professional or vaccination center) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated H. influenzae type b vaccine, an inactivated poliovirus vaccine, a hepatitis B virus vaccine, a meningococcal conjugate vaccine (such as a tetravalent A C W135 Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines may be administered to patients at substantially the same time as (e.g., during the same medical consultation or visit to a healthcare professional) an antiviral compound, and in particular an antiviral compound active against influenza virus (e.g., oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

The term "vaccine effectiveness" (or "VE") represents the reduction in risk provided by the flu vaccine. For example, in the United States, Centers for Disease Control and Prevention (CDC) vaccine effectiveness studies commonly measure laboratory confirmed flu illness that results in a doctor's visit or urgent care visit as an outcome. For this outcome, a VE point estimate of 50% means that the flu vaccine reduces a person's risk of developing flu illness that results in a visit to the doctor's office or urgent care provider by 50%. Determining VE is within the normal capabilities of the skilled person. VE may be as determined by a regulatory body such as the US CDC. For example, VE may be determined using the methods described in the prior art (ref. 111) wherein VE (%) is calculated as $[1-_{adjusted}OR]\times100$, wherein OR is the estimated odds ratio for medically-attended, laboratory confirmed influenza in vaccinated versus non-vaccinated subjects (ref. 111). The estimated $_{adjusted}OR$ may be determined by logistic regression with adjustment for clinically-relevant confounders. Per previous VE analyses, covariates include age, comorbidity, province, week of specimen collection and the interval between influenza-like illness (ILI) onset and specimen collection.

Adjuvant(s)

The first and/or second influenza vaccine(s) may be un-adjuvanted, or they may be administered with an adjuvant. The adjuvant(s) can function to enhance the immune responses (humoral and/or cellular) elicited in a patient who receives the composition. Some adjuvants are effective for parenteral administration but not for mucosal administration (e.g. aluminum salts), and vice versa, although some adjuvants are effective for both routes. Where adjuvants are used, they will be chosen accordingly.

Oil-in-Water Emulsion Adjuvants

Oil-in-water emulsions have been found to be particularly suitable for use in adjuvanting influenza virus vaccines. Various such emulsions are known, and they typically include at least one oil and at least one surfactant, with the oil(s) and surfactant(s) being biodegradable (metabolizable) and biocompatible. The oil droplets in the emulsion are generally less than 5 μm in diameter, and may even have a submicron diameter, with these small sizes being achieved with a microfluidiser to provide stable emulsions. Droplets with a size less than 220 nm are preferred as they can be subjected to filter sterilization.

In preferred embodiments, the emulsion is uniform. A uniform emulsion is characterized in that a majority of droplets (particles) dispersed therein is within a specified size range (e.g., in diameter). Suitable ranges of specified particle size can be, for example, between 50-220 nm, between 50-180 nm, between 80-180 nm, between 100-175 nm, between 120-185 nm, between 130-190 nm, between 135-175 nm, between 150-175 nm. In some embodiments, the uniform emulsion contains ≤10% of the number of droplets (particles) that are outside of the specified range of diameters. In some embodiments, mean particle size of oil droplets in the oil-in-water emulsion preparation is between 135-175 nm, e.g., 155 nm±20 nm, as measured by dynamic light scattering, and such a preparation contains not more than $1\times10^7$ large particles per mL of the preparation, as measured by optical particle sensing. "Large particles" as used herein mean those having diameters>1.2 μm, typically between 1.2-400 μm. In preferred embodiments, the uniform emulsion contains less than 10%, less than 5%, or less than 3% of the droplets that fall outside of the preferred size range. In some embodiments, the mean droplet size of particles in an oil-in-water emulsion preparation is between 125-185 nm, e.g., about 130 nm, about 140 nm, about 150 nm, about 155 nm, about 160 nm, about 170 nm, or about 180 nm, and the oil-in-water emulsion is uniform in that less than 5% of the number of droplets in the preparation fall outside the 125-185 nm range.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used, e.g., obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their "HLB" (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Nonionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used, e.g., Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

The most preferred oil-in-water emulsions are squalene-in-water emulsions, preferably submicron squalene-in-water emulsions.

Specific oil-in-water emulsion adjuvants useful with the invention include, but are not limited to the following:

A Submicron Emulsion of Squalene, Polysorbate 80, and Sorbitan Trioleate:

The composition of the emulsion by volume can be about 5% squalene, about 0.5% polysorbate 80 and about 0.5% sorbitan trioleate. In weight terms, these ratios become 4.3% squalene, 0.5% polysorbate 80 and 0.48% sorbitan trioleate. The emulsion may include citrate ions, e.g., 10 mM sodium citrate buffer. The citrate ions may be in the aqueous phase. More particularly, the composition of the emulsion by volume can be about 4.6% squalene, about 0.45% polysorbate 80 and about 0.5% sorbitan trioleate. The adjuvant known as "MF59" (refs. 74-76 and 133) is described in more detail in Chapter 10 of reference 133 and chapter 12 of reference 77. Squalene, polysorbate 80 and sorbitan trioleate may be present at a weight ratio of 9750:1175:1175. In some embodiments, the emulsion may contain 36-42 mg/ml squalene as measured by RP-HPLC; 4.1-5.3 mg/ml polysorbate 80 as measured by RP-LC; and 4.1-5.3 mg/ml sorbitan trioleate as measured by RP-LC. Concentrations of about 39 mg/mL squalene, about 4.7 mg/mL polysorbate 80, and about 4.7 mg/mL sorbitan trioleate are typical. In some embodiments, mean particle size, as measured by dynamic light scattering, of 155±20 nm is preferred. A Z-average droplet size of between 155-185 nm is preferred, with a polydispersity of <0.2. Preferably, the submicron emulsion comprising squalene, polysorbate 80 and sorbitan trioleate is uniform (see above).

An emulsion of squalene, a tocopherol, and Tween 80: The emulsion may include phosphate buffered saline. It may also include Span 85 (e.g., at 1%) and/or lecithin. These emulsions may have from 2 to 10% squalene, from 2 to 10% tocopherol and from 0.3 to 3% Tween 80, and the weight ratio of squalene:tocopherol is preferably <1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidizing the mixture. The resulting emulsion may have submicron oil droplets, e.g., with an average diameter of between 100 and 250 nm, preferably about 150-180 nm, e.g., about 150 nm, about 160 nm, about 170 nm or about 180 nm.

An Emulsion of Squalene, a Tocopherol, and a Triton Detergent:

The emulsion may also include a 3d MPL (see below). The Triton detergent of the emulsion can be Triton X-100. The tocopherol can be α-tocopherol. The emulsion may contain a phosphate buffer.

An Emulsion Comprising a Polysorbate (e.g. Polysorbate 80), a Triton Detergent (e.g. Triton X-100) and a Tocopherol (e.g. an α-Tocopherol Succinate):

The emulsion may include these three components at a mass ratio of about 75:11:10 (e.g., 750 μg/ml polysorbate 80, 110 μg/ml Triton X-100 and 100 μg/ml α-tocopherol succinate), and these concentrations should include any contribution of these components from antigens. The emulsion can comprise polysorbate 80, Triton X-100, and an α-tocopherol succinate. The emulsion may also include squalene. The emulsion may also include a 3d MPL (see below). The aqueous phase may contain a phosphate buffer.

An Emulsion of Squalane, Polysorbate 80 and Poloxamer 401 ("Pluronic™ L121"):

The emulsion can be formulated in phosphate buffered saline, pH 7.4. This emulsion is a useful delivery vehicle for muramyl dipeptides, and has been used with threonyl MDP in the "SAF-1" adjuvant (ref. 78) (0.05-1% Thr MDP, 5% squalane, 2.5% Pluronic L121 and 0.2% polysorbate 80). It can also be used without the Thr MDP, as in the "AF" adjuvant (ref. 79) (5% squalane, 1.25% Pluronic L121 and 0.2% polysorbate 80). Microfluidization is preferred.

An Emulsion Having from 0.5-50% of an Oil, 0.1-10% of a Phospholipid, and 0.05-5% of a Non-Ionic Surfactant:

As described in reference 80, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A Submicron Oil-in-Water Emulsion of a Non-Metabolizable Oil (Such as Light Mineral Oil) and at Least One Surfactant (Such as Lecithin, Tween 80 or Span 80):

Additives may be included, such as QuilA saponin, cholesterol, a saponin-lipophile conjugate (such as GPI-0100, described in reference 81, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An Emulsion in which a Saponin (e.g. QuilA or QS21) and a Sterol (e.g. Cholesterol) are Associated as Helical Micelles:

The saponin can be QuilA and/or QS21, and the sterol can be a cholesterol (ref. 82).

An Emulsion Comprising a Mineral Oil, a Non-Ionic Lipophilic Ethoxylated Fatty Alcohol, and a Non-Ionic Hydrophilic Surfactant:

The emulsion may comprise an ethoxylated fatty alcohol and/or polyoxyethylene-polyoxypropylene block copolymer) (ref. 83).

An Emulsion Comprising a Mineral Oil, a Non-Ionic Hydrophilic Ethoxylated Fatty Alcohol, and a Non-Ionic Lipophilic Surfactant:

The emulsion may comprise an ethoxylated fatty alcohol and/or polyoxyethylene-polyoxypropylene block copolymer (ref. 83).

According to the invention, the emulsions may be mixed with antigen extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g., between 5:1 and 1:5) but is generally about 1:1.

After the antigen and adjuvant have been mixed, hemagglutinin antigen will generally remain in aqueous solution but may distribute itself around the oil/water interface. In general, little if any hemagglutinin will enter the oil phase of the emulsion.

Where a composition includes a tocopherol, any of the α, β, γ, δ, ε or ξ tocopherols can be used, but α-tocopherols are preferred. The tocopherol can take several forms, e.g., different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g., aged 60 years or older, 61 years or older, 65 years or older, etc.) because vitamin E has been reported to have a positive effect on the immune response in this patient group (ref. 84). They also have antioxidant properties that may help to stabilize the emulsions (ref. 85). A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds (ref. 8). Preservative-free vaccines are particularly preferred.

Immunostimulatory Oligonucleotides

Immunostimulatory oligonucleotides can include nucleotide modifications/analogs such as phosphorothioate modifications and can be double-stranded or (except for RNA) single-stranded. References 86, 87 and 88 disclose possible analog substitutions, e.g., replacement of guanosine with 2'-deoxy-7-deazaguanosine. The adjuvant effect of CpG oligonucleotides is further discussed in references 89-94. A CpG sequence may be directed to TLR9, such as the motif GTCGTT or TTCGTT (ref. 95). The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in references 96-98.

Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 95 & 99-101. A useful CpG adjuvant is CpG7909, also known as ProMune™ (Coley Pharmaceutical Group, Inc.).

As an alternative, or in addition, to using CpG sequences, TpG sequences can be used (ref. 102). These oligonucleotides may be free from unmethylated CpG motifs.

The immunostimulatory oligonucleotide may be pyrimidine rich. For example, it may comprise more than one consecutive thymidine nucleotide (e.g., TTTT, as disclosed in ref. 102), and/or it may have a nucleotide composition with >25% thymidine (e.g., >35%, >40%, >50%, >60%, >80%, etc.). For example, it may comprise more than one consecutive cytosine nucleotide (e.g., CCCC, as disclosed in ref. 102), and/or it may have a nucleotide composition with >25% cytosine (e.g., >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

3 De-O-Acylated Monophosphoryl Lipid A

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-α and GM-CSF (see also ref. 103). Preparation of 3dMPL was originally described in reference 104.

3dMPL can take the form of a mixture of related molecules, varying by their acylation (e.g., having 3, 4, 5 or 6 acyl chains, which may be of different lengths). The two glucosamine (also known as 2-deoxy-2-amino-glucose) monosaccharides are N-acylated at their 2-position carbons (i.e., at positions 2 and 2'), and there is also O-acylation at the 3' position. The group attached to carbon 2 has formula —NH—CO—CH$_2$—CR$^1$R$^{1'}$. The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is:

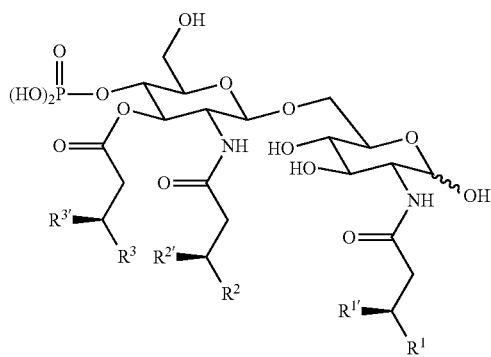

Groups R$^1$, R$^2$ and R$^3$ are each independently —(CH$_2$)$_n$—CH$_3$. The value of n is preferably between 8 and 16, more preferably between 9 and 12, and is most preferably 10.

Groups R$^{1'}$, R$^{2'}$ and R$^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, m is preferably 10. At the 3' position, m is preferably 12. Groups R$^{1'}$, R$^{2'}$ and R$^{3'}$ are thus preferably —O-acyl groups from dodecanoic acid, tetradecanoic acid or hexadecanoic acid.

When all of R$^{1'}$, R$^{2'}$ and R$^{3'}$ are —H then the 3dMPL has only 3 acyl chains (one on each of positions 2, 2' and 3'). When only two of R$^{1'}$, R$^{2'}$ and R$^{3'}$ are —H then the 3dMPL can have 4 acyl chains. When only one of R$^{1'}$, R$^{2'}$ and R$^{3'}$ is —H then the 3dMPL can have 5 acyl chains. When none of R$^{1'}$, R$^{2'}$ and R$^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL, e.g., ≥20%, ≥0%, ≥40%, ≥50% or more. 3dMPL with 6 acyl chains has been found to be the most adjuvant active form.

Thus the most preferred form of 3dMPL for inclusion in compositions of the invention is:

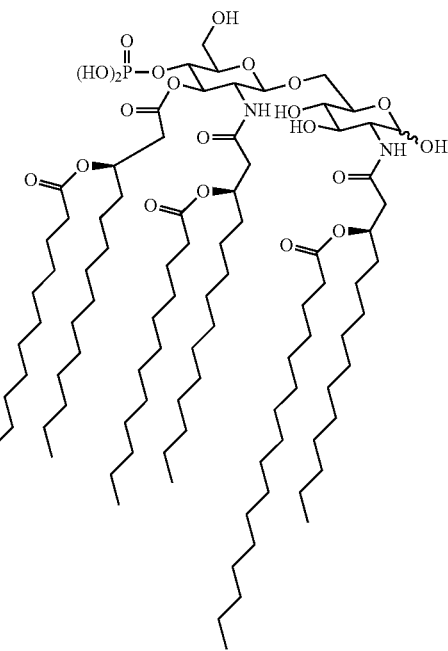

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes, e.g., with a diameter<150 nm or >500 nm. Either or both of these can be used with the invention, and the better particles can be selected by routine assay. Smaller particles (e.g., small enough to give a clear aqueous suspension of 3dMPL) are preferred for use according to the invention because of their superior activity (ref. 105). Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g., ≥60%, ≥70%, ≥80%, ≥90%, or more) of the particles will have a diameter within the range x±25%.

3dMPL can advantageously be used in combination with an oil-in-water emulsion. Substantially all of the 3dMPL may be located in the aqueous phase of the emulsion.

A typical amount of 3dMPL in a vaccine is 10-100 µg/dose, e.g., about 25 µg or about 50 µg.

The 3dMPL can be used on its own, or in combination with one or more further compounds. For example, it is known to use 3dMPL in combination with the QS21 saponin (ref. 106) (including in an oil-in-water emulsion (ref. 107)), with an immunostimulatory oligonucleotide, with both QS21 and an immunostimulatory oligonucleotide, with aluminum phosphate (ref. 108), with aluminum hydroxide (ref. 109), or with both aluminum phosphate and aluminum hydroxide.

General

The term "comprising" encompasses "including" as well as "consisting," e.g., "a composition comprising X" may consist exclusively of X or may include something additional, e.g., X+Y.

The word "substantially" does not exclude "completely," e.g., "a composition that is substantially free from Y" may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encapalopathies (TSEs), and in particular free from bovine spongiform encephalopathy (BSE). Overall, it is preferred to culture cells in the total absence of animal derived materials.

Where a cell substrate is used for reassortment or reverse genetics procedures, it is preferably one that has been approved for use in human vaccine production, e.g., as in Ph Eur general chapter 5.2.3.

This invention is further illustrated by the following examples, which should not be construed as limiting.

EXAMPLES

It will be understood that the invention has been described by way of example only and modifications may be made whilst remaining within the scope and spirit of the invention.

Example 1: Antigenic Mismatch in H3N2

Pathogens and Man have coevolved. There has been an interplay in how the immune system develops to neutralize pathogens and how pathogens develop to evade the immune system.

Influenza viruses include a diverse range of subtypes, classified by surface antigen characteristics. Further variation exists; thus, specific influenza strain isolates are identified by a standard nomenclature specifying virus type, geographical location where first isolated, sequential number of isolation, year of isolation, and HA and NA subtype. Due to a high degree of antigenic variations of surface antigens, it is important that influenza vaccines are prepared to match the dominant circulating (e.g., disease-causing) strains so as to provide sufficient protection.

In recent years, there has been alarmingly low vaccine effectiveness in the U.S., Europe and elsewhere. For example, in the United States, Centers for Disease Control and Prevention (CDC) has reported that 23% vaccine effectiveness (VE) against lab-confirmed H3N2 influenza associated with medically attended acute respiratory illness (ARI). It was observed that 68% of circulating H3N2 viruses showed significant antigenic mismatch from vaccine strain. In the same season, A/Texas/50/2012-like viruses (Clade 3C.1) were recommended, which is a mismatched clade.

Moreover, egg-adapted A/Texas/50/2012-like viruses are a weak match for related circulating viruses. It has been recognized that egg-adaptive mutations affect antigenicity. The 2013-14 season recommendation highlighted the importance of ensuring antigenic match and suggested that new systems are needed to enable better match by non-egg-based processes.

Similarly, in Canada, -8% VE against lab-confirmed influenza associated with medically attended ARI (Eurosurveillance 1/2015) has been reported, in which 99% was identified to be H3N2, of which 91% of the sequenced strains were identified to be the 3C.2A Clade. In the U.K., corresponding numbers are 3.4% VE against primary care consultation with lab-confirmed influenza; -2.3% VE for A(H3N2) (Eurosurveillance 2/2015).

There are at least two key factors in determining the likelihood that flu vaccine will protect a person from flu illness: 1) characteristics of the person being vaccinated (such as their age and health), and 2) the similarity or "match" between the flu viruses the flu vaccine is designed to protect against and the flu viruses spreading in the community. In this regard, CDC has commented that during years when the flu vaccine is not well matched to circulating viruses, it's possible that no benefit from flu vaccination may be observed (See: www.cdc.gov/flu/about/qa/vaccineeffect.htm).

FIG. 1 depicts the relationship between flu-associated illness (as measured by fraction of hospital visits) over the course of a season for each of six influenza seasons. What it indicates is that it is extremely challenging for the system to address antigenic changes. Moreover, egg adaptation may be a driver for unrecognized vaccine antigenic change. It also highlights that by the current system we have in place, effective vaccination against H3N2 has been less than successful. This recognition raises the possibility that in future flu seasons, where H3N2 is predominant, similar antigenic mismatch of available seasonal vaccines may occur. That is, recommendation may be mismatched due to egg adaptation and/or incorrect clade.

As exemplified herein, low vaccine effectiveness correlates with influenza seasons dominated by clade mismatch and egg/cell adaptation mismatch.

For example, certain clades are particularly susceptible to causing antigenic mismatch.

Clade 3C.3A strain has been chosen for upcoming Northern Hemisphere season. It is noteworthy that egg-adapted version (A/Switzerland/9715293/2013) is mismatched to the cell version—matched 13% of tested viruses as reported by UK WHO Collaboration Center. By comparison, the cell version matched closer to 88% of tested circulating viruses.

At the time of drafting of this application, Clade 3C.2A is actually on the rise and predominant. According to Flannery et al. (CDC Report; Jun. 24, 2015), 3C.2A represented over 81% of circulating H3N2 strains based on surveillance from U.S. laboratories. 3C.2A cell version matches circulating viruses, while egg-adaptation results in antigenic mismatch and a concurrent glycosylation loss on the head region of the HA antigen.

Figure 2:
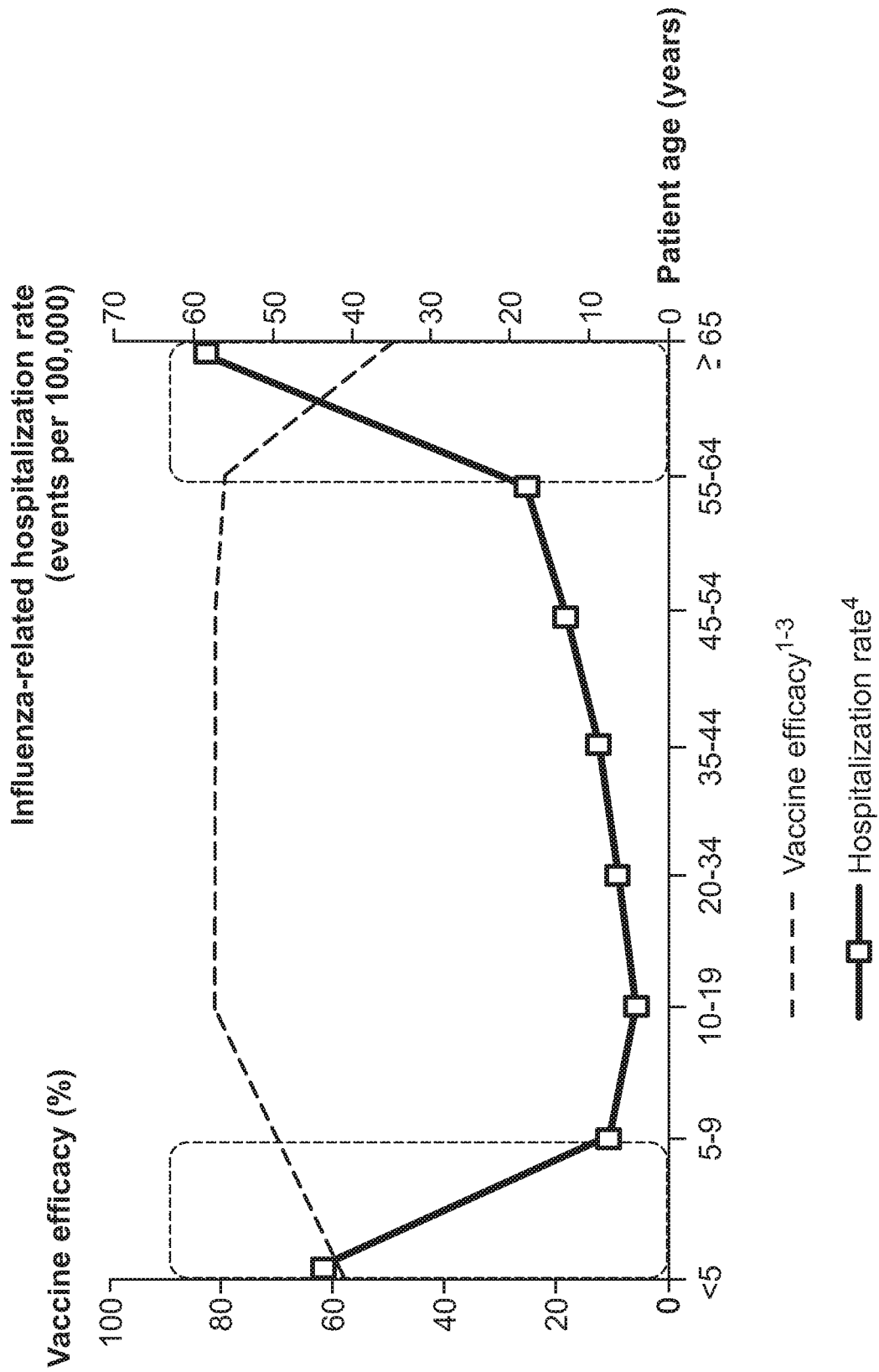
FIG. 2 provides a graph showing the relationship between vaccine efficacy and influenza-related hospitalization rate for different age groups. (Adapted from: Nichol K, et al. Vaccine 2003; 21:1769-1775; Goodwin K, et al. Vaccine 2006; 24:1159-1169; Grubeck-Loebenstein B, et al. Nat Med 1998; 4:870; and, Glezen W P, et al. Am Rev Respir Dis 1987; 136:550-555.)

As is clear from FIG. 2, vaccine efficacy is inversely related to influenza-associated medical needs. This relationship is particularly strong for certain subpopulations of patients, e.g., very young children and the elderly, whose immune system may be premature or suppressed. The same is likely to be said for immunocompromised individuals due to illness or medication.

Figure 4:
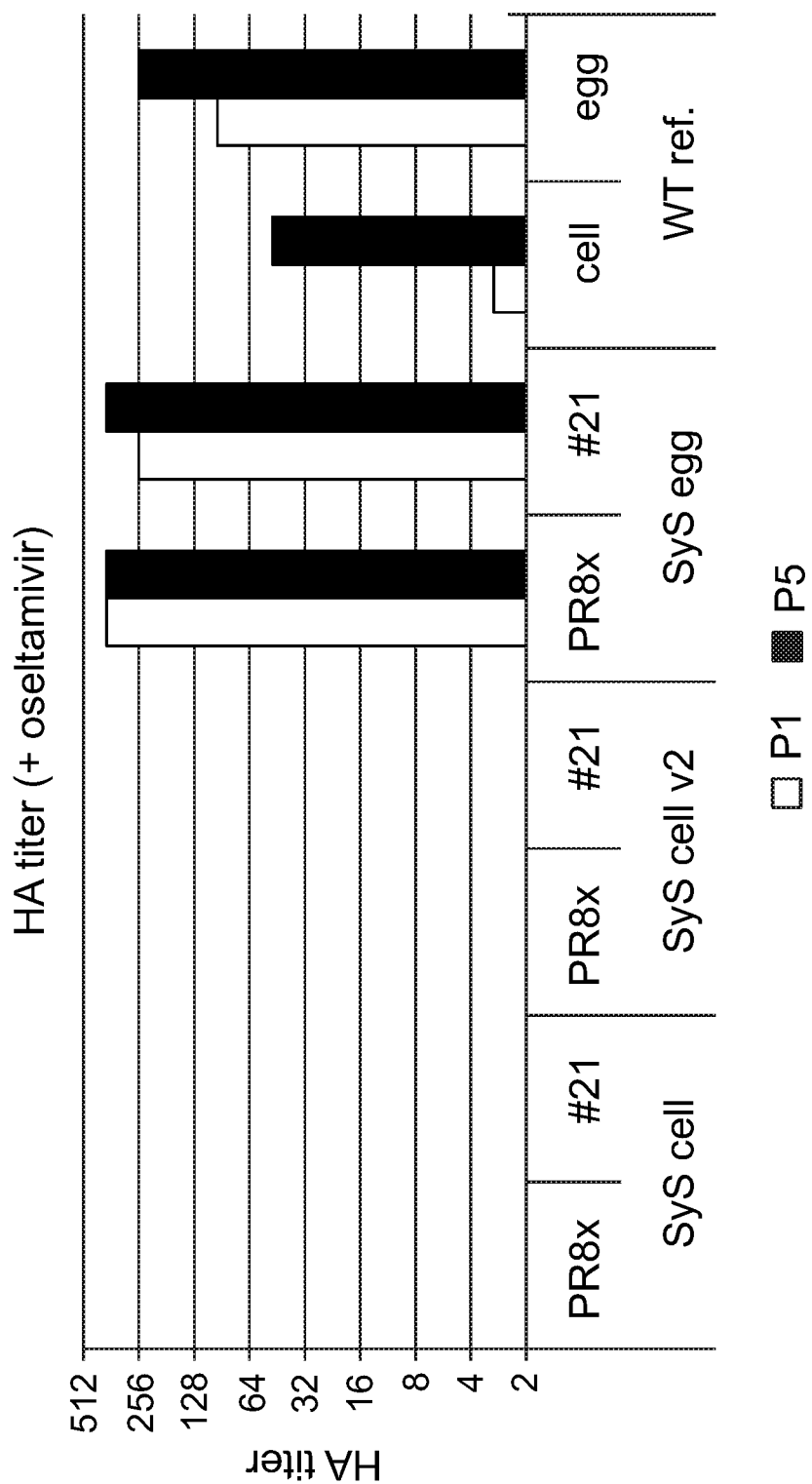
FIG. 4 provides a graph showing HA titers (in the presence of oseltamivir) of 3C.2A viruses that were serially passaged in MDCK cells.

H3N2 viruses have been evolving to not bind red blood cells, as supported in technical difficulties observed in HI assays. In fact, initially a large set of 3C.2A viruses went undetected because of their lack of ability to bind red blood cells (RBCs), which is essential for HI-based early screening, and many of the 3C.2A viruses remain uncharacterized because they cannot be tested by the standard HI assay. Importantly, egg-adapted 3C.2A viruses regain the ability to agglutinate RBCs but lose a key glycosylation and become antigenically mismatched from circulating viruses. FIG. 4 shows HA titer of A/Hong Kong/5738/2014 (3C.2A), which was subjected to serial passages in MDCK cells. The result shows that synthetic, mammalian cell-produced viruses did not gain the ability to agglutinate RBCs after passaging, while wild-type mammalian cell-produced viruses acquired the ability to bind RBCs, which coincides with loss of HA glycosylation site by passage 5. All egg-adapted viruses had HA titers.

Figure 3:
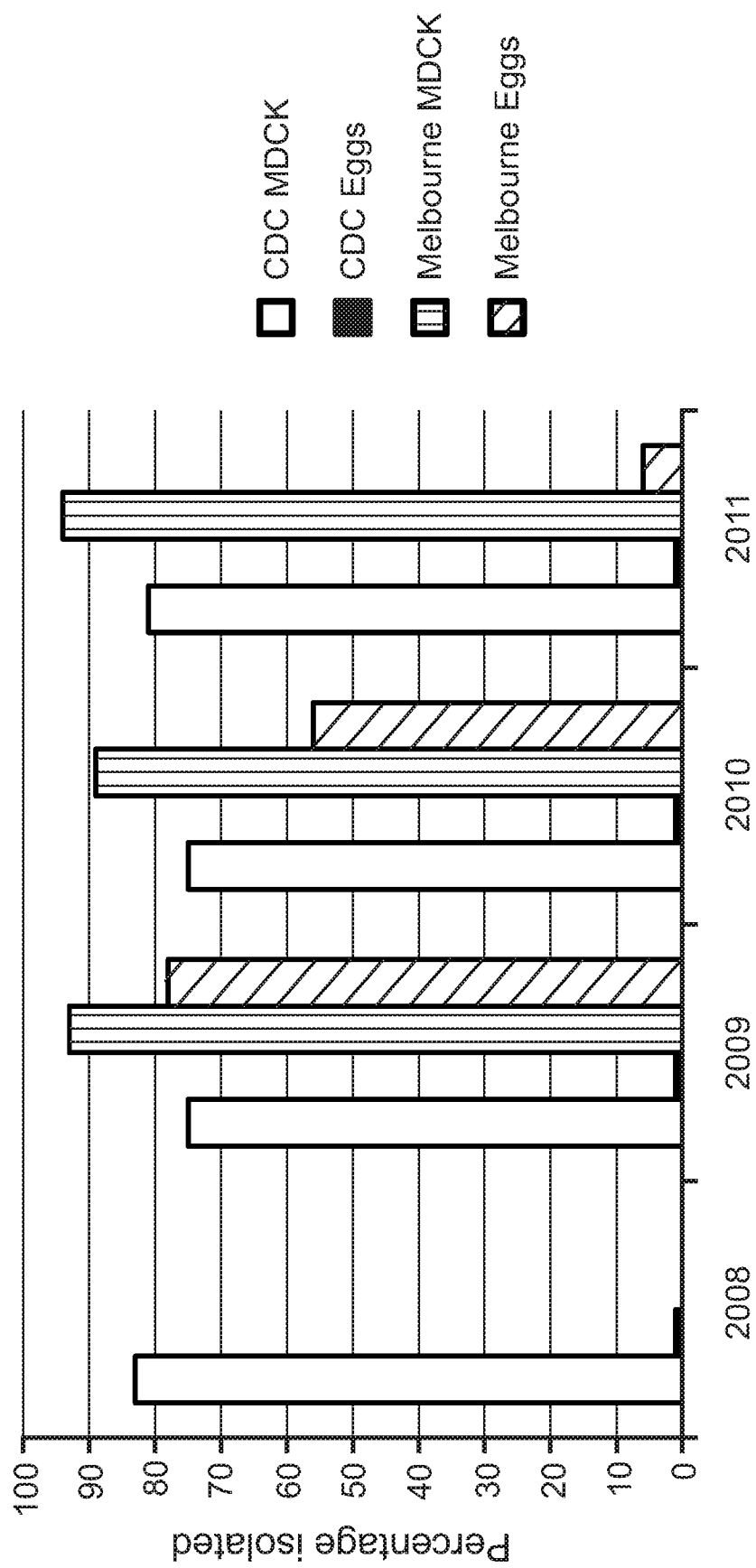
FIG. 3 provides a bar graph depicting H3N2 viral isolation rates in four different systems.

Furthermore, as illustrated in FIG. 3, isolation rate in eggs for H3N2 have been dropping dramatically, while it is still high in cells without cell specific adaptation. In view of these observations and challenges which illustrate unmet needs, the present disclosure provides a solution for better protection against certain influenza viruses, particularly those susceptible to issues associated with egg-based production.

Example 2: Antigenic Characterization of Influenza Viruses Produced Using Synthetic DNA and Novel Backbones It has been appreciated for decades that influenza viruses have a high mutation rate in their RNA genomes and exist as complex quasi-species, a property that facilitates their natural drift and continuously challenges vaccine production. Influenza strains that circulate in humans frequently acquire antigenically important mutations to escape immunological pressure, giving rise to new variants that can become dominant and cause seasonal re-infections. These antigenic changes dictate that the influenza vaccine be reviewed annually and updated almost as often. Vaccination is the most effective strategy to protect against seasonal influenza; however, vaccine performance varies from year to year, with decreased effectiveness associated with mismatches between the vaccine antigens and those of circulating strains (refs. 110-112).

Under the current system, mammalian cells, particularly the MDCK cell line, are a preferred substrate for influenza virus isolation for surveillance activities due to their high sensitivity to infection (ref. 113). However, only influenza viruses that can be re-isolated and propagated exclusively in embryonated hen's eggs are recommended as candidates for both mammalian cell-based and egg-based vaccine manufacturing platforms. This standard practice perpetuates the likelihood of producing a vaccine mismatch.

The variability of virus isolation rates in eggs, particularly for recent H3N2 strains (ref. 114), can limit the number of suitable vaccine candidates available in some years. In 2004, no well-matched H3N2 strain could be isolated in eggs in time to produce a seasonal vaccine, resulting in a substantial vaccine mismatch for that subtype and an associated reduction in vaccine effectiveness (refs. 111 & 115). Furthermore, human-derived influenza viruses propagated in eggs undergo selective pressure and can acquire mutations in HA that alter their affinity from the α-2,6-linked sialic acids that predominate in human respiratory epithelium (ref. 116) to the α-2,3-linked sialic acids that predominate in the egg allantoic cavity (refs. 117 & 118). In recent years, the recommended H3N2 and B-Victoria lineage vaccine viruses have exhibited significantly reduced match to circulating strains due to these egg-adaptive mutations (refs. 110, 119 & 120).

Although evolutionary drift in circulating viruses cannot be controlled, antigenic mismatches introduced as part of current egg-based influenza vaccine production systems can be improved. It is known that influenza viruses propagated in mammalian cells often remain genetically and antigenically similar to the virus present in clinical material (refs. 121-123). Thus, the use of viruses isolated in mammalian cell lines qualified for vaccine production can help maintain antigenic match of the vaccine strain to circulating viruses (ref. 123).

Alternatively, we have developed an efficient synthetic approach for generating high-yielding influenza viruses exclusively in vaccine-qualified MDCK cells (ref. 124). These viruses are produced by reverse-genetics from synthetically-derived nucleic acids based on reported HA and NA sequences and combined with optimized backbone gene segments (ref. 124). These high-growth backbones can increase virus rescue efficiency and increase virus HA yields (ref. 124). The potential utility of these backbones depends in part on their impact on antigenicity. To demonstrate the ability of this synthetic approach to provide viruses that maintain genetic and antigenic match to the intended reference strains, we have performed a study in which the antigenicity of a panel of synthetic viruses covering seasonal A/H1N1, A/H3N2, and B strains was compared to their respective egg- or mammalian cell-grown reference counterparts.

Materials and Methods

Cells and Viruses

MDCK 33016PF cells were maintained as previously described (ref. 124). Wild-type influenza viruses were isolated from clinical samples by World Health Organization (WHO) National Influenza Centers. Egg-based reassortant viruses were generated at WHO Collaborating Centers (WHO CC). All viruses were from stocks held at the Crick Institute, Mill Hill laboratory, UK.

Synthetic DNA

HA and NA segments were assembled as previously described (ref. 124), or with the following modifications. Overlapping oligonucleotides were assembled using primers BMP_13 and BMP_14 (ref. 124). PCR products were denatured and re-annealed to form mismatched duplex DNA, followed by incubation with Surveyor nuclease (Transgenomic, Inc.) and Exonuclease III (NEB). Error-corrected DNA was amplified using nested primers BMP_27

(TTGGGTAACGCCAGGGTTTTCC) (SEQ ID NO: 1) and BMP_34 (TTCACACAGGAAACAGCTATGACCATGATTA) (SEQ ID NO: 2), and purified by ethanol precipitation. Final products are linear gene segments flanked by upstream and downstream regulatory control elements.

Reverse Genetics

Synthetic viruses were generated as previously described (ref. 124). Briefly, synthetic HA and NA gene cassettes and plasmids carrying the six backbone genes (PB2, PB1, PA, NP, M, NS) and the plasmid TMPRSS2 (encoding a serine protease (ref. 125)) were co-transfected into MDCK cells. Clarified culture medium was harvested at least 72 hours post-transfection, and viruses detected by a focus-formation assay (ref. 124). All experiments were performed with viruses rescued and passaged up to 3 times in MDCK cells.

HA amino acid sequences used to generate synthetic viruses are listed below in the standard single-letter format:

A/H1N1/Christchurch/16/2010 (NIB74) - egg
(SEQ ID NO: 3)
MKAILVVLLHTFATANADTLCIGYHANNSTDTVDTVLEKNVTVTHSVNLL
EDKHNGKLCKLRGVAPLHLGKCNIAGWILGNPECESLSTASSWSYIVETS
SSDNGTCYPGNFIDYEELREQLSSVSSFERFEIFPKTSSWPDHDSNKGVT
AACPHAGAKSFYKNLIWLVKKGNSYPTLSKSYINDKGKEVLVLWGIHHPS
TSADQQSLYQNADAYVFVGTSRYSKKFKPETAIRPKVRNQEGRMNYYWTL
VEPGDKITFEATGNLVAPRYAFAMERNAGSGIIISDTPVHDCNTTCQTPK
GAINTSLPFQNIHPITIGKCPKYVKSTKLRLATGLRNVPSIQSRGLFGAI
AGFIEGGWTGMVDGWYGYHHQNEQGSGYAADLKSTQNAIDKITNKVNSVI
EKMNTQFTAVGKEFNHLEKRIENLNKKVDDGFLDIWTYNAELLVLLENER
TLDYHDSNVKNLYEKVRSQLKNNAKEIGNGCFEFYHKCDNTCMESVKNGT
YDYPKYSEEAKLNREEIDGVKLESTRIYQILAIYSTVASSLVLVVSLGAI
SFWMCSNGSLQCRICI A/H3N2/Victoria/210/2009 (X187) - egg
(SEQ ID NO: 4)
MKTIIALSYILCLVFAQKLPGNDNSTATLCLGHHAVPNGTIVKTITNDQI
EVTNATELVQNSSTGEICDSPHQILDGKNCTLIDALLGDPQCDGFQNKKW
DLFVERSKAYSNCYPYDVPDYASLRSLVASSGTLEFNNESFNWTGVTQNG
TSSACIRRSKNSFFSRLNWLTHLNFKYPALNVTMPNNEQFDKLYIWGVHH
PVTDKDQIFLYAQASGRITVSTKRSQQTVIPNIGSRPRVRNIPTRISIYW
TIVKPGDILLINSTGNLIAPRGYFKMQSGKSSIMRSDAPIGKCNSECITP
NGSIPNDKPFQNVNRITYGACPRYVKQNTLKLATGMRNVPEKQTRGIFGA
IAGFIENGWEGMVDGWYGFRHQNSEGRGQAADLKSTQAAIDQINGKLNRL
IGKTNEKFHQIEKEFSEVEGRIQDLEKYVEDTKIDLWSYNAELLVALENQ
HTIDLTDSEMNKLFEKTKKQLRENAEDMGNGCFKIYHKCDNACIGSIRNG
TYDHNVYRDEALNNRFQIKGVELKSGYKDWILWISFAISCFLLCVALLGF
IMWACQKGNIRCNICI A/H3N2/Victoria/210/2009 - mammalian cell
(SEQ ID NO: 5)
MKTIIALSYILCLVFAQKLPGNDNSTATLCLGHHAVPNGTIVKTITNDQI
EVTNATELVQNSSTGEICDSPHQILDGKNCTLIDALLGDPQCDGFQNKKW
DLFVERSKAYSNCYPYDVPDYASLRSLVASSGTLEFNNESFNWTGVTQNG
TSSACIRRSKNSFFSRLNWLTHLNFKYPALNVTMPNNEQFDKLYIWGVHH
PGTDKDQIFLYAQASGRITVSTKRSQQTVIPNIGSRPRVRNIPSRISIYW
TIVKPGDILLINSTGNLIAPRGYFKMQSGKSSIMRSDAPIGKCNSECITP
NGSIPNDKPFQNVNRITYGACPRYVKQNTLKLATGMRNVPEKQTRGIFGA
IAGFIENGWEGMVDGWYGFRHQNSEGRGQAADLKSTQAAIDQINGKLNRL
IGKTNEKFHQIEKEFSEVEGRIQDLEKYVEDTKIDLWSYNAELLVALENQ
HTIDLTDSEMNKLFEKTKKQLRENAEDMGNGCFKIYHKCDNACIGSIRNG
TYDHDVYRDEALNNRFQIKGVELKSGYKDWILWISFAISCFLLCVALLGF
IMWACQKGNIRCNICI A/H3N2/Victoria/361/2011 (IVR165) - egg
(SEQ ID NO: 6)
MKTIIALSHILCLVFAQKLPGNDNSTATLCLGHHAVPNGTIVKTITNDQI
EVTNATELVQNSSIGEICDSPHQILDGENCTLIDALLGDPQCDGFQNKKW
DLFVERSKAYSNCYPYDVPDYASLRSLVASSGTLEFNNESFNWTGVTQNG
TSSACIRRSNNSFFSRLNWLTQLNFKYPALNVTMPNNEQFDKLYIWGVHH
PVTDKDQIFLYAQSSGRITVSTKRSQQAVIPNIGYRPRIRNIPSRISIYW
TIVKPGDILLINSTGNLIAPRGYFKIRSGKSSIMRSDAPIGKCNSECITP
NGSIPNDKPFQNVNRITYGACPRYVKQSTLKLATGMRNVPEKQTRGIFGA
IAGFIENGWEGMVDGWYGFRHQNSEGRGQAADLKSTQAAIDQINGKLNRL
IGKTNEKFHQIEKEFSEVEGRIQDLEKYVEDTKIDLWSYNAELLVALENQ
HTIDLTDSEMNKLFEKTKKQLRENAEDMGNGCFKIYHKCDNACIGSIRNG
TYDHDVYRDEALNNRFQIKGVELKSGYKDWILWISFAISCFLLCVALLGF
IMWACQKGNIRCNICI A/H3N2/Victoria/361/2011 - mammalian cell
(SEQ ID NO: 7)
MKTIIALSHILCLVFAQKLPGNDNSTATLCLGHHAVPNGTIVKTITNDQI
EVTNATELVQNSSIGEICDSPHQILDGENCTLIDALLGDPQCDGFQNKKW
DLEVERSKAYSNCYPYDVPDYASLRSLVASSGTLEFNNESFNWTGVTQNG
TSSACIRRSNNSFFSRLNWLTHLNFKYPALNVTMPNNEQFDKLYIWGVHH
PGTDKDQIFLYAQSSGRITVSTKRSQQAVIPNIGSRPRIRNIPSRISIYW
TIVKPGDILLINSTGNLIAPRGYFKIRSGKSSIMRSDAPIGKCNSECITP
NGSIPNDKPFQNVNRITYGACPRYVKQSTLKLATGMRNVPEKQTRGIFGA
IAGFIENGWEGMVDGWYGFRHQNSEGRGQAADLKSTQAAIDQINGKLNRL
IGKTNEKFHQIEKEFSEVEGRIQDLEKYVEDTKIDLWSYNAELLVALENQ
HTIDLTDSEMNKLFEKTKKQLRENAEDMGNGCFKIYHKCDNACIGSIRNG
TYDHDVYRDEALNNRFQIKGVELKSGYKDWILWISFAISCFLLCVALLGF
IMWACQKGNIRCNICI A/H3N2/Texas/50/2012 - egg
(SEQ ID NO: 8)
MKTIIALSYILCLVFAQKLPGNDNSTATLCLGHHAVPNGTIVKTITNDRI
EVTNATELVQNSSIGEICDSPHQILDGENCTLIDALLGDPQCDGFQNKKW
DLFVERSKAYSNCYPYDVPDYASLRSLVASSGTLEFNNESFNWNGVTQNG
TSSACIRRSNNSFFSRLNWLTHLNFKYPALNVTMPNNEQFDKLYIWGVHH -continued

PVTDKDQIFLYAQPSGRITVSTKRSQQAVIPNIGFRPRIRNIPSRISIYW

TIVKPGDILLINSTGNLIAPRGYFKIRSGKSSIMRSDAPIGKCKSECITP

NGSIPNDKPFQNVRITYGACPRYVKQSTLKLATGMRNVPEKQTRGIFGA

IAGFIENGWEGMVDGWYGFRHQNSEGRGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFAISCFLLCVALLGF

IMWACQKGNIRCNICI

A/H3N2/Texas/50/2012 - mammalian cell
(SEQ ID NO: 9)
MKTIIALSYILCLVFAQKLPGNDNSTATLCLGHHAVPNGTIVKTITNDRI

EVTNATELVQNSSIGEICDSPHQILDGENCTLIDALLGDPQCDGFQNKKW

DLFVERSKAYSNCYPYDVPDYASLRSLVASSGTLEFNNESFNWNGVTQNG

TSSACIRRSNNSFFSRLNWLTHLNFKYPALNVTMPNNEQFDKLYIWGVHH

PGTDKDQIFLYAQPSGRITVSTKRSQQAVIPNIGSRPRIRNIPSRISIYW

TIVKPGDILLINSTGNLIAPRGYFKIRSGKSSIMRSDAPIGKCKSECITP

NGSIPNDKPFQNVRITYGACPRYVKQSTLKLATGMRNVPEKQTRGIFGA

IAGFIENGWEGMVDGWYGFRHQNSEGRGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFAISCFLLCVALLGF

IMWACQKGNIRCNICI

A/H3N2/Uruguay/716/2007 (X175C) - egg
(SEQ ID NO: 10)
MKTIIALSYILCLVFAQKLPGNDNSTATLCLGHHAVPNGTIVKTITNDQI

EVTNATELVQSSSTGEICDSPHQILDGENCTLIDALLGDPQCDGFQNKKW

DLFVERSKAYSNCYPYDVPDYASLRSLVASSGTLEFNNESFNWTGVTQNG

TSSSCIRGSNNSFFSRLNWLTHLNFKYPALNVTMPNNEKFDKLYIWGVHH

PGTDNDQIFPYAQASGRITVSTKRSQQTVIPNIGSRPRVRNIPSRISIYW

TIVKPGDILLINSTGNLIAPRGYFKIRSGKSSIMRSDAPIGKCNSECITP

NGSIPNDKPFQNVRITYGACPRYVKQNTLKLATGMRNVPEKQTRGIFGA

IAGFIENGWEGMVDGWYGFRHQNSEGIGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFAISCFLLCVALLGF

IMWACQKGNIRCNICI

A/H3N2/Brisbane/299/2011 (IVR164) - egg
(SEQ ID NO: 11)
MKTIIALSYILCLVFAQKLPGNDNSTATLCLGHHAVPNGTIVKTITNDQI

EVTNATELVQSSSTGEICNSPHQILDGENCTLIDALLGDPQCDGFQNKKW

DLFVERSKAHSNCYPYDVPDYASLRSLVASSGTLEFNNESFNWTGVTQNG

TSSSCIRRSNNSFFSRLNWLTHLNFKYPALNVTMPNNEQFDKLYIWGVHH

PDTDKGQIFLYAQAAGRITVSTKRSQQAVIPNVGFRPRVRNIPSRVSIYW

TIVKPGDILLINSTGNLIAPRGYFKIRSGKSSIMRSDAPIGKCNSACITP

NGSIPTDKPFQNVRITYGACPRYVKQNTLKLATGMRNVPEKKTRGIFGA

IAGFIENGWEGMVDGWYGFRHQNSEGRGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFAISCFLLCVALLGF

IMWACQKGNIRCNICI

A/H3N2/Berlin/93/2011 - egg
(SEQ ID NO: 12)
MKTIIALSYILCLVFAQKLPGNDNSTATLCLGHHAVPNGTIVKTITNDRI

EVTNATELVQNSSIGEICDSPHQILDGENCTLIDALLGDPQCDGFQNKKW

DLFVERSKAYSNCYPYDVPDYASLRSLVASSGTLEFNNESFNWTGVTQNG

TSSACIRRSNNSFFSRLNWLTRLNFKYPALNVTMPNNEQFDKLYIWGVHH

PGTDKDQIFLYAQSSGRITVSTKRSQQAVIPNIGSRPRIRNIPSRISIYW

TIVKPGDILLINSTGNLIAPRGYFKIRSGKSSIMRSDAPIGKCKSECITP

NGSIPNDKPFQNVRITYGACPRYVKQSTLKLATGMRNVPEKQTRGIFGA

IAGFIENGWEGMVDGWYGFRHQNSEGRGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFATSCFLLCVALLGF

IMWACQKGNIRCNICI

A/H3N2/SouthAustralia/3/2011 - mammalian cell
(SEQ ID NO: 13)
MKTIIALSYILCLVFAQKLPGNDNSTATLCLGHHAVPNGTIVKTITNDQI

EVTNATELVQNSSIGEICDSPHQILDGENCTLIDALLGDPQCDGFQNKKW

DLFVERSKAYSNCYPYDVPDYASLRSLVASSGTLEFNNESFNWTGVTQNG

TSSACIRRSNNSFFSRLNWLTHLNFKYPALNVTMPNNEQFDKLYIWGVHH

PGTDKDQIFLYAQSSGRITVSTKRSQQAVIPNIGSRPRIRNIPSRISIYW

TIVKPGDILLINSTGNLIAPRGYFKIRSGKSSIMRSDAPIGKCNSECITP

NGSIPNDKPFQNVRITYGACPRYVKQSTLKLATGMRNVPEKQTRGIFGA

IAGFIENGWEGMVDGWYGFRHQNSEGRGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFAISCFLLCVALLGF

IMWACQKGNIRCNICI

A/H3N2/Switzerland/9715293/2013 - mammalian cell
(SEQ ID NO: 14)
MKTIIALSYILCLVFAQKLPGNDNSTATLCLGHHAVPNGTIVKTITNDRI

EVINATELVQNSSIGEICDSPHQILDGENCTLIDALLGDPQCDGFQNKKW

DLFVERSKAYSNCYPYDVPDYASLRSLVASSGTLEFNNESFNWAGVTQNG

TSSSCIRGSNSSFFSRLNWLTHLNSKYPALNVTMPNNEQFDKLYIWGVHH

PGTDKDQIFLYAQSSGRITVSTKRSQQAVIPNIGSRPRIRDIPSRISIYW

TIVKPGDILLINSTGNLIAPRGYFKIRSGKSSIMRSDAPIGKCKSECITP

NGSIPNDKPFQNVRITYGACPRYVKQSTLKLATGMRNVPERQTRGIFGA

-continued

IAGFIENGWEGMVDGWYGFRHQNSEGRGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFAISCFLLCVALLGF

IMWACQKGNIRCNICI

A/H3N2/Switzerland/9715293/2013 - egg
(SEQ ID NO: 15)
MKTIIALSYILCLVFAQKLPGNDNSTATLCLGHHAVPNGTIVKTITNDRI

EVTNATELVQNSSIGEICDSPHQILDGENCTLIDALLGDPQCDGFQNKKW

DLEVERSKAYSNCYPYDVPDYASLRSLVASSGTLEFNNESFNWAGVTQNG

TSSSCRRGSNSSFFSRLNWLTHLNSKYPALNVTMPNNEQFDKLYIWGVHH

PVTDKDQIFLYAQSSGRITVSTKRSQQAVIPNIGSRPRIRDIPSRISIYW

TIVKPGDILLINSTGNLIAPRGYFKIRSGKSSIMRSDAPIGKCKSECITP

NGSIPNDKPFQNVNRITYGACPRYVKQSTLKLATGMRNVPERQTRGIFGA

IAGFIENGWEGMVDGWYGFRHQNSEGRGQAADLKSTQAAIDQINGKLNRL

IGKTNEKFHQIEKEFSEVEGRIQDLEKYVEDTKIDLWSYNAELLVALENQ

HTIDLTDSEMNKLFEKTKKQLRENAEDMGNGCFKIYHKCDNACIGSIRNG

TYDHDVYRDEALNNRFQIKGVELKSGYKDWILWISFAISCFLLCVALLGF

IMWACQKGNIRCNICI

B/Brisbane/60/2008 - egg
(SEQ ID NO: 16)
MKAIIVLLMVVTSNADRICTGITSSNSPHVVKTATQGEVNVTGVIPLTTT

PTKSHFANLKGTETRGKLCPKCLNCTDLDVALGRPKCTGKIPSARVSILH

EVRPVTSGCFPIMHDRTKIRQLPNLLRGYEHIRLSTHNVINAENAPGGPY

KIGTSGSCPNITNGNGFFATMAWAVPKNDKNKTATNPLTIEVPYICTEGE

DQITVWGFHSDNEAQMAKLYGDSKPQKFTSSANGVTTHYVSQIGGFPNQT

EDGGLPQSGRIVVDYMVQKSGKTGTITYQRGILLPQKVWCASGRSKVIKG

SLPLIGEADCLHEKYGGLNKSKPYYTGEHAKAIGNCPIWVKTPLKLANGT

KYRPPAKLLKERGFFGAIAGFLEGGWEGMIAGWHGYTSHGAHGVAVAADL

KSTQEAINKITKNLNSLSELEVKNLQRLSGAMDELHNEILELDEKVDDLR

ADTISSQIELAVLLSNEGIINSEDEHLLALERKLKKMLGPSAVEIGNGCF

ETKHKCNQTCLDRIAAGTFDAGEFSLPTFDSLNITAASLNDDGLDNHTIL

LYYSTAASSLAVTLMIAIFVVYMVSRDNVSCSICL

B/Brisbane/60/2008 - mammalian cell
(SEQ ID NO: 17)
MKAIIVLLMVVTSNADRICTGITSSNSPHVVKTATQGEVNVTGVIPLTTT

PTKSHFANLKGTETRGKLCPKCLNCTDLDVALGRPKCTGKIPSARVSILH

EVRPVTSGCFPIMHDRTKIRQLPNLLRGYEHIRLSTHNVINAENAPGGPY

KIGTSGSCPNITNGNGFFATMAWAVPKNDKNKTATNPLTIEVPYICTEGE

DQITVWGFHSDNETQMAKLYGDSKPQKFTSSANGVTTHYVSQIGGFPNQT

EDGGLPQSGRIVVDYMVQKSGKTGTITYQRGILLPQKVWCASGRSKVIKG

SLPLIGEADCLHEKYGGLNKSKPYYTGEHAKAIGNCPIWVKTPLKLANGT

KYRPPAKLLKERGFFGAIAGFLEGGWEGMIAGWHGYTSHGAHGVAVAADL

KSTQEAINKITKNLNSLSELEVKNLQRLSGAMDELHNEILELDEKVDDLR

ADTISSQIELAVLLSNEGIINSEDEHLLALERKLKKMLGPSAVEIGNGCF

ETKHKCNQTCLDRIAAGTFDAGEFSLPTFDSLNITAASLNDDGLDNHTIL

LYYSTAASSLAVTLMIAIFVVYMVSRDNVSCSICL

Virus Sequencing

Viral RNA was extracted using the QIAamp Viral RNA Mini Kit (Qiagen) and cDNA generated using Monsterscript reverse transcriptase (Epicentre). HA and NA genes were amplified using Platinum PCR SuperMix High Fidelity DNA polymerase (Life Technologies), and sequences analyzed by Sanger DNA sequencing.

Hemagglutination Inhibition (HI) Assays

Hemagglutination and HI assays were performed according to standard WHO methods by using 0.1% suspensions of guinea pig red blood cells and 20 nM oseltamivir carboxylate. HA titers were determined in the presence of drug. HI titers were reciprocals of the highest dilutions of sera that inhibited hemagglutination. Post-infection ferret antisera against various reference viruses were treated with receptor-destroying enzyme from *Vibrio cholera*.

Ferret Inoculation

Post-infection antisera were produced in ferrets (*Mustela putorius* furo) following intranasal instillation of diluted virus under light sedation and sera were collected under terminal anaesthesia at the Crick Institute Mill Hill laboratory under UK Home Office project license PPL/80/2541 or were made by the National Institute for Biological Standards and Control, UK, under UK Home Office project license PIL/80/2530. Other antisera were from the WHO CC at the Centers for Disease Prevention and Control, Atlanta, Ga., St Jude's Children's Research Hospital, Memphis, Tenn., and the Peter Doherty Institute for Infection & Immunity, Melbourne, Australia.

Results

Generation of Synthetic Viruses

Synthetic and reverse genetic technologies enable the selection of genomes to generate a new vaccine virus, based on known virus sequences. Three optimized backbones (PR8x, #19, and #21) derived from low pathogenicity viruses (ref. 124) were used to make subtype A viruses. The PR8x backbone contains six internal genome segments from an MDCK-adapted A/Puerto Rico/8/1934 strain. The #19 backbone contains PB2, PB1, and NP from an MDCK-adapted A/Hessen/105/2007 strain and the remaining segments from PR8x. The #21 backbone contains an A/California/07/2009 PB1 and the remaining segments from PR8x. Subtype B viruses were made using all six backbone segments from B/Brisbane/60/2008. Rescued viruses were passaged up to three times in MDCK cells exclusively. The HA and NA genomes of all viruses were confirmed to have 100% genetic identity to the coding sequences used for synthesis (sequences provided above). Viruses generated for antigenicity testing covered seasonal influenza strains (A/H1N1, A/H3N2, and B-Victoria lineage), including four egg- and mammalian cell-derived matched pairs (FIG. 5). The H3N2 subtype was prioritized in this study given that H3N2 candidate vaccine viruses (CCVs) used in vaccine production have failed to match circulating strains for the past several years and continue to present a challenge.

Antigenic Characterization of Synthetic Viruses

Figure 6:
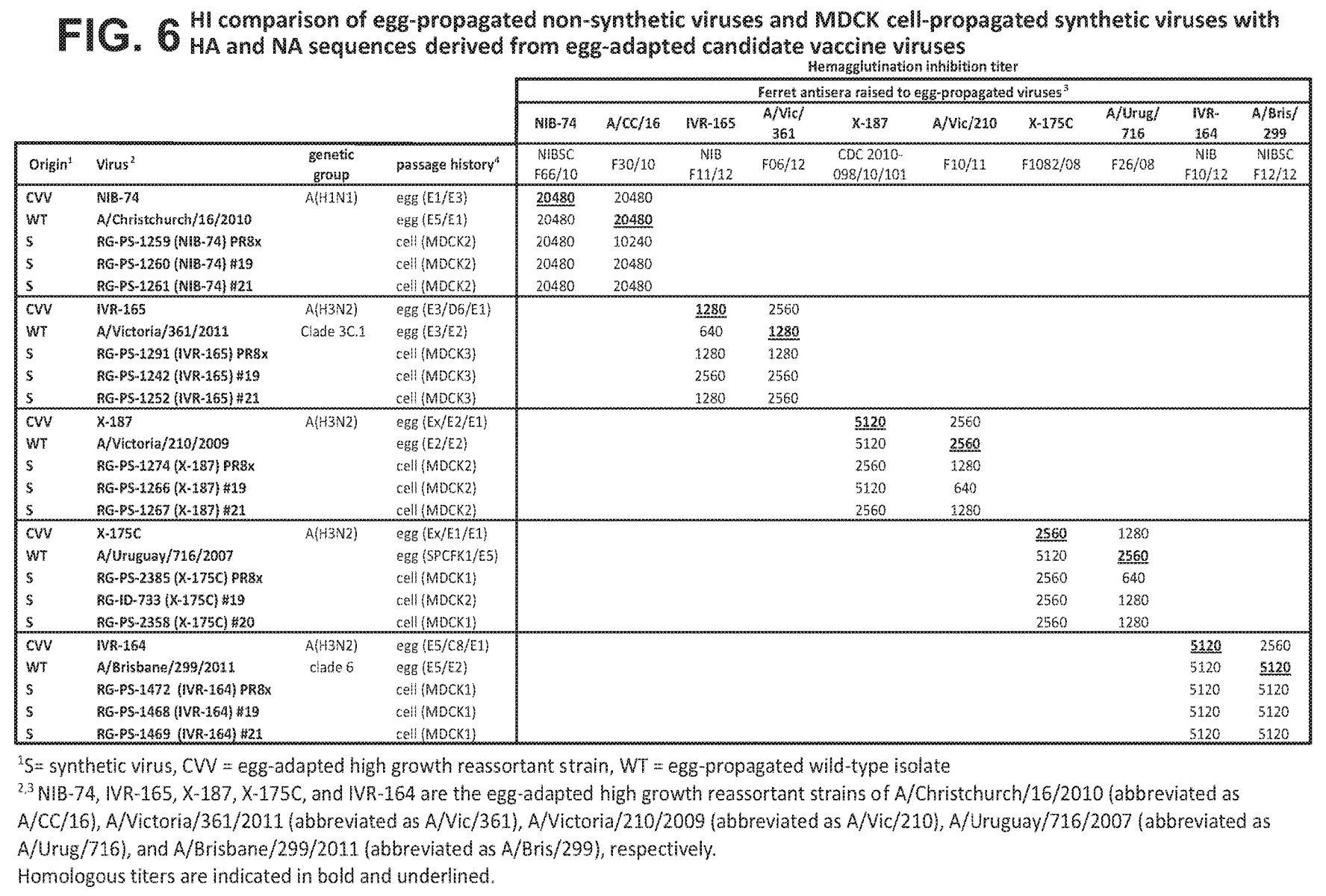

We first demonstrated that this MDCK cell-based synthetic technology could generate viruses that are antigenically similar to conventional egg-adapted CVVs, even though the synthetic viruses were never passaged in eggs. Synthetic viruses were made using HA and NA sequences from five egg-adapted, high-growth, reassortant CVVs (NIB-74, X-187, IVR-165, X-175, or IVR-164), and the antigenicity of the viruses was tested by a one-way HI assay using ferret antisera raised against the egg-adapted CVVs or the corresponding egg-adapted wild-type isolates (FIG. 6). For all five strains tested, antisera raised against the CVVs recognized the corresponding synthetic viruses at titers 2-fold different from the homologous virus titers, regardless of the backbone used. All the synthetic viruses also reacted similarly in HI assays with ferret antiserum raised against the egg-adapted wild-type strains, with titers 4-fold different from the homologous virus titers.

Because we aim to generate CVVs directly on high-growth backbones that antigenically match any newly isolated wild-type strain, we extended our analysis to use HA and NA sequences from H3N2 wild-type isolates, rather than high-growth reassortants. Synthetic viruses were made using HA and NA sequences from two mammalian cell-grown, wild-type isolates, A/Victoria/210/2009 and A/South Australia/3/2011, and from two egg-adapted strains, A/Texas/50/2012 and A/Berlin/93/2011 (FIG. 7). After one passage in MDCK cells, antigenic characterization was performed by HI tests using ferret antisera raised against the cell- or egg-propagated wild-type strains. Viruses made with the different backbones reacted similarly to a given antiserum, and HI titers obtained from all the tested viruses were within ≤4-fold of the homologous virus titer.

Synthetic Viruses can Improve Match to Strains that Cause Human Disease

Synthetic viruses can be made using HA and NA sequences from either egg- or mammalian cell-grown isolates, but the ability to match a mammalian cell-grown virus genetically can be expected to improve antigenic match to strains circulating in the human population. It has been documented that egg-selected changes in the HA gene for the recent H3N2 and B-Victoria lineage CVVs used in seasonal vaccines have been associated with reduced vaccine effectiveness (refs. 110 & 119). Therefore, we used synthetic technology to assess differences in antigenicity between mammalian cell- and egg-derived matched antigens for three recent H3N2 strains and one B-Victoria lineage strain. In the northern hemisphere, A/Victoria/210/2009 was the H3N2 component for the 2010-11 and 2011-12 vaccines; A/Victoria/361/2011-like was the H3N2 component for the 2012-13 and 2013-14 vaccines; and A/Switzerland/9715293/2013 was the H3N2 recommendation for the 2015-16 vaccine. B/Brisbane/60/2008 was the B strain component for the 2009-10, 2010-11, and 2011-12 trivalent vaccines, and has been the B-Victoria component for quadrivalent vaccines since 2012-13. The HA sequences of all mammalian cell- and egg-derived antigen pairs differed by 1-3 amino acids (see Table 2 below).

TABLE 2

Sequence differences in synthetic egg- and mammalian cell-derived antigen-matched pairs.

| | position | cell | egg |
|---|---|---|---|
| A/H3N2/Victoria/210/2009 | 186 | G | V |
| | 228 | S | T |
| A/H3N2/Victoria/361/2011 | 156 | H | Q |
| | 186 | G | V |
| | 219 | S | Y |
| A/H3N2/Texas/50/2012 | 186 | G | V |
| | 219 | S | F |
| A/H3N2/Switzerland/9715293/2013 | 140 | I | R |
| | 186 | G | V |
| B/Brisbane/60/2008 | 199 | T | A |

Notably, all the egg-derived H3 antigens contained a G186V mutation that improves virus growth in eggs but alters antigenicity relative to an MDCK cell-propagated virus (ref. 126). The egg-derived B/Brisbane/60/2008 HA loses a potential glycosylation site near the receptor binding site. The loss of this glycan upon egg adaptation affects antigenicity (ref. 119).

Figure 8:
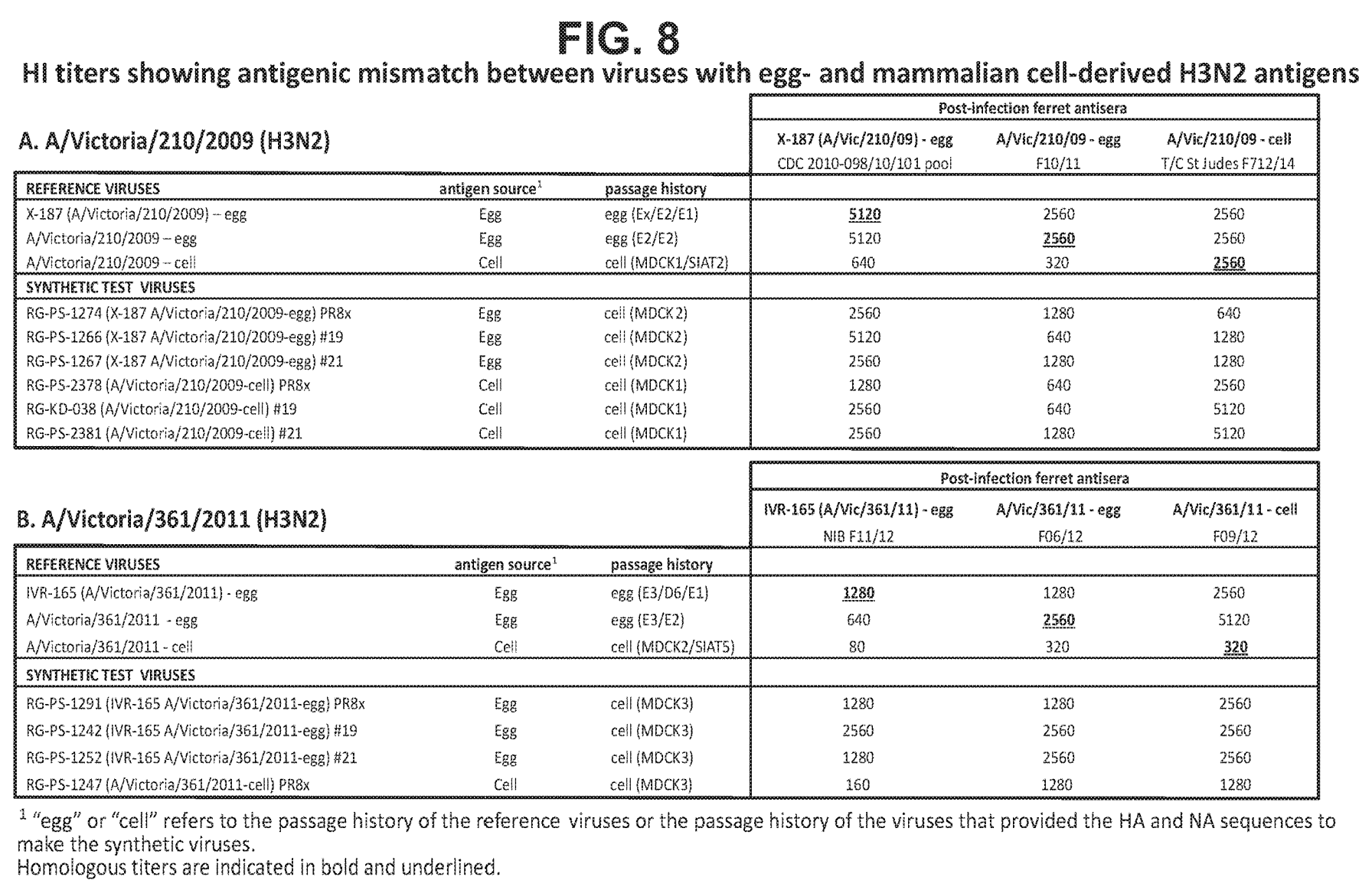

Synthetic viruses made from either mammalian cell- or egg-derived HA and NA sequences were compared by HI assay to their matched synthetic counterpart and to conventional reference strains using antisera raised against mammalian cell- and egg-grown reference viruses. As shown in FIGS. 8 and 9, in most instances we observed differences in reactivity between the cell- and egg-derived antigens when analyzed with ferret antisera raised against the egg-grown viruses, but not when analyzed with antisera raised against the mammalian cell-grown viruses. In particular, ferret antisera raised against the egg-grown vaccine viruses generally recognized synthetic test viruses containing the egg-adapted HA sequence at a titer within 2-fold of the homologous titers, but reacted less well in HI assays (>4-fold decrease) to all viruses expressing the corresponding mammalian cell-derived antigens. This experimental design models the current human immunization situation, in which an immune response against an egg-derived vaccine antigen is intended to protect against circulating strains that lack egg adaptations. However, ferret antisera raised against the cell-grown isolates recognized viruses expressing either the cell- or egg-derived antigens. Most viruses reacted to a given antiserum raised against mammalian cell grown viruses within ≤4-fold of the corresponding homologous titer, with the exception of the antiserum that was raised against the cell-grown A/Victoria/361/2011 virus, which produced a low homologous titer of 320 but reacted much better (>4-fold increase) to viruses expressing the egg-adapted antigens (FIG. 8B). This surprising finding may be attributed to differences in receptor avidity between egg-adapted and cell-grown viruses, which could affect the dynamics of the HI assay. Since recent cell-grown H3N2 viruses appear to have a lower avidity for the sialic acid receptor, more cell-grown A/Victoria/361/2011 virus may have been used in the HI assay to get 4 HA units compared to the egg-adapted viruses, requiring more antibody to inhibit binding to red blood cells.

The mismatch observed between egg- and mammalian cell-grown A/Switzerland/9715293/2013 reference viruses by one-way HI testing (FIG. 10) prompted us to select this 2015-16 vaccine strain for additional two-way antigenic characterization. Ferret antisera raised against two synthetic viruses expressing either the mammalian cell- or egg-derived antigen were tested with conventional reference strains and with synthetic viruses made on different backbones (FIG. 10). The two-way HI data confirmed that the synthetic viruses were antigenically similar to their corresponding reference strains, with HI titer differences within 2-fold.

Ferret antisera raised against viruses with one backbone also effectively recognized viruses rescued on a different backbone, confirming that the use of alternative backbones with the same HA and NA sequence does not alter antigenicity. Interestingly, the cell-derived synthetic and wild-type antigens reacted better to antiserum raised to the synthetic virus expressing egg-adapted HA (RG-PS-2404) than to antiserum raised to the egg-adapted reference virus 2-fold versus 4 to 8-fold lower than the homologous titers, respectively). It is plausible that high growth backbones affect the amount of HA that gets incorporated and presented on the virion surface, which could affect the avidity of the viruses for red blood cells and/or the amount of antibodies elicited by ferret infection with such viruses. Both of these factors could impact the dynamics of the HI assay and are under investigation. Overall, we demonstrated the ability of synthetic technology to generate viruses that are a better match to the mammalian cell-grown prototype compared to current egg-adapted vaccine viruses.

Discussion

Reports of antigenic mismatch between recommended vaccine viruses and circulating viruses in recent years, particularly for H3N2 strains (refs. 110-112, 119 & 120), has heightened public awareness and concern over the effectiveness of seasonal influenza vaccines. This concern highlights the need for an improved CVV generation system that is not reliant on legacy, egg-based technology. Antigenic mismatches may result from antigenic drift in circulating viruses, egg-adaptive mutations, or both. Between 2010-14, HA mutations in the egg-adapted H3N2 vaccine strains resulted in antigenic mismatch with circulating strains and was associated with low vaccine effectiveness (refs. 110 & 119). In 2014-15, the drifted H3N2 strain A/Texas/50/2012 vaccine strain was antigenically distinct from dominant circulating strains (refs. 112 & 120). Furthermore, variability of H3N2 influenza virus isolation rates in eggs in recent years (refs. 127 & 128) can add additional risk of mismatch to the current system. Therefore, the use of CVVs isolated or synthetically generated in certified mammalian cells could help increase the number of viruses available for vaccine virus selection and, in some circumstances, provide better matched viruses for vaccine manufacture.

MDCK cells have both α-2, 6- and α-2, 3-linked sialic acids on their surfaces, making them a more neutral substrate with respect to selection of altered variants of influenza virus (ref. 117). Sequence analysis of influenza viruses in clinical samples and their laboratory-passaged derivatives have confirmed that MDCK cells are more likely than chicken eggs to maintain the prevalent HA genotypes present in clinical material (ref. 122). MDCK cell-grown viruses are also more antigenically similar to the viruses replicating in humans than their egg-grown counterparts, as evidenced by their greater recognition by neutralizing and HI antibodies in post-infection human sera (refs. 129 & 130).

To that end, we have established a synthetic system for generating vaccine viruses exclusively in MDCK cells from sequence information (ref. 124). This system has the potential to improve matching to strains that cause human disease. For each new type A virus, a set of high-growth backbones can be tested empirically to identify the highest-yielding backbone for that particular HA and NA in mammalian cells and eggs. The backbones that we have established for type A viruses can increase virus rescue efficiency in MDCK cells and HA yields in both MDCK cells and in eggs (ref. 124). This synthetic technology, combined with a standard PR8 backbone, has already been used to produce an H7N9 vaccine candidate that had a good safety profile and elicited antibody titers considered protective in a phase I trial (ref. 131). To facilitate the use of higher yielding chimeric backbones to produce CVVs for human vaccines, we have sought to demonstrate that the use of alternative backbones does not alter the antigenicity of synthetic vaccine viruses.

In this study, we have shown that the synthetic system allows control over genome selection and the resulting antigenicity of a new vaccine virus. Synthetic viruses could be made to antigenically match either egg- or mammalian cell-propagated isolates, based on the HA and NA sequences chosen for gene synthesis. Seasonal viruses generated with synthetic DNA and alternative backbones were passaged up to three times in a vaccine-approved MDCK cell line, and antigenic stability was established by HI titers comparable to those of the corresponding conventional reference strains. In particular, we showed that using different backbones to generate a virus with the same HA and NA sequence did not alter antigenicity.

Although viruses passaged in MDCK cells generally do not acquire adaptive mutations in HA, some H3N2 viruses (which may have HA molecules with low affinity for cell surface sialic acid) have been reported to acquire upon passage a mutation in the NA sialic acid binding site that facilitates binding to MDCK cells (ref. 132). Although the selected NA mutation does not interfere with the antigenic and immunogenic properties of the mutated viruses, per se, the altered properties of NA result in NA-mediated hemagglutination and consequent changes to HI titers. To block this NA-mediated hemagglutination, the NA inhibitor oseltamivir was added to the HI assays for all H3N2 strains in the studies we are reporting.

The ability of synthetic seed technology to increase the number of strains with new HAs and NAs that can be isolated and to provide strains that are more similar to a mammalian cell-grown prototype virus may improve vaccine match to strains circulating in humans. In addition, the ability to generate these candidate viruses rapidly using this technology compared to egg-based reassortment (ref. 124) could potentially allow strain recommendations to be made later, thus reducing the lag time between strain selection and vaccine distribution during which antigenic drift may occur. The relative clinical effectiveness of vaccines made with better matched strains still need to be determined. Based on the current data, we can conclude that the use of non-egg-based platforms, such as mammalian cells, for generating vaccine viruses and for antigen manufacture could improve the level of vaccine antigenic match to circulating strains.

Example 3: Exploring Serological Cross-Reactivity of Mouse Antisera Induced by Vaccination with Cell-Derived and Egg-Adapted Monovalent H3N2 Vaccines As indicated above, in recent influenza seasons, antigenic mismatches between H3N2 vaccine strains and circulating strains have been associated with low vaccine effectiveness. In 2012-2013, the A/Victoria/361/2011-like clade 3C.1 vaccine strain was egg-adapted and was not a close antigenic match to the corresponding circulating strain. In 2014-2015, the A/Texas/50/2012 clade 3C.1 vaccine strain was antigenically distinct from dominant circulating strains due to antigenic drift. In 2015-2016, the A/Switzerland/9715293/2013 clade 3C.3a vaccine strain was not a close antigenic match to the corresponding circulating strain due to both egg-adaptation and antigenic drift.

To investigate the issue of mismatch in the context of H3N2 vaccine antigens, a mouse study was designed to explore cross-reactivity of mouse antisera induced by vaccination with cell-derived and egg-adapted monovalent H3N2 vaccines derived from three major clades (3C.1, 3C.2a, 3C.3a). Egg- and cell-derived inactivated influenza virus antigen monobulks corresponding to each clade, as shown in Table 3 below, were prepared in cell culture (using synthetic viruses based on the PR8x backbone and using HA and NA sequences from either the cell-derived or egg-adapted virus). Thus, as noted above, the designation "egg" or "cell" refers to the passage history of the viruses that provided the HA and NA sequences for synthesis. In cases of mixed passage history, any passage in eggs is sufficient to trigger an "egg" designation. HA levels were quantified by SRID and HA sequences were confirmed. SRID values are based on A/Switzerland9715293/2013 reagents.

TABLE 3

Egg- and cell-derived H3N2 monobulks prepared for mouse study

| Clade | H3N2 Virus Strain | Virus # | SRID (µg/ml) |
|---|---|---|---|
| 3C.1 | A/Texas/50/2012-egg | RG-ID-1958 | 287 |
|  | A/Texas/50/2012-cell | RG-PS-2341 | 182 |
| 3C.2a | A/Hong Kong/5738/2014-egg | RG-ID-2012 | 156 |
|  | A/Hong Kong/5738/2014-cell | RG-PS-2419 | 340 |
| 3C.3a | A/Switzerland/9715293/2013-egg | RG-PS-2404 | 296 |
|  | A/Switzerland/9715293/2013-cell | RG-PS-2407 | 217 |

Vaccines prepared from the monobulks were administered to BALB/c mice (10 mice per group), as shown in Table 4 (with or without MF59 adjuvant).

TABLE 4

Mouse study design

| Group | Day 0, 21, 42 vaccinations | HA dose (mcg) | Bleed days |
|---|---|---|---|
| 1 (TXe) | 3C.1 (egg) | 1 | 0, 20, 41, 63, 84 |
| 2 (TXc) | 3C.1 (cell) | 1 | 0, 20, 41, 63, 84 |
| 3 (HKe) | 3C.2a (egg) | 1 | 0, 20, 41, 63, 84 |
| 4 (HKc) | 3C.2a (cell) | 1 | 20, 41, 63, 84 |
| 5 (SWe) | 3C.3a (egg) | 1 | 20, 41, 63, 84 |
| 6 (SWc) | 3C.3a (cell) | 1 | 20, 41, 63, 84 |
| 7 (TXe) | 3C.1 (egg) + MF59 | 0.1 | 20, 41, 63, 84 |
| 8 (TXc) | 3C.1 (cell) + MF59 | 0.1 | 20, 41, 63, 84 |
| 9 (HKe) | 3C.2a (egg) + MF59 | 0.1 | 20, 41, 63, 84 |
| 10 (HKc) | 3C.2a (cell) + MF59 | 0.1 | 20, 41, 63, 84 |
| 11 (SWe) | 3C.3a (egg) + MF59 | 0.1 | 20, 41, 63, 84 |
| 12 (SWc) | 3C.3a (cell) + MF59 | 0.1 | 20, 41, 63, 84 |

Figure 11B:
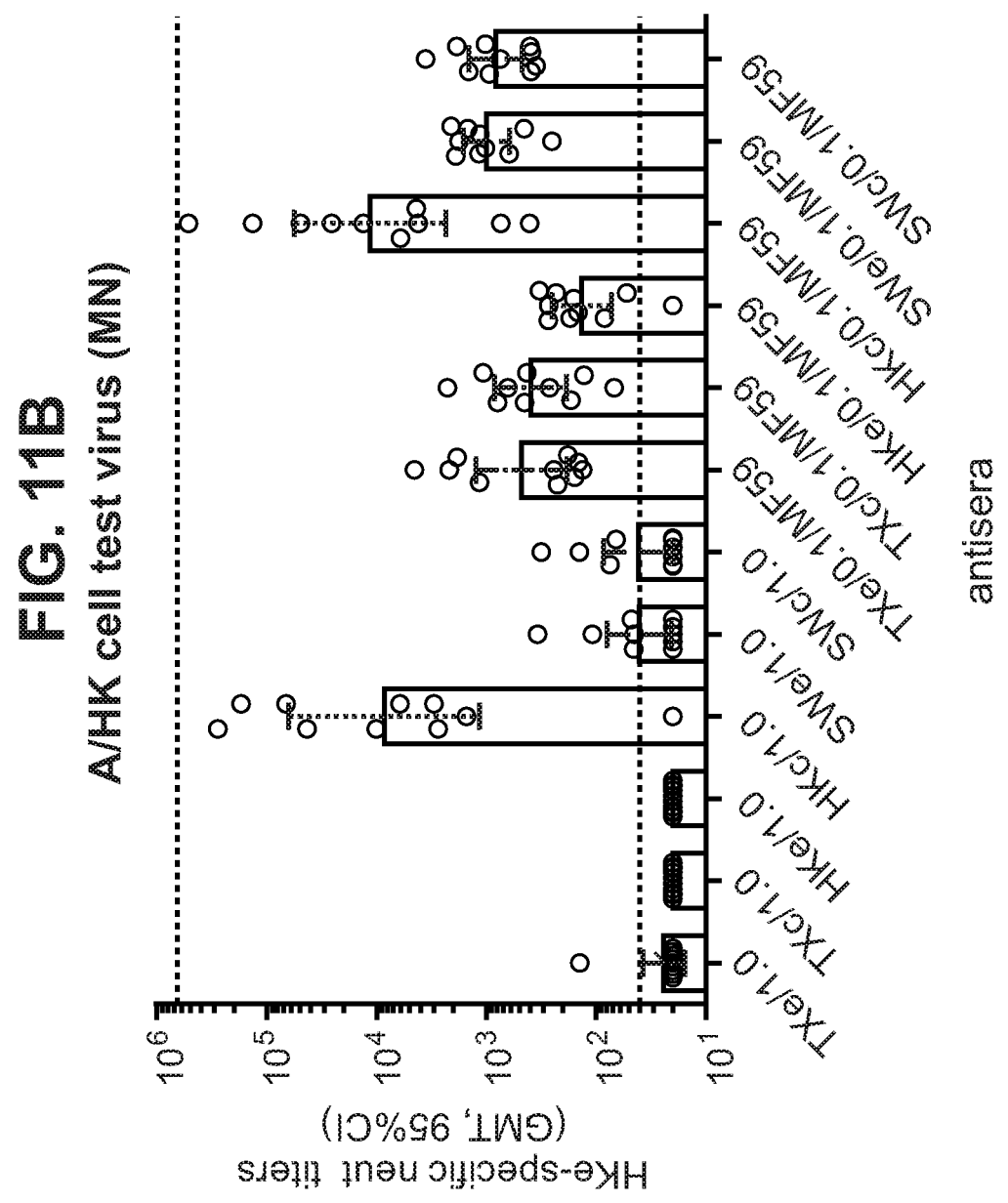

HI and MN assays were used to study serological cross-reactivity between the mouse antisera and the viral antigens. MN results are shown in FIGS. 11A and 11B. The data shown were generated using the day 41 bleed (3 weeks post second immunization). In general, antibody titers were highest against the homologous virus. MF59 increases overall antibody titers (in both HI and MN assays), but specificity is unchanged. Notably, there was a clear egg-cell antigenic mismatch for the clade 3C.2a A/Hong Kong/5738/2014 (A/HK) vaccine (e.g. compare 3rd and 4th columns of FIG. 11A with 11B). In particular, when the test virus was A/HK containing the egg-adapted HA and NA sequences, the virus was neutralized by all tested mouse antisera (FIG. 11A), including antisera to both the homologous egg-derived A/HK virus antigen and the cell-derived A/HK virus antigen. However, when the test virus was A/HK containing the cell-derived HA and NA sequences, the virus was neutralized by the homologous cell-derived A/HK antisera, but not by the antisera to the egg-derived A/HK virus antigen (FIG. 11B). The data obtained suggest that the A/HK egg-derived antigen contains immunodominant epitope(s) not present on the cell-derived virus, while the A/HK cell-derived antigen shares common epitopes with the egg-derived virus and elicits antibodies that can cross-react with the egg-derived virus.

Cross-reactivity data obtained using ferret antisera in an MN assay against A/HK cell-derived antigen and A/HK egg-derived antigen showed similar trends to the data obtained using mouse antisera (not shown).

Example 4: Animal Study to Investigate Monovalent, Inactivated Influenza A Virus (H3N2) Vaccine as a Rescue Vaccine The inventors have designed and commenced an in vivo study in which cell-derived monovalent, inactivated influenza A virus (H3N2) vaccine is used as a rescue vaccine to overcome antigenic mismatch between the corresponding vaccine antigen in an egg-derived trivalent vaccine and circulating virus.

Egg-derived trivalent (TIV) and cell-derived monovalent (MIV) vaccines were administered to BALB/c mice (10 mice per group), as shown in Table 5 (with or without MF59 adjuvant). TIV contains egg-derived A/Switzerland/9715293/2013 (H3N2), A/California/07/2009 (H1N1) and B/Brisbane/9/2014 virus antigens. MIV contains cell-derived A/Hong Kong/5738/2014 (H3N2) virus antigen. The TIV antigens were from egg-derived monobulks equivalent to those used to manufacture a trivalent influenza vaccine administered to humans during the 2015-2016 (northern hemisphere) seasonal vaccination campaign. The MIV antigens were produced in cell culture from a synthetic seed virus using HA and NA sequences from a cell-derived A/HK virus (i.e. a virus which has not been passaged in eggs).

TABLE 5

Rescue vaccine/H3N2 antigenic mismatch study design

| Group | Day 0 | Day 21 | Day 42 | Bleed days | Comment |
|---|---|---|---|---|---|
| 1 | TIV | TIV | — | 0, 20, 41, 63, 84 | TIV only |
| 2 | TIV | TIV | MIV | 0, 20, 41, 63, 84 | TIV followed by MIV |
| 3 | TIV + MIV | TIV + MIV | — | 0, 20, 41, 63, 84 | Concurrent |
| 4 | TIV | TIV | TIV | 20, 41, 63, 84 | TIV benchmark |
| 5 | MIV | MIV | MIV | 20, 41, 63, 84 | MIV benchmark |
| 6 | MIV | MIV | TIV | 20, 41, 63, 84 | Opposite order |
| 7 | aTIV | aTIV | — | 20, 41, 63, 84 | TIV only |
| 8 | aTIV | aTIV | aMIV | 20, 41, 63, 84 | TIV followed by MIV |
| 9 | aTIV + aMIV | aTIV + aMIV | — | 20, 41, 63, 84 | Concurrent |
| 10 | aTIV | aTIV | aTIV | 20, 41, 63, 84 | TIV benchmark |

TABLE 5-continued

Rescue vaccine/H3N2 antigenic mismatch study design

| Group | Day 0 | Day 21 | Day 42 | Bleed days | Comment |
|---|---|---|---|---|---|
| 11 | aMIV | aMIV | aMIV | 20, 41, 63, 84 | MIV benchmark |
| 12 | aMIV | aMIV | aTIV | 20, 41, 63, 84 | Opposite order |

Gr 1-6: unadjuvanted, dose = 1 mcg HA per strain
Gr 7-12: MF59-adjuvanted, dose = 0.1 mcg HA per strain The study will investigate serological cross-reactivity between the mouse antisera (e.g. obtained from the day 41 and/or day 63 bleeds) and the viral antigens in a similar manner to Example 3, using HI and MN assays. For example, MN and HI titers are to be obtained using the antisera from each group, tested against the cell-derived A/HK virus (from which the MIV antigen is derived) and the A/Switzerland egg-derived virus (from which the H3N2 component of the TIV is derived).

The study is expected to provide confirmation that administration of the better matched cell-derived MIV as a rescue vaccine will advantageously improve neutralizing antibody titers in vivo against the corresponding circulating strain, compared to TIV administration alone.

REFERENCES

1) Gerdil (2003) Vaccine 21:1776-9.
2) Palese (2006) Emerging Infectious Diseases 12:61-65.
3) WHO (2003) Weekly epidemiological record 78:73-80.
4) WO 02/28422.
5) WO 02/067983.
6) WO 02/074336.
7) WO 01/21151.
8) WO 02/097072.
9) WO 2005/113756.
10) Herlocher et al. (2004) J Infect Dis 190(9):1627-30.
11) Le et al. (2005) Nature 437(7062):1108.
12) Gambaryan & Matrosovich (1992) J Virol Methods 39(1-2):111-23.
13) Mastrosovich et al. (1999) J Virol 73: 1146-55.
14) Stevens et al. (2006) J Mol Biol 355:1143-55.
15) Couceiro & Baum (1994) Mem Inst Oswaldo Cruz 89(4):587-91.
16) WO 97/37000.
17) Brands et al. (1999) Dev Biol Stand 98:93-100.
18) Halperin et al. (2002) Vaccine 20:1240-7.
19) Tree et al. (2001) Vaccine 19:3444-50.
20) Kistner et al. (1998) Vaccine 16:960-8.
21) Kistner et al. (1999) Dev Biol Stand 98:101-110.
22) Bruhl et al. (2000) Vaccine 19:1149-58.
23) Pau et al. (2001) Vaccine 19:2716-21.
24) http://www.atcc.org/25)
25) http://locus.umdnj.edu/26)
26) WO 03/076601.
27) WO 2005/042728.
28) WO 03/043415.
29) WO 01/85938
30) WO 2006/108846
31) Schuind et al.; J Infect Dis. 2015 Feb. 25.
32) EP-A-1260581 (WO 01/64846).
33) WO 2006/071563.
34) WO 2005/113758.
35) WO 2006/027698.
36) Lundblad (2001) Biotechnology and Applied Biochemistry 34:195-197.
37) Guidance for Industry: Bioanalytical Method Validation. U.S. Department of Health and Human Services Food and Drug Administration Center for Drug Evaluation and Research (CDER) Center for Veterinary Medicine (CVM). May 2001.
38) Ji et al. (2002) Biotechniques. 32:1162-7.
39) Briggs (1991) J Parenter Sci Technol. 45:7-12.
40) Lahijani et al. (1998) Hum Gene Ther. 9:1173-80.
41) Lokteff et al. (2001) Biologicals. 29:123-32.
42) EP B 0870508.
43) U.S. Pat. No. 5,948,410.
44) WO 2007/052163.
45) WO 2010/052214.
46) WO 03/023021.
47) WO 03/023025.
48) WO 97/37001.
49) Hoffmann et al. (2002) Vaccine 20:3165-3170.
50) Subbarao et al. (2003) Virology 305:192-200.
51) Liu et al. (2003) Virology 314:580-590.
52) Ozaki et al. (2004) J. Virol. 78:1851-1857.
53) Webby et al. (2004) Lancet 363:1099-1103.
54) WO 00/60050.
55) WO 01/04333.
56) U.S. Pat. No. 6,649,372.
57) WO 2009/000891.
58) Neumann et al. (2005) Proc Natl Acad Sci USA 102: 16825-9.
59) WO 2006/067211.
60) WO 01/83794.
61) Hoffmann et al. (2000) Virology 267(2):310-7.
62) WO 2013/087945
63) WO 2014/141125
64) WO 01/22992.
65) Hehme et al. (2004) Virus Res. 103(1-2):163-71.
66) Treanor et al. (1996) J Infect Dis 173:1467-70.
67) Keitel et al. (1996) Clin Diagn Lab Immunol 3:507-10.
68) WO 96/37624.
69) WO 98/46262.
70) Gennaro (2000) Remington: The Science and Practice of Pharmacy. 20th edition, ISBN: 0683306472.
71) Banzhoff (2000) Immunology Letters 71:91-96.
72) Nony et al. (2001) Vaccine 27:3645-51.
73) Potter & Oxford (1979) Br Med Bull 35: 69-75.
74) WO 90/14837.
75) Podda & Del Giudice (2003) Expert Rev Vaccines 2:197-203.
76) Podda (2001) Vaccine 19: 2673-2680.
77) Vaccine Adjuvants: Preparation Methods and Research Protocols (Volume 42 of Methods in Molecular Medicine series). ISBN: 1-59259-083-7. Ed. O'Hagan.
78) Allison & Byars (1992) Res Immunol 143:519-25.
79) Hariharan et al. (1995) Cancer Res 55:3486-9.
80) WO 95/11700.
81) U.S. Pat. No. 6,080,725.
82) WO 2005/097181.
83) WO 2006/113373.

84) Han et al. (2005) Impact of Vitamin E on Immune Function and Infectious Diseases in the Aged at Nutrition, Immune functions and Health EuroConference, Paris, 9-10 Jun. 2005.
85) U.S. Pat. No. 6,630,161.
86) Kandimalla et al. (2003) Nucleic Acids Research 31:2393-2400.
87) WO 02/26757.
88) WO 99/62923.
89) Krieg (2003) Nature Medicine 9:831-835.
90) McCluskie et al. (2002) FEMS Immunology and Medical Microbiology 32:179-185.
91) WO 98/40100.
92) U.S. Pat. No. 6,207,646.
93) U.S. Pat. No. 6,239,116.
94) U.S. Pat. No. 6,429,199.
95) Kandimalla et al. (2003) Biochemical Society Transactions 31 (part 3):654-658.
96) Blackwell et al. (2003) J Immunol 170:4061-4068.
97) Krieg (2002) Trends Immunol 23:64-65.
98) WO 01/95935.
99) Kandimalla et al. (2003) BBRC 306:948-953.
100) Bhagat et al. (2003) BBRC 300:853-861.
101) WO 03/035836.
102) WO 01/22972.
103) Thompson et al. (2005) J Leukoc Biol 78: The low-toxicity versions of LPS, MPL® adjuvant and RC529, are efficient adjuvants for CD4+ T cells'.
104) UK patent application GB A 2220211.
105) WO 94/21292.
106) WO 94/00153.
107) WO 95/17210.
108) WO 96/26741.
109) WO 93/19780.
110) Skowronski D M, Janjua N Z, De Serres G, Sabaiduc S, Eshaghi A, Dickinson J A, et al. Low 2012-13 influenza vaccine effectiveness associated with mutation in the egg-adapted H3N2 vaccine strain not antigenic drift in circulating viruses. PloS one. 2014; 9:e92153.
111) Belongia E A, Kieke B A, Donahue J G, Greenlee R T, Balish A, Foust A, et al. Effectiveness of inactivated influenza vaccines varied substantially with antigenic match from the 2004-2005 season to the 2006-2007 season. The Journal of infectious diseases. 2009; 199: 159-67.
112) CDC. Early Estimates of Seasonal Influenza Vaccine Effectiveness—United States, January 2015. MMWR Morb Mortal Wkly Rep Center for Disease Control and Prevention; 2015. p. 10-5.
113) Roth B, Mohr H, Enders M, Garten W, Gregersen J P. Isolation of influenza viruses in MDCK 33016PF cells and clearance of contaminating respiratory viruses. Vaccine. 2012; 30:517-22.
114) Stevens J, Chen L M, Carney P J, Garten R, Foust A, Le J, et al. Receptor specificity of influenza A H3N2 viruses isolated in mammalian cells and embryonated chicken eggs. Journal of virology. 2010; 84:8287-99.
115) Widjaja L, Ilyushina N, Webster R G, Webby R J. Molecular changes associated with adaptation of human influenza A virus in embryonated chicken eggs. Virology. 2006; 350:137-45.
116) Shinya K, Ebina M, Yamada S, Ono M, Kasai N, Kawaoka Y. Avian flu: influenza virus receptors in the human airway. Nature. 2006; 440:435-6.
117) Ito T, Suzuki Y, Takada A, Kawamoto A, Otsuki K, Masuda H, et al. Differences in Sialic Acid-Galactose Linkages in the Chicken Egg Amnion and Allantois Influence Human Influenza Virus Receptor Specificity and Variant Selection. J Virol. 1997; 71:3357-62.
118) Rogers G N, Daniels R S, Skehel J J, Wiley D C, Wang X, Higa H H, et al. Host-mediated Selection of Influenza Virus Receptor Variants. The Journal of biological chemistry. 1985; 260:7362-7.
119) Kishida N, Fujisaki S, Yokoyama M, Sato H, Saito R, Ikematsu H, et al. Evaluation of influenza virus A/H3N2 and B vaccines on the basis of cross-reactivity of post-vaccination human serum antibodies against influenza viruses A/H3N2 and B isolated in MDCK cells and embryonated hen eggs. Clinical and vaccine immunology: CVI. 2012; 19:897-908.
120) NIMR. Report prepared for the WHO annual consultation on the composition of influenza vaccine for the Northern Hemisphere 2015-16. http://www.nimr.mrc.ac.uk/documents/about/NIMR-report-Feb2015-web.pdf2015.
121) Meyer W J, Wood J M, Major D, Robertson J S, Webster R G, Katz J M. Influence of Host Cell-Mediated Variation on the International Surveillance of Influenza A (H3N2) Viruses. Virology. 1993; 196:130-7.
122) Katz J M, Wang M, Webster R G. Direct Sequencing of the H A Gene of Influenza (H3N2) Virus in Original Clinical Samples Reveals Sequence Identity with Mammalian Cell-Grown Virus. J Virol. 1990; 64:1808-11.
123) Donis R O, Influenza Cell Culture Working G, Influenza Cell Culture Working G. Performance characteristics of qualified cell lines for isolation and propagation of influenza viruses for vaccine manufacturing. Vaccine. 2014; 32:6583-90.
124) Dormitzer P R, Suphaphiphat P, Gibson D G, Wentworth D E, Stockwell T B, Algire M A, et al. Synthetic generation of influenza vaccine viruses for rapid response to pandemics. Science translational medicine. 2013; 5:185ra68.
125) Bottcher E, Matrosovich T, Beyerle M, Klenk H D, Garten W, Matrosovich M. Proteolytic activation of influenza viruses by serine proteases TMPRSS2 and HAT from human airway epithelium. Journal of virology. 2006; 80:9896-8.
126) Chen Z, Zhou H, Jin H. The impact of key amino acid substitutions in the hemagglutinin of influenza A (H3N2) viruses on vaccine production and antibody response. Vaccine. 2010; 28:4079-85.
127) Minor P D, Engelhardt O G, Wood J M, Robertson J S, Blayer S, Colegate T, et al. Current challenges in implementing cell-derived influenza vaccines: implications for production and regulation, July 2007, NIBSC, Potters Bar, U K. Vaccine. 2009; 27:2907-13.
128) Minor P D. Vaccines against seasonal and pandemic influenza and the implications of changes in substrates for virus production. Clinical infectious diseases: an official publication of the Infectious Diseases Society of America. 2010; 50:560-5.
129) Oxford J S, Corcoran T, Knott R, Bates J, Bartolomei O, Major D, et al. Serological studies with influenza A (H1N1) viruses cultivated in eggs or in a canine kidney cell line (MDCK). Bulletin of the World Health Organization. 1987; 65:181-7.
130) Schild G C, Oxford J S, de Jong J C, Webster R G. Evidence for host-cell selection of influenza virus antigenic variants. Nature. 1983; 303.
131) Bart S A, Hohenboken M, Della Cioppa G, Narasimhan V, Dormitzer P R, Kanesa-thasan N. A Cell Culture- Derived MF59-Adjuvanted Pandemic A/H7N9 Vaccine in Immunogenic in Adults. Sience Translational Medicine. 2014; 6:234ra55.
132) Lin Y P, Gregory V, Collins P, Kloess J, Wharton S, Cattle N, et al. Neuraminidase receptor binding variants of human influenza A(H3N2) viruses resulting from substitution of aspartic acid 151 in the catalytic site: a role in virus attachment? Journal of virology. 2010; 84:6769-81.
133) *Vaccine Design: The Subunit and Adjuvant Approach* (eds. Powell & Newman) Plenum Press 1995 (ISBN 0-306-44867-X).

The various features and embodiments of the present invention, referred to in individual sections above apply, as appropriate, to other sections, mutatis mutandis. Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for immunizing a human who has previously been administered a first influenza vaccine comprising an antigen from a first influenza virus which has been passaged in eggs, comprising administering to the same human a second influenza vaccine comprising an antigen from a second influenza virus which has not been passaged in eggs, wherein the antigen in the second influenza vaccine is more closely antigenically matched to a circulating strain than the antigen in the first influenza vaccine, and wherein the first influenza vaccine and the second influenza vaccine are from one influenza season.

2. A method for immunizing a human, comprising steps of (a) administering to the human a first influenza vaccine comprising an antigen from a first influenza virus which has been passaged in eggs; and subsequently (b) administering to the same human a second influenza vaccine comprising an antigen from a second influenza virus which has been grown in cell culture, wherein the antigen in the second influenza vaccine is more closely antigenically matched to a circulating strain than the antigen in the first influenza vaccine, and wherein the first and the second influenza vaccine are administered within the same influenza season.

3. The method of claim 1, wherein the second influenza virus has been grown in cell culture.

4. The method of claim 1, wherein the antigen from the second influenza vaccine is a recombinant protein antigen.

5. The method of claim 1, wherein the first influenza vaccine is made available prior to the second influenza vaccine.

6. The method of claim 1, wherein the influenza antigen in the first vaccine is from an influenza virus that has been grown in eggs.

7. The method of claim 1, wherein the first influenza vaccine is a trivalent influenza vaccine or a tetravalent influenza vaccine.

8. The method of claim 1, wherein the second influenza vaccine is a monovalent influenza vaccine.

9. A method for immunizing a human who has previously been administered a first influenza vaccine comprising an antigen from a first influenza virus which has been passaged in eggs, comprising administering to the same human a second influenza vaccine comprising an antigen from a second influenza virus which has not been passaged in eggs, wherein the antigen in the second influenza vaccine is more closely antigenically matched to a circulating strain than the antigen in the first influenza vaccine, and wherein the first and the second influenza vaccine are administered within the same influenza season.

10. The method of claim 1, wherein the second influenza vaccine is free from ovalbumin and ovomucoid.

11. The method of claim 1, wherein (i) the first influenza vaccine is an inactivated virus vaccine, (ii) the second influenza vaccine is an inactivated virus vaccine, or (iii) the first and the second influenza vaccine is an inactivated virus vaccine.

12. The method of claim 1, wherein the antigen in the second influenza vaccine was prepared from an influenza virus that has never been passaged in eggs.

13. The method of claim 1, wherein the first and/or the second influenza vaccine is adjuvanted.

14. The method of claim 13, wherein the adjuvant is an oil-in-water emulsion adjuvant.

15. The method of claim 1, wherein the antigen from the second influenza vaccine is manufactured from a synthetic seed virus.

16. The method of claim 2, wherein the influenza antigen in the first vaccine is from an influenza virus that has been grown in eggs.

17. The method of claim 2, wherein the first influenza vaccine is a trivalent influenza vaccine or a tetravalent influenza vaccine.

18. The method of claim 2, wherein the second influenza vaccine is a monovalent influenza vaccine.

19. The method of claim 2, wherein the second influenza vaccine is free from ovalbumin and ovomucoid.

20. The method of claim 2, wherein (i) the first influenza vaccine is an inactivated virus vaccine, (ii) the second influenza vaccine is an inactivated virus vaccine, or (iii) the first and the second influenza vaccine is an inactivated virus vaccine.

21. The method of claim 2, wherein the antigen in the second influenza vaccine was prepared from an influenza virus that has never been passaged in eggs.

22. The method of claim 2, wherein the first and/or the second influenza vaccine is adjuvanted.

23. The method of claim 2, wherein the antigen from the second influenza vaccine is manufactured from a synthetic seed virus.

\* \* \* \* \*